US012327613B2

(12) United States Patent
Baker et al.

(10) Patent No.: US 12,327,613 B2
(45) Date of Patent: Jun. 10, 2025

(54) DE NOVO ANTIBODY DESIGN

(71) Applicant: UCB Biopharma SRL, Brussels (BE)

(72) Inventors: Terence Seward Baker, Slough (GB); Xiaofeng Liu, Slough (GB); Jiye Shi, Slough (GB); Richard David Taylor, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 1541 days.

(21) Appl. No.: 15/781,228

(22) PCT Filed: Dec. 1, 2016

(86) PCT No.: PCT/EP2016/079497
§ 371 (c)(1),
(2) Date: Jun. 4, 2018

(87) PCT Pub. No.: WO2017/093435
PCT Pub. Date: Jun. 8, 2017

(65) Prior Publication Data
US 2020/0168293 A1    May 28, 2020

(30) Foreign Application Priority Data
Dec. 4, 2015 (GB) ...................... 1521447

(51) Int. Cl.
*G16B 15/00* (2019.01)
*G06F 30/20* (2020.01)
(Continued)

(52) U.S. Cl.
CPC ............. *G16B 15/00* (2019.02); *G06F 30/20* (2020.01); *G16B 20/30* (2019.02); *G16B 20/50* (2019.02)

(58) Field of Classification Search
CPC ........ G16B 15/00; G16B 20/30; G16B 20/50; G06F 30/20
(Continued)

(56) References Cited

U.S. PATENT DOCUMENTS

2005/0277173 A1   12/2005 Chin
2009/0130102 A1   5/2009 Weaver et al.

FOREIGN PATENT DOCUMENTS

CN    102143977    8/2011
CN    102170909    8/2011
(Continued)

OTHER PUBLICATIONS

Kannan Tharakaraman, Luke N. Robinson, Andrew Hatas, Yi-Ling Chen, Liu Siyue, S. Raguram, V. Sasisekharan, Gerald N. Wogan, and Ram Sasisekharan: Redesign of a cross-reactive antibody to dengue virus with broad-spectrum activity and increased in vivo potency, PNAS Apr. 23, 2013 110 (17) E1555-E1564 (Year: 2013).*
(Continued)

*Primary Examiner* — Larry D Riggs, II
*Assistant Examiner* — Guozhen Liu
(74) *Attorney, Agent, or Firm* — McDonnell Boehnen Hulbert & Berghoff LLP

(57) ABSTRACT

Computer-implemented methods of designing an antibody that will bind to a target epitope are disclosed. In one arrangement, the method comprises identifying one or more hotspot residues that will each bind to a corresponding one of one or more hotspot sites on the target epitope. Candidate antibody structures are selected from a database such that characteristic atoms within the antibody structure and hotspot characteristic atoms can be superimposed computationally with an averaged spatial deviation less than a predetermined threshold. A designed antibody is generated by
(Continued)

replacing matching residues with different residues such that a predicted affinity is increased.

22 Claims, 29 Drawing Sheets

Specification includes a Sequence Listing.

(51) Int. Cl.
    *G16B 20/30*     (2019.01)
    *G16B 20/50*     (2019.01)
    *G16B 30/20*     (2019.01)

(58) Field of Classification Search
    USPC .......................................................... 703/11
    See application file for complete search history.

(56) References Cited

FOREIGN PATENT DOCUMENTS

| | | |
|---|---|---|
| CN | 102482355 | 5/2012 |
| JP | 2009530422 | 8/2009 |
| WO | WO2013093627 | 6/2013 |
| WO | WO2014022817 | 6/2014 |

OTHER PUBLICATIONS

Li T, Pantazes RJ, Maranas CD (2014) OptMAVEn—A New Framework for the de novo Design of Antibody Variable Region Models Targeting Specific Antigen Epitopes. PLoS ONE 9(8): e105954. doi:10.1371/journal.pone.0105954 (Year: 2014).*

Sormanni, Pietro, Francesco A. Aprile, and Michele Vendruscolo. "Rational design of antibodies targeting specific epitopes within intrinsically disordered proteins." Proceedings of the National Academy of Sciences 112.32 (2015): 9902-9907. (Year: 2015).*

Pantazes, R. J., and Costas D. Maranas. "OptCDR: a general computational method for the design of antibody complementarity determining regions for targeted epitope binding." Protein Engineering, Design & Selection 23.11 (2010): 849-858. (Year: 2010).*

Kashmiri et al., "SDR grafting-a new approach to antibody humanization," Methods, Academic Press, US, vol. 36, No. 1, May 1, 2005, pp. 25-34.

L N Robinson et al. Structure-guided design of an anti-dengue antibody directed to a non-immunodominant epitope. (2015) Cell 162. 493-504.

S M Lippow et al. Computational design of antibody-affinity improvement beyond in vivo maturation. (2007) Nature Biotechnology. vol 25. 1171-1176.

D Kuroda et al. Computer-aided antibody design. (2012) Protein Engineering, Design & Selection. vol 25. 507-521.

J L Jordan et al. Structural understanding of stabilization patterns in engineered bispecific Ig-like antibody molecules. (2009) Proteins. vol 77. 832-841.

G D Lapidoth et al. AbDesign: An algorithm for combinatorial backbone design guided by natural conformations and sequences. (2015) Proteins. vol 83. 1385-1406.

K.R Abhinandan et al. Analysis and improvements to Kabat and structurally correct numbering of antibody variable domains. (2008) Molecular Immunology. vol 45. 3832-3839.

B Al-Lazikani et al. Standard conformations for the canonical structures of immunoglobulins. (1997) Journal of Molecular Biology. vol 273. pp. 927-948.

S J Fleishman et al. Computational design of proteins targeting the conserved stem region of influenza hemagglutinin. (2011) Science. vol. 332. 816-821.

S Liu et al. Nonnatural protein-protein interaction-pair design by key residues grafting. (2007) Natural Academy of Sciences of the USA. vol. 104. 5330-5335.

S J Fleishman et al. Hotspot-centric de novo design of protein binders. (2011) Journal of Molecular Biology. vol 413. 1047-1062.

L A Clark et al. An antibody loop replacement design feasibility study and a loop- swapped dimer structure. (2009) Protein Engineering, Design & Selection. vol 22. 93-101.

E Soderlind et al. Recombining germline-derived CDR sequences for creating diverse single-framework antibody libraries. (2000) Nature Biotechnology. vol 18. 852-856.

B North et al. A new clustering of antibody CDR loop conformations. (2011) Journal of Molecular Biology. vol 406. 228-256.

B Kuhlman et al. Design of a novel globular protein fold with atomic-level accuracy. (2003) Science. vol 302. 1364-1368.

H J Wolfson et al. Geometric Hashing (1997).

S J Fleishman et al. RosettaScripts: A scripting language interface to the Rosetta macromolecular modelling suite. (2011) PLos One. vol 6. E20161.

C A Smith et al. Backrub like backbone simulation recapitulates natural protein conformational variability and improves mutant side-chain prediction. (2008) Journal of Molecular Biology. vol 380. 742-756.

M C Lawrence et al. Shape complementarity at protein/protein interfaces. (1993) Journal of Molecular Biology. vol. 234. 946-950.

P B Stranges et al. A comparison of successful and failed protein interface designs highlights the challenges of designing buried hydrogen bonds. (2013) Protein Science. vol 22. 74-82.

R Das et al. Macromolecular modelling with Rosetta. (2008) Annual Review of Biochemistry vol. 77. 363-382.

S C Lo et al. Structure of the Keap1: Nrf2 interface provides mechanistic insight into Nrf2 signalling. (2006) The Embo Journal. vol 25. 3605-3617.

Z Hu et al. Conservation of polar residues as hot spots at protein interfaces. (2000) Proteins. vol 39. 331-342.

A J McCoy et al. Phaser crystallographic software. (2007) Journal of Applied Crystallography. vol 40. 658-674.

E Potterton et al. A graphical user interface to the CCP4 program suite. (2003) Biological Crystallography, Acta Crystallographica, D59. 1131-1137.

M D Winn et al. Overview of the CCP4 suite and current developments. Biological Crystallography, Acta Crystallographica, D67. (2011) D67. 235-242.

B Padmanabhan et al. Structural basis for defects of Keap1 activity provoked by its point mutations in lung cancer. (2006) Molecular Cell. 689-700.

D M Shechner et al. Crystal Structure of the catalytic core of an RNA-Polymerase Ribozyme. (2009) Science vol. 326. 1271-1275.

G N Murshudov et al. Refinement of macromolecular structures by the maximum- likelihood method. (1997) Biological Crystallography, Acta Crystallography D53. 240-255.

P Emsley et al. Coot: Model-building tools for molecular graphics. (2004) Biological Crystallography, Acta Crystallographica, D60. 2126-2132.

S C Lovell et al. Structure validation by Calpha geometry: phi,psi and Cbeta deviation. (2003) Proteins. vol 50. 437-450.

R A Laskowski et al. Procheck: A program to check the stereochemical quality of protein structures. (1993) Journal of Applied Crystallography. vol 26. 283-291.

A Vaguine et al. SFCHECK: a unified set of procedures for evaluating the quality of macromolecular structure-factor data and their agreement with the atomic model. (1999) Biological Crystallography, Acta Crystallography D55. 191-205.

X Liu et al. Shafts: A hybrid approach for 3D molecular similarity calculation. (2011) Journal of Chemistry. vol 51. 2372-2385.

A Wallace et al. Tess: A Geometric hashing algorithm for deriving 3D coordinate templates. (1997) Protein Science. vol 6. 2308-2323.

K Kaufmann et al. Practically useful: what the Rosetta protein modelling suite can do for you. (2010) Biochemistry. vol 49. 2987-2998.

Search Report on UK Application No. GB1521447.1, dated Sep. 22, 2016.

Office action on JP Application No. 2018-528602, dated Nov. 26, 2020 (translation included).

Search report on CN 201680077968.1 dated Oct. 15, 2021 (translation included).

Office action on on CN 201680077968.1 (translation included).

* cited by examiner

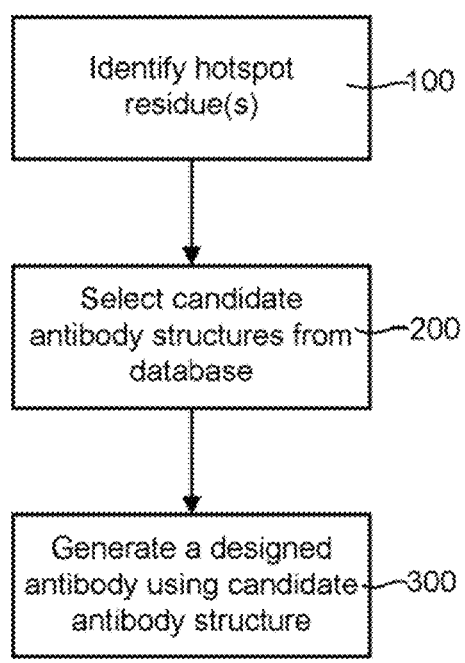
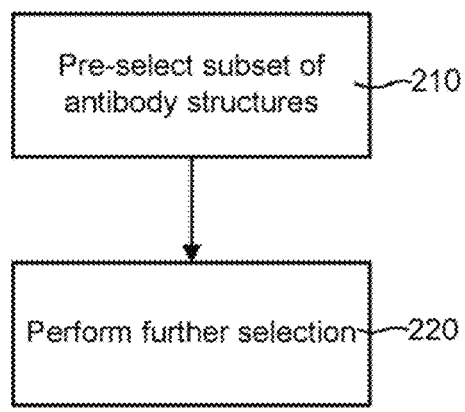

Fig. 8

- 221 — Superimpose characteristic atoms
- 226 — Try different antibody structure
- 222 — Calculate average spatial deviation
- 225 — Shift relative positions of characteristic atoms between hotspot and antibody structure sets
- 223 — Below threshold?
- 224 — Max iterations exceeded?
- 227 — Output

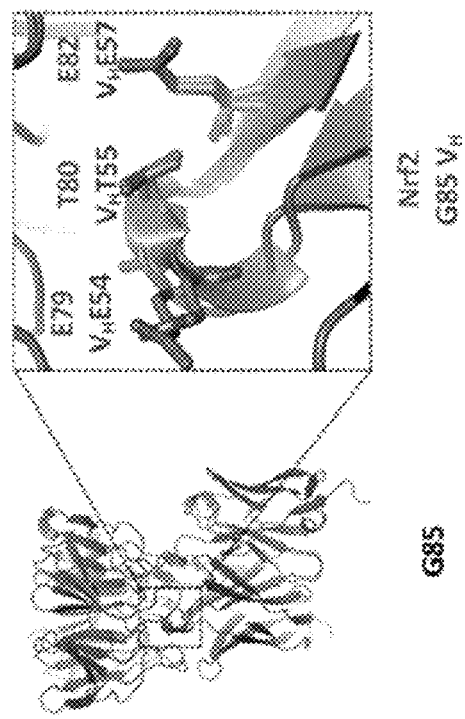
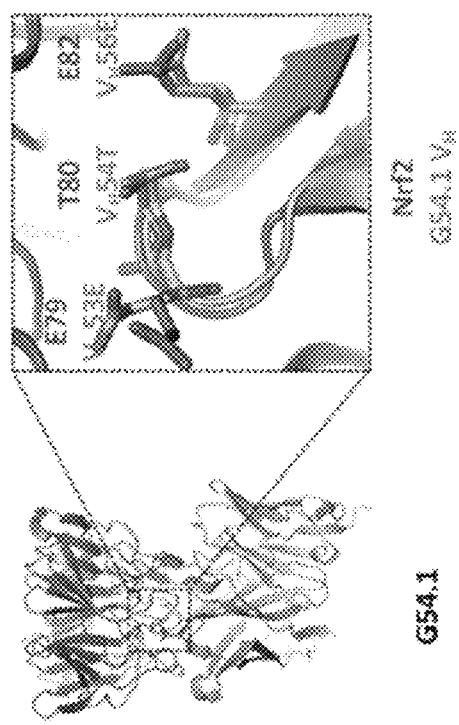
Fig. 14

Fig. 23
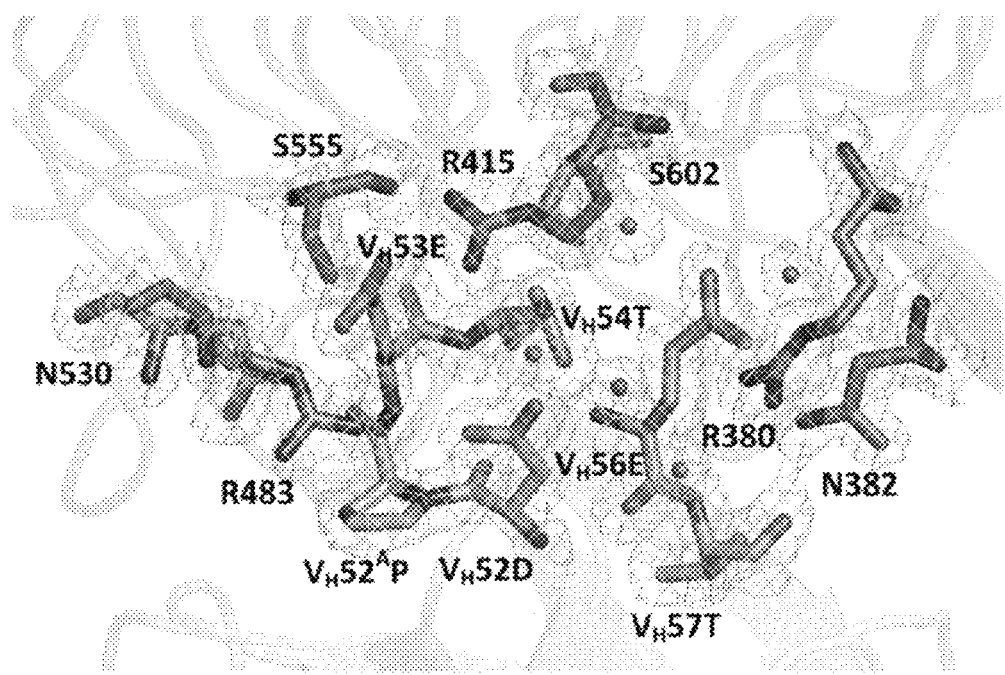
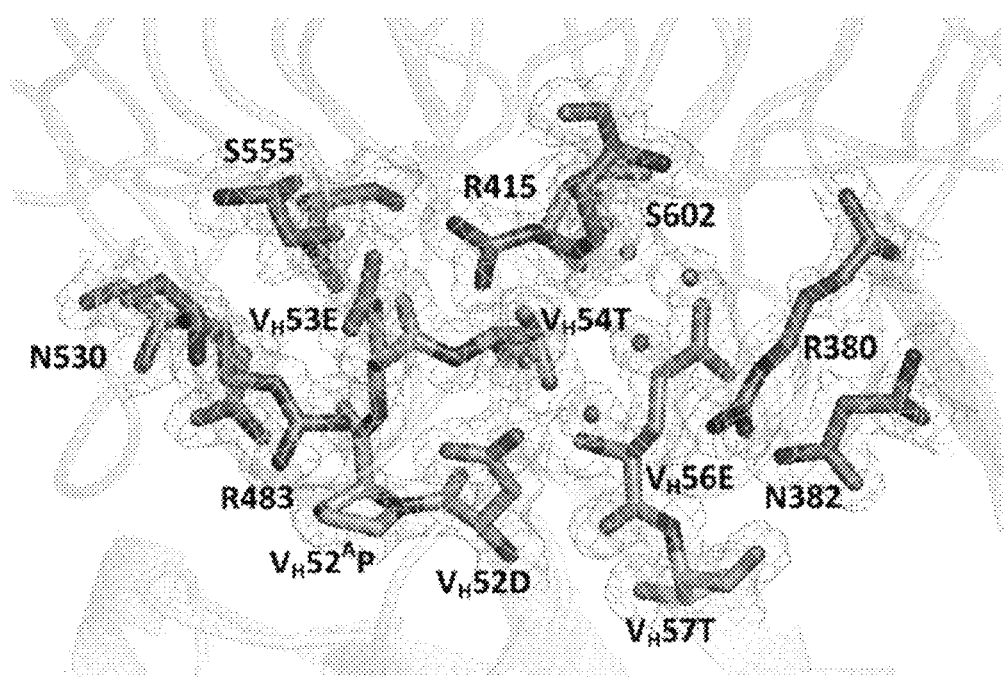
LS146-scFv $V_H$/Keap1

H2

H3

$V_H$ FR3

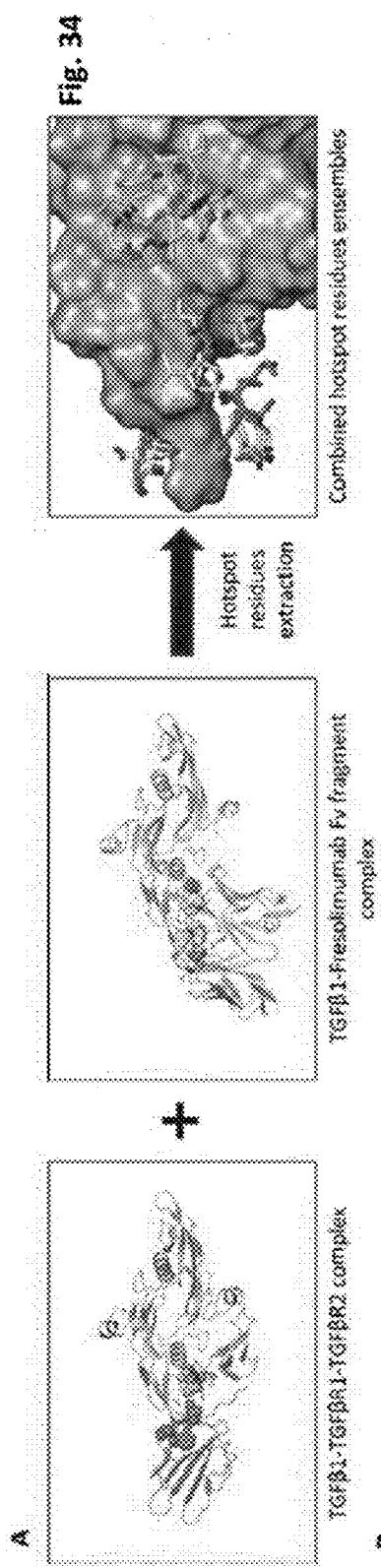
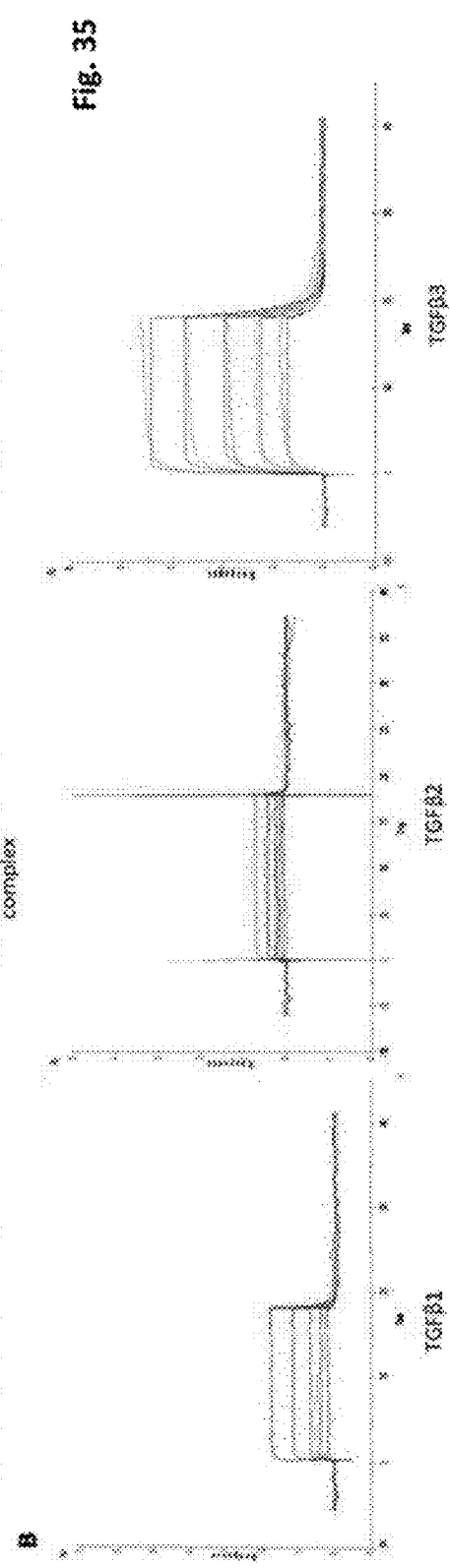

SEQUENCE LISTING

<160> NUMBER OF SEQ ID NOS: 74

<210> SEQ ID NO 1
<211> LENGTH: 113
<212> TYPE: PRT
<213> ORGANISM: Artificial sequence
<220> FEATURE:
<223> OTHER INFORMATION: Fv region

<400> SEQUENCE: 1

Gln Val Gln Leu Gln Glu Ser Gly Pro Gly Leu Met Lys Pro Ser Glu
1               5                   10                  15

Thr Leu Ser Leu Thr Cys Ser Val Ser Gly Asp Ser Ile Ala Ala Asp
            20                  25                  30

Tyr Trp Ser Trp Ile Arg Lys Pro Pro Gly Lys Gly Leu Glu Tyr Ile
        35                  40                  45

Gly Tyr Val Ser Glu Thr Gly Glu Thr Tyr Tyr Asn Pro Ser Leu Lys
    50                  55                  60

Ser Arg Val Thr Ile Ser Val Asp Ala Ser Lys Asn Arg Phe Ser Leu
65                  70                  75                  80

Lys Leu Asn Ser Val Thr Ala Ala Asp Thr Ala Val Tyr Tyr Cys Ala
                85                  90                  95

Arg Trp Asp Gly Asp Tyr Trp Gly Gln Gly Ile Leu Val Thr Val Ser
            100                 105                 110

Ser

<210> SEQ ID NO 2
<211> LENGTH: 107
<212> TYPE: PRT
<213> ORGANISM: Artificial sequence
<220> FEATURE:
<223> OTHER INFORMATION: Fv region

<400> SEQUENCE: 2

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Asn Ser Trp Pro Tyr
                85                  90                  95

Thr Phe Gly Gly Gly Thr Lys Val Glu Ile Lys
            100                 105

<210> SEQ ID NO 3
<211> LENGTH: 113
<212> TYPE: PRT
<213> ORGANISM: Artificial sequence
<220> FEATURE:
<223> OTHER INFORMATION: Fv region

<400> SEQUENCE: 3

Gln Val Gln Leu Gln Glu Ser Gly Pro Gly Leu Met Lys Pro Ser Glu
1               5                   10                  15

-continued

Thr Leu Ser Leu Thr Cys Ser Val Ser Gly Asp Ser Ile Ala Ala Asp
            20                  25                  30

Tyr Trp Ser Trp Ile Arg Lys Pro Gly Lys Gly Leu Glu Tyr Ile
        35                  40                  45

Gly Tyr Val Asp Glu Thr Gly Glu Thr Tyr Tyr Asn Pro Ser Leu Lys
 50                  55                  60

Arg Arg Val Thr Ile Ser Val Asp Ala Ser Lys Asn Arg Phe Ser Leu
65                  70                  75                  80

Lys Leu Asn Ser Val Thr Ala Ala Asp Thr Ala Val Tyr Tyr Cys Ala
                85                  90                  95

Arg Trp Asp Gly Asp Tyr Trp Gly Gln Gly Ile Leu Val Thr Val Ser
            100                 105                 110

Ser

<210> SEQ ID NO 4
<211> LENGTH: 107
<212> TYPE: PRT
<213> ORGANISM: Artificial sequence
<220> FEATURE:
<223> OTHER INFORMATION: Fv region

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
 50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Asn Ser Trp Pro Tyr
                85                  90                  95

Thr Phe Gly Gly Gly Thr Lys Val Glu Ile Lys
            100                 105

<210> SEQ ID NO 5
<211> LENGTH: 122
<212> TYPE: PRT
<213> ORGANISM: Artificial sequence
<220> FEATURE:
<223> OTHER INFORMATION: Fv region

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Ser Pro Glu Thr Gly Glu Thr Tyr Tyr Ala Asp Ser Val
 50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Ala Ala Arg Ser Gly Ala Gly Phe Asp Tyr Trp
            100                 105                 110

Gly Gln Gly Thr Leu Val Thr Val Ser Ser
        115                 120

<210> SEQ ID NO 6
<211> LENGTH: 107
<212> TYPE: PRT
<213> ORGANISM: Artificial sequence
<220> FEATURE:
<223> OTHER INFORMATION: Fv region

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Ser
                85                  90                  95

Thr Phe Gly Gln Gly Thr Lys Val Glu Ile Lys
            100                 105

<210> SEQ ID NO 7
<211> LENGTH: 122
<212> TYPE: PRT
<213> ORGANISM: Artificial sequence
<220> FEATURE:
<223> OTHER INFORMATION: Fv region

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Ala Ala Arg Ser Gly Ala Gly Phe Asp Tyr Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial sequence
<220> FEATURE:
<223> OTHER INFORMATION: Fv region

```
-continued

<400> SEQUENCE: 8

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Ser
                85                  90                  95

Thr Phe Gly Gln Gly Thr Lys Val Glu Ile Lys
            100                 105

<210> SEQ ID NO 9
<211> LENGTH: 133
<212> TYPE: PRT
<213> ORGANISM: Artificial sequence
<220> FEATURE:
<223> OTHER INFORMATION: Fv region

<400> SEQUENCE: 9

Glu Val Gln Leu Val Glu Ser Gly Gly Gly Leu Ile Arg Pro Gly Gly
1               5                   10                  15

Ser Leu Arg Leu Ser Cys Lys Gly Ser Gly Phe Ile Phe Glu Asn Phe
            20                  25                  30

Gly Phe Gly Trp Val Arg Gln Gly Pro Gly Lys Gly Leu Glu Trp Val
        35                  40                  45

Ser Gly Thr Asn Trp Asn Gly Gly Asp Ser Arg Tyr Gly Asp Ser Val
    50                  55                  60

Lys Gly Arg Phe Thr Ile Ser Arg Asp Asn Ser Asn Asn Phe Val Tyr
65                  70                  75                  80

Leu Gln Met Asn Ser Leu Arg Pro Glu Asp Thr Ala Ile Tyr Tyr Cys
                85                  90                  95

Ala Arg Gly Thr Asp Tyr Thr Ile Asp Glu Thr Gly Glu Arg Tyr Gln
            100                 105                 110

Gly Ser Gly Thr Phe Trp Tyr Phe Asp Val Trp Gly Arg Gly Thr Leu
        115                 120                 125

Val Thr Val Ser Ser
        130

<210> SEQ ID NO 10
<211> LENGTH: 108
<212> TYPE: PRT
<213> ORGANISM: Artificial sequence
<220> FEATURE:
<223> OTHER INFORMATION: Fv region

<400> SEQUENCE: 10

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val His Ser Arg
            20                  25                  30

Tyr Phe Ala Trp Tyr Gln His Lys Pro Gly Gln Pro Pro Arg Leu Leu
        35                  40                  45
```

```
Ile Tyr Gly Gly Ser Thr Arg Ala Thr Gly Ile Pro Asn Arg Phe Ser
    50                  55                  60

Ala Gly Gly Ser Gly Thr Gln Phe Thr Leu Thr Val Asn Arg Leu Glu
65                  70                  75                  80

Ala Glu Asp Phe Ala Val Tyr Tyr Cys Gln Gln Tyr Gly Ala Ser Pro
                85                  90                  95

Tyr Thr Phe Gly Gln Gly Thr Lys Val Glu Ile Arg
            100                 105

<210> SEQ ID NO 11
<211> LENGTH: 133
<212> TYPE: PRT
<213> ORGANISM: Artificial sequence
<220> FEATURE:
<223> OTHER INFORMATION: Fv region

<400> SEQUENCE: 11

Glu Val Gln Leu Val Glu Ser Gly Gly Gly Leu Ile Arg Pro Gly Gly
1               5                   10                  15

Ser Leu Arg Leu Ser Cys Lys Gly Ser Gly Phe Ile Phe Glu Asn Phe
                20                  25                  30

Gly Phe Gly Trp Val Arg Gln Gly Pro Gly Lys Gly Leu Glu Trp Val
            35                  40                  45

Ser Gly Thr Asn Trp Asn Gly Gly Asp Ser Arg Tyr Gly Asp Ser Val
    50                  55                  60

Lys Gly Arg Phe Thr Ile Ser Arg Asp Asn Ser Asn Asn Phe Val Tyr
65                  70                  75                  80

Leu Gln Met Asn Ser Leu Arg Pro Glu Asp Thr Ala Ile Tyr Tyr Cys
                85                  90                  95

Ala Arg Gly Thr Asp Tyr Thr Ile Asp Glu Thr Gly Glu Arg Tyr Gln
            100                 105                 110

Gly Ser Gly Thr Phe Trp Tyr Phe Asp Val Trp Gly Arg Gly Thr Leu
        115                 120                 125

Val Thr Val Ser Ser
        130

<210> SEQ ID NO 12
<211> LENGTH: 108
<212> TYPE: PRT
<213> ORGANISM: Artificial sequence
<220> FEATURE:
<223> OTHER INFORMATION: Fv region

<400> SEQUENCE: 12

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Arg Val His Ala Lys
                20                  25                  30

Tyr Phe Ala Trp Tyr Gln His Lys Pro Gly Gln Pro Arg Leu Leu
            35                  40                  45

Ile Tyr Gly Gly Ser Thr Arg Ala Thr Gly Ile Pro Asn Arg Phe Ser
    50                  55                  60

Ala Gly Gly Ser Gly Thr Gln Phe Thr Leu Thr Val Asn Arg Leu Glu
65                  70                  75                  80

Ala Glu Asp Phe Ala Val Tyr Tyr Cys Gln Gln Tyr Gly Ser Ser Pro
                85                  90                  95

Tyr Thr Phe Gly Gln Gly Thr Lys Val Glu Ile Arg
            100                 105
```

<210> SEQ ID NO 13
<211> LENGTH: 133
<212> TYPE: PRT
<213> ORGANISM: Artificial sequence
<220> FEATURE:
<223> OTHER INFORMATION: Fv region

<400> SEQUENCE: 13

Glu Val Gln Leu Val Glu Ser Gly Gly Gly Leu Ile Arg Pro Gly Gly
1               5                   10                  15

Ser Leu Arg Leu Ser Cys Lys Gly Ser Gly Phe Ile Phe Glu Asn Phe
            20                  25                  30

Gly Phe Gly Trp Val Arg Gln Gly Pro Gly Lys Gly Leu Glu Trp Val
        35                  40                  45

Ser Gly Thr Asn Trp Asn Gly Asp Ser Arg Tyr Gly Asp Ser Val
    50                  55                  60

Lys Gly Arg Phe Thr Ile Ser Arg Asp Asn Ser Asn Asn Phe Val Tyr
65                  70                  75                  80

Leu Gln Met Asn Ser Leu Arg Pro Glu Asp Thr Ala Ile Tyr Tyr Cys
                85                  90                  95

Ala Arg Gly Thr Asp Tyr Thr Ile Asp Glu Thr Gly Glu Arg Ala Gln
            100                 105                 110

Gly Ser Gly Thr Phe Trp Tyr Phe Asp Val Trp Gly Arg Gly Thr Leu
        115                 120                 125

Val Thr Val Ser Ser
    130

<210> SEQ ID NO 14
<211> LENGTH: 108
<212> TYPE: PRT
<213> ORGANISM: Artificial sequence
<220> FEATURE:
<223> OTHER INFORMATION: Fv region

<400> SEQUENCE: 14

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Asn Val His Pro Arg
            20                  25                  30

Tyr Phe Ala Trp Tyr Gln Gln Lys Arg Gly Gln Ser Pro Arg Leu Leu
        35                  40                  45

Ile His Ser Gly Ser Thr Arg Ala Ala Gly Ile Ala Asp Arg Phe Ser
    50                  55                  60

Gly Gly Gly Ser Gly Met His Phe Thr Leu Thr Ile Thr Arg Val Glu
65                  70                  75                  80

Pro Glu Asp Phe Ala Val Tyr Phe Cys Gln Gln Tyr Gly Gly Ser Pro
                85                  90                  95

Tyr Thr Phe Gly Gln Gly Thr Arg Val Glu Leu Arg
            100                 105

<210> SEQ ID NO 15
<211> LENGTH: 133
<212> TYPE: PRT
<213> ORGANISM: Artificial sequence
<220> FEATURE:
<223> OTHER INFORMATION: Fv region

<400> SEQUENCE: 15

-continued

Glu Val Gln Leu Val Glu Ser Gly Gly Gly Leu Ile Arg Pro Gly Gly
1               5                   10                  15

Ser Leu Arg Leu Ser Cys Lys Gly Ser Gly Phe Ile Phe Glu Asn Phe
            20                  25                  30

Gly Phe Gly Trp Val Arg Gln Gly Pro Gly Lys Gly Leu Glu Trp Val
        35                  40                  45

Ser Gly Thr Asn Trp Asn Gly Gly Asp Ser Gln Tyr Gly Asp Ser Val
    50                  55                  60

Lys Gly Arg Phe Thr Ile Ser Arg Asp Asn Ser Asn Asn Phe Val Tyr
65                  70                  75                  80

Leu Gln Met Asn Ser Leu Arg Pro Glu Asp Thr Ala Ile Tyr Tyr Cys
                85                  90                  95

Ala Arg Gly Thr Asp Tyr Thr Ile Asp Glu Thr Gly Glu Arg Ala Gln
            100                 105                 110

Gly Ser Gly Thr Phe Trp Tyr Phe Asp Val Trp Gly Arg Gly Thr Leu
        115                 120                 125

Val Thr Val Ser Ser
    130

<210> SEQ ID NO 16
<211> LENGTH: 108
<212> TYPE: PRT
<213> ORGANISM: Artificial sequence
<220> FEATURE:
<223> OTHER INFORMATION: Fv region

<400> SEQUENCE: 16

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Asn Val His Pro Arg
            20                  25                  30

Tyr Phe Ala Trp Tyr Gln Gln Lys Arg Gly Gln Ser Pro Arg Leu Leu
        35                  40                  45

Ile His Ser Gly Ser Thr Arg Ala Ala Gly Ile Ala Asp Arg Phe Ser
    50                  55                  60

Gly Gly Gly Ser Gly Met His Phe Thr Leu Thr Ile Thr Arg Val Glu
65                  70                  75                  80

Pro Glu Asp Phe Ala Val Tyr Phe Cys Gln Gln Tyr Gly Gly Ser Pro
                85                  90                  95

Tyr Thr Phe Gly Gln Gly Thr Arg Val Glu Leu Arg
            100                 105

<210> SEQ ID NO 17
<211> LENGTH: 120
<212> TYPE: PRT
<213> ORGANISM: Artificial sequence
<220> FEATURE:
<223> OTHER INFORMATION: Fv region

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ala Ala Ala Tyr
            20                  25                  30

Ala Ile Asn Trp Val Arg Gln Ala Pro Gly Gln Gly Leu Glu Trp Met
        35                  40                  45

Gly Asn Ile Glu Pro Glu Thr Gly Glu Ala Asn Tyr Ala Gln Lys Phe
    50                  55                  60

```
Ala Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Met Ser Tyr Lys His Leu Ser Asp Tyr Trp Gly Gln
            100                 105                 110

Gly Thr Leu Val Thr Val Ser Ser
        115                 120

<210> SEQ ID NO 18
<211> LENGTH: 111
<212> TYPE: PRT
<213> ORGANISM: Artificial sequence
<220> FEATURE:
<223> OTHER INFORMATION: Fv region

<400> SEQUENCE: 18

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Asn
                20                  25                  30

Asn Tyr Val Ser Trp Tyr Gln Gln His Pro Gly Lys Ala Pro Lys Leu
            35                  40                  45

Met Ile Tyr Gly Gly Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Arg Ser Trp Asp Ser Ala
                85                  90                  95

Ala Ala Tyr Ser Val Phe Gly Gly Gly Thr Lys Leu Thr Val Leu
            100                 105                 110

<210> SEQ ID NO 19
<211> LENGTH: 120
<212> TYPE: PRT
<213> ORGANISM: Artificial sequence
<220> FEATURE:
<223> OTHER INFORMATION: Fv region

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ala Ala Ala Tyr
                20                  25                  30

Ala Ile Asn Trp Val Arg Gln Ala Pro Gly Gln Gly Leu Glu Trp Met
            35                  40                  45

Gly Asn Ile Glu Pro Glu Thr Gly Glu Ala Ile Tyr Ala Gln Lys Phe
    50                  55                  60

Ala Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Met Ser Tyr Lys His Leu Ser Asp Tyr Trp Gly Gln
            100                 105                 110

Gly Thr Leu Val Thr Val Ser Ser
        115                 120
```

-continued

```
<210> SEQ ID NO 20
<211> LENGTH: 111
<212> TYPE: PRT
<213> ORGANISM: Artificial sequence
<220> FEATURE:
<223> OTHER INFORMATION: Fv region

<400> SEQUENCE: 20

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Asn
            20                  25                  30

Asn Tyr Val Ser Trp Tyr Gln Gln His Pro Gly Lys Ala Pro Lys Leu
        35                  40                  45

Met Ile Tyr Gly Gly Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Arg Ser Trp Asp Ser Ala
                85                  90                  95

Ala Ala Tyr Ser Val Phe Gly Gly Gly Thr Lys Leu Thr Val Leu
            100                 105                 110

<210> SEQ ID NO 21
<211> LENGTH: 119
<212> TYPE: PRT
<213> ORGANISM: Artificial sequence
<220> FEATURE:
<223> OTHER INFORMATION: Fv region

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Ala Pro Arg Val Asp Leu Tyr Ala Ala Asp Ala Trp Gly Gln Gly
            100                 105                 110

Thr Leu Val Thr Val Ser Ser
        115

<210> SEQ ID NO 22
<211> LENGTH: 122
<212> TYPE: PRT
<213> ORGANISM: Artificial sequence
<220> FEATURE:
<223> OTHER INFORMATION: Fv region

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30
```

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Arg Ala Ala Ala Lys Asp Trp Gly Val Ala Ala Tyr Trp
                100                 105                 110

Gly Gln Gly Thr Leu Val Thr Val Ser Ser
        115                 120

<210> SEQ ID NO 23
<211> LENGTH: 119
<212> TYPE: PRT
<213> ORGANISM: Artificial sequence
<220> FEATURE:
<223> OTHER INFORMATION: Fv region

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Leu Leu Trp Ser Trp Gly Gly Ala Gly Ser Trp Gly Gln Gly
                100                 105                 110

Thr Leu Val Thr Val Ser Ser
        115

<210> SEQ ID NO 24
<211> LENGTH: 121
<212> TYPE: PRT
<213> ORGANISM: Artificial sequence
<220> FEATURE:
<223> OTHER INFORMATION: Fv region

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
                    85                  90                  95
Ala Arg Ala Tyr Ala Gly Asp Gly Val Tyr Tyr Ala Asp Val Trp Gly
                100                 105                 110

Gln Gly Thr Leu Val Thr Val Ser Ser
        115                 120

<210> SEQ ID NO 25
<211> LENGTH: 120
<212> TYPE: PRT
<213> ORGANISM: Artificial sequence
<220> FEATURE:
<223> OTHER INFORMATION: Fv region

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Gly Tyr Glu Pro Tyr Met Ala Met Asp Tyr Trp Gly Gln
                100                 105                 110

Gly Thr Leu Val Thr Val Ser Ser
        115                 120

<210> SEQ ID NO 26
<211> LENGTH: 118
<212> TYPE: PRT
<213> ORGANISM: Artificial sequence
<220> FEATURE:
<223> OTHER INFORMATION: Fv region

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Met Pro Ala Trp Gly Ser Ala Asp Tyr Trp Gly Gln Gly Thr
                100                 105                 110

Leu Val Thr Val Ser Ser
        115

<210> SEQ ID NO 27
<211> LENGTH: 121
```

```
<212> TYPE: PRT
<213> ORGANISM: Artificial sequence
<220> FEATURE:
<223> OTHER INFORMATION: Fv region

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ala Ala Ser Asp Ala Ala Tyr Ala Ala Asn Val Trp Gly
            100                 105                 110

Gln Gly Thr Leu Val Thr Val Ser Ser
        115                 120

<210> SEQ ID NO 28
<211> LENGTH: 120
<212> TYPE: PRT
<213> ORGANISM: Artificial sequence
<220> FEATURE:
<223> OTHER INFORMATION: Fv region

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Glu Trp Phe Tyr Gly Ala Leu Ser Asp Tyr Ala Gly Gln
            100                 105                 110

Gly Thr Leu Val Thr Val Ser Ser
        115                 120

<210> SEQ ID NO 29
<211> LENGTH: 121
<212> TYPE: PRT
<213> ORGANISM: Artificial sequence
<220> FEATURE:
<223> OTHER INFORMATION: Fv region

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
```

```
            20                  25                  30
Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Thr Ala Ser Asp Gly Arg Ala Ala Met Asp Tyr Trp Gly
            100                 105                 110

Gln Gly Thr Leu Val Thr Val Ser Ser
        115                 120

<210> SEQ ID NO 30
<211> LENGTH: 118
<212> TYPE: PRT
<213> ORGANISM: Artificial sequence
<220> FEATURE:
<223> OTHER INFORMATION: Fv region

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Gly Gln Tyr Gly Asp Ala Thr Asp Tyr Trp Gly Gln Gly Thr
            100                 105                 110

Leu Val Thr Val Ser Ser
        115

<210> SEQ ID NO 31
<211> LENGTH: 120
<212> TYPE: PRT
<213> ORGANISM: Artificial sequence
<220> FEATURE:
<223> OTHER INFORMATION: Fv region

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Arg Gly Asp Tyr Gly Ser Trp Ser Phe Ala Tyr Trp Gly Gln
            100                 105                 110

Gly Thr Leu Val Thr Val Ser Ser
        115                 120

<210> SEQ ID NO 32
<211> LENGTH: 124
<212> TYPE: PRT
<213> ORGANISM: Artificial sequence
<220> FEATURE:
<223> OTHER INFORMATION: Fv region

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Trp Gly Ala Asn Ala Gly Gly Gly Met Asp
            100                 105                 110

Val Trp Gly Gln Gly Thr Leu Val Thr Val Ser Ser
        115                 120

<210> SEQ ID NO 33
<211> LENGTH: 118
<212> TYPE: PRT
<213> ORGANISM: Artificial sequence
<220> FEATURE:
<223> OTHER INFORMATION: Fv region

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Arg Ala Glu Tyr Ala Ser Asp Ala Trp Gly Gln Gly Thr
            100                 105                 110

Leu Val Thr Val Ser Ser
        115

<210> SEQ ID NO 34
```

```
<211> LENGTH: 120
<212> TYPE: PRT
<213> ORGANISM: Artificial sequence
<220> FEATURE:
<223> OTHER INFORMATION: Fv region

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Glu Ser Gly Asn Val Ala Ala Asp Tyr Trp Gly Gln
            100                 105                 110

Gly Thr Leu Val Thr Val Ser Ser
        115                 120

<210> SEQ ID NO 35
<211> LENGTH: 120
<212> TYPE: PRT
<213> ORGANISM: Artificial sequence
<220> FEATURE:
<223> OTHER INFORMATION: Fv region

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Cys Arg Ala Ala Ser Ala Tyr Ala Ala Asp Ala Ala Gly Gln
            100                 105                 110

Gly Thr Leu Val Thr Val Ser Ser
        115                 120

<210> SEQ ID NO 36
<211> LENGTH: 117
<212> TYPE: PRT
<213> ORGANISM: Artificial sequence
<220> FEATURE:
<223> OTHER INFORMATION: Fv region

<400> SEQUENCE: 36

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
            35                  40                  45

Ala Ser Ile Asp Pro Glu Thr Gly Glu Thr Leu Tyr Ala Lys Ser Val
        50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Ala His Ala Tyr Gly Leu Asp Tyr Trp Gly Gln Gly Thr Leu
            100                 105                 110

Val Thr Val Ser Ser
        115

<210> SEQ ID NO 37
<211> LENGTH: 119
<212> TYPE: PRT
<213> ORGANISM: Artificial sequence
<220> FEATURE:
<223> OTHER INFORMATION: Fv region

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
            35                  40                  45

Ala Ser Ile Asp Pro Glu Thr Gly Glu Thr Leu Tyr Ala Lys Ser Val
        50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Lys Trp Trp Ala Tyr Phe Asp Ala Trp Gly Gln Gly
            100                 105                 110

Thr Leu Val Thr Val Ser Ser
        115

<210> SEQ ID NO 38
<211> LENGTH: 120
<212> TYPE: PRT
<213> ORGANISM: Artificial sequence
<220> FEATURE:
<223> OTHER INFORMATION: Fv region

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
            35                  40                  45

Ala Ser Ile Asp Pro Glu Thr Gly Glu Thr Leu Tyr Ala Lys Ser Val
        50                  55                  60

Ala Gly Arg Phe Thr Ile Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                85                  90                  95

Ala Arg Asp Asn Gly Arg Ala Arg Ala Thr Ala Ala Tyr Ala Gly Gln
            100                 105                 110

Gly Thr Leu Val Thr Val Ser Ser
        115                 120

<210> SEQ ID NO 39
<211> LENGTH: 120
<212> TYPE: PRT
<213> ORGANISM: Artificial sequence
<220> FEATURE:
<223> OTHER INFORMATION: Fv region

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Lys Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Tyr Ala Trp Trp Tyr Ala Ala Ala Asp Tyr Trp Gly Gln
            100                 105                 110

Gly Thr Leu Val Thr Val Ser Ser
        115                 120

<210> SEQ ID NO 40
<211> LENGTH: 296
<212> TYPE: PRT
<213> ORGANISM: Artificial sequence
<220> FEATURE:
<223> OTHER INFORMATION: Keap1 construct used for crystallisation

<400> SEQUENCE: 40

Gly Ser Met Gly His Ala Pro Lys Val Gly Arg Leu Ile Tyr Thr Ala
1               5                   10                  15

Gly Gly Tyr Phe Arg Gln Ser Leu Ser Tyr Leu Glu Ala Tyr Asn Pro
            20                  25                  30

Ser Asp Gly Thr Trp Leu Asp Leu Ala Asp Leu Gln Val Pro Arg Ser
        35                  40                  45

Gly Leu Ala Gly Cys Val Val Gly Gly Leu Leu Tyr Ala Val Gly Gly
    50                  55                  60

Arg Asn Asn Ser Pro Asp Gly Asn Thr Asp Ser Ser Ala Leu Asp Cys
65                  70                  75                  80

Tyr Asn Pro Met Thr Asn Gln Trp Ser Pro Cys Ala Pro Met Ser Val
                85                  90                  95

Pro Arg Asn Arg Ile Gly Val Gly Val Ile Asp Gly His Ile Tyr Ala
            100                 105                 110

Val Gly Gly Ser His Gly Cys Ile His His Asn Ser Val Glu Arg Tyr
        115                 120                 125

Glu Pro Glu Arg Asp Glu Trp His Leu Val Ala Pro Met Leu Thr Arg
```

```
                130             135             140
Arg Ile Gly Val Gly Val Ala Val Leu Asn Arg Leu Leu Tyr Ala Val
145                 150                 155                 160

Gly Gly Phe Asp Gly Thr Asn Arg Leu Asn Ser Ala Glu Cys Tyr Tyr
                165                 170                 175

Pro Glu Arg Asn Glu Trp Arg Met Ile Thr Ala Met Asn Thr Ile Arg
                180                 185                 190

Ser Gly Ala Gly Val Cys Val Leu His Asn Cys Ile Tyr Ala Ala Gly
                195                 200                 205

Gly Tyr Asp Gly Gln Asp Gln Leu Asn Ser Val Glu Arg Tyr Asp Val
                210                 215                 220

Glu Thr Glu Thr Trp Thr Phe Val Ala Pro Met Lys His Arg Arg Ser
225                 230                 235                 240

Ala Leu Gly Ile Thr Val His Gln Gly Arg Ile Tyr Val Leu Gly Gly
                245                 250                 255

Tyr Asp Gly His Thr Phe Leu Asp Ser Val Glu Cys Tyr Asp Pro Asp
                260                 265                 270

Thr Asp Thr Trp Ser Glu Val Thr Arg Met Thr Ser Gly Arg Ser Gly
                275                 280                 285

Val Gly Val Ala Val Thr Met Glu
                290                 295

<210> SEQ ID NO 41
<211> LENGTH: 267
<212> TYPE: PRT
<213> ORGANISM: Artificial sequence
<220> FEATURE:
<223> OTHER INFORMATION: LS146-scFv construct used for crystallisation

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
                20                  25                  30

Ser Ile His Trp Val Arg Gln Ala Pro Gly Lys Cys Leu Glu Trp Val
                35                  40                  45

Ala Ser Ile Asp Pro Glu Thr Gly Glu Thr Leu Tyr Ala Lys Ser Val
                50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala Tyr Ala Gly Asp Gly Val Tyr Tyr Ala Asp Val Trp Gly
                100                 105                 110

Gln Gly Thr Leu Val Thr Val Ser Ser Gly Gly Gly Ser Gly Gly
                115                 120                 125

Gly Gly Ser Gly Gly Gly Ser Gly Gly Gly Ser Asp Ile Gln
                130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Val Ser Ser Ala Val Ala Trp
                165                 170                 175

Tyr Gln Gln Lys Pro Gly Lys Ala Pro Lys Leu Leu Ile Tyr Ser Ala
                180                 185                 190

Ser Ser Leu Tyr Ser Gly Val Pro Ser Arg Phe Ser Gly Ser Arg Ser
```

```
                195                 200                 205
Gly Thr Asp Phe Thr Leu Thr Ile Ser Ser Leu Gln Pro Glu Asp Phe
            210                 215                 220

Ala Thr Tyr Tyr Cys Gln Gln Ser Tyr Ser Phe Pro Ser Thr Phe Gly
225                 230                 235                 240

Cys Gly Thr Lys Val Glu Ile Lys Arg Thr Glu Asn Leu Tyr Phe Gln
            245                 250                 255

Gly His His His His His His His His His
            260                 265

<210> SEQ ID NO 42
<211> LENGTH: 116
<212> TYPE: PRT
<213> ORGANISM: Artificial sequence
<220> FEATURE:
<223> OTHER INFORMATION: Fv region

<400> SEQUENCE: 42

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Ile Ala Glu
            20                  25                  30

Met Leu His Trp Val Lys Gln Ser His Ala Glu Ser Leu Glu Trp Ile
        35                  40                  45

Gly Leu Ile Ile Pro Ala Val Gly Ile Thr Tyr Tyr Asn Gln Lys Phe
    50                  55                  60

Lys Asp Lys Ala Thr Met Thr Val Asp Ile Ala Ser Ser Thr Ala Tyr
65                  70                  75                  80

Leu Glu Leu Ala Arg Leu Thr Ser Glu Asp Ser Ala Ile Tyr Tyr Cys
                85                  90                  95

Ala Arg Ser Trp Ala Glu Gly Leu Phe Phe Asp Tyr Trp Gly Gln Gly
            100                 105                 110

Thr Leu Val Thr
        115

<210> SEQ ID NO 43
<211> LENGTH: 110
<212> TYPE: PRT
<213> ORGANISM: Artificial sequence
<220> FEATURE:
<223> OTHER INFORMATION: Fv region

<400> SEQUENCE: 43

Asp Ile Val Met Thr Gln Thr Pro Lys Phe Leu Leu Val Ser Ala Gly
1               5                   10                  15

Asp Lys Val Thr Ile Thr Cys Lys Ala Ser Gln Ser Val Ser Asn Ala
            20                  25                  30

Leu Thr Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Gly Ala Pro Pro
                85                  90                  95

Thr Phe Gly Gly Gly Thr Lys Val Glu Ile Lys Arg Thr Val
            100                 105                 110
```

<210> SEQ ID NO 44
<211> LENGTH: 118
<212> TYPE: PRT
<213> ORGANISM: Artificial sequence
<220> FEATURE:
<223> OTHER INFORMATION: Fv region

<400> SEQUENCE: 44

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ala Tyr
                20                  25                  30

Trp Ile Ser Trp Val Arg Gln Met Pro Gly Lys Gly Leu Glu Trp Met
            35                  40                  45

Gly Arg Ile Ile Pro Ser Val Ser Ile Thr Asn Tyr Ser Pro Ser Phe
    50                  55                  60

Gln Gly His Val Thr Ile Ser Ala Asp Lys Ala Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Leu Met Gln Gly Ala Met Leu Thr Phe Asp Ser Trp Gly
                100                 105                 110

Gln Gly Thr Leu Val Thr
            115
```

<210> SEQ ID NO 45
<211> LENGTH: 110
<212> TYPE: PRT
<213> ORGANISM: Artificial sequence
<220> FEATURE:
<223> OTHER INFORMATION: Fv region

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Leu Ala
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Ser Tyr
                85                  90                  95

Thr Phe Gly Gln Gly Thr Lys Val Glu Ile Lys Arg Thr Val
                100                 105                 110
```

<210> SEQ ID NO 46
<211> LENGTH: 120
<212> TYPE: PRT
<213> ORGANISM: Artificial sequence
<220> FEATURE:
<223> OTHER INFORMATION: Fv region

<400> SEQUENCE: 46

```
Glu Val Gln Leu Val Glu Ser Gly Gly Gly Leu Val Lys Ala Gly Gly
1               5                   10                  15

Ser Leu Ile Leu Ser Cys Gly Val Ser Asn Phe Arg Ile Ala Tyr His
```

```
              20                  25                  30
Ile Met Asn Trp Val Arg Arg Val Pro Gly Gly Gly Leu Glu Trp Val
            35                  40                  45

Ala Ser Ile Val Thr Ile Asp Ala Ala Thr Tyr Ala Asp Ala Val
    50                  55                  60

Lys Gly Arg Phe Thr Val Ser Arg Asp Asp Ala Ser Asp Phe Val Tyr
65                  70                  75                  80

Leu Gln Met His Lys Met Arg Val Glu Asp Thr Ala Ile Tyr Tyr Cys
                85                  90                  95

Ala Arg Lys Gly Ser Asp Val Thr Gln Asp Asn Asp Pro Phe Asp Ala
            100                 105                 110

Trp Gly Pro Gly Thr Val Val Thr
            115                 120

<210> SEQ ID NO 47
<211> LENGTH: 110
<212> TYPE: PRT
<213> ORGANISM: Artificial sequence
<220> FEATURE:
<223> OTHER INFORMATION: Fv region

<400> SEQUENCE: 47

Asp Val Val Met Thr Gln Ser Pro Ser Thr Leu Ser Ala Ser Val Gly
1               5                   10                  15

Asp Thr Ile Thr Ile Thr Cys Arg Ala Ser Ser Gly Gly Gly Thr Trp
            20                  25                  30

Leu Ala Trp Tyr Gln Gln Lys Pro Gly Lys Ala Pro Lys Leu Leu Ile
            35                  40                  45

Tyr Lys Ala Ser Thr Leu Lys Thr Gly Val Pro Ser Arg Phe Ser Gly
    50                  55                  60

Ser Gly Ser Gly Thr Glu Phe Thr Leu Thr Ile Ser Gly Leu Gln Phe
65                  70                  75                  80

Asp Asp Phe Ala Thr Tyr His Cys Gln His Tyr Ser Leu Val Tyr Ala
                85                  90                  95

Thr Phe Gly Gln Gly Thr Arg Val Glu Ile Lys Arg Thr Val
            100                 105                 110

<210> SEQ ID NO 48
<211> LENGTH: 122
<212> TYPE: PRT
<213> ORGANISM: Artificial sequence
<220> FEATURE:
<223> OTHER INFORMATION: VH

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Tyr Ile Ser Tyr Ser
            20                  25                  30

Ser Ile His Trp Val Arg Gln Ala Pro Gly Lys Gly Leu Glu Trp Val
            35                  40                  45

Ala Ser Ile Ser Pro Tyr Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Gln Gly Tyr Arg Arg Ser Gly Arg Gly Phe Asp Tyr Trp
            100                 105                 110

Gly Gln Gly Thr Leu Val Thr Val Ser Ser
        115                 120

<210> SEQ ID NO 49
<211> LENGTH: 122
<212> TYPE: PRT
<213> ORGANISM: Artificial sequence
<220> FEATURE:
<223> OTHER INFORMATION: VH

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Ser Pro Glu Thr Gly Glu Thr Tyr Tyr Ala Asp Ser Val
    50                  55                  60

Ala Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Ala Ala Arg Ser Gly Arg Gly Phe Asp Tyr Trp
            100                 105                 110

Gly Gln Gly Thr Leu Val Thr Val Ser Ser
        115                 120

<210> SEQ ID NO 50
<211> LENGTH: 122
<212> TYPE: PRT
<213> ORGANISM: Artificial sequence
<220> FEATURE:
<223> OTHER INFORMATION: VH

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Ser Ala Ser
            20                  25                  30

Ser Ile His Trp Val Arg Gln Ala Pro Gly Lys Gly Leu Glu Trp Val
        35                  40                  45

Ala Ser Ile Asp Pro Glu Thr Gly Glu Thr Leu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Gly Tyr Ala Ala Arg Ser Gly Arg Gly Phe Asp Tyr Trp
            100                 105                 110

Gly Gln Gly Thr Leu Val Thr Val Ser Ser
        115                 120

<210> SEQ ID NO 51
<211> LENGTH: 120
<212> TYPE: PRT
<213> ORGANISM: Artificial sequence

<220> FEATURE:
<223> OTHER INFORMATION: VH

<400> SEQUENCE: 51

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Asn Trp Val Arg Gln Ala Pro Gly Gln Gly Leu Glu Trp Met
        35                  40                  45

Gly Asn Ile Glu Pro Tyr Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Met Ser Tyr Lys His Leu Ser Asp Tyr Trp Gly Gln
            100                 105                 110

Gly Thr Leu Val Thr Val Ser Ser
        115                 120
```

<210> SEQ ID NO 52
<211> LENGTH: 120
<212> TYPE: PRT
<213> ORGANISM: Artificial sequence
<220> FEATURE:
<223> OTHER INFORMATION: VH

<400> SEQUENCE: 52

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ala Ala Ala Tyr
            20                  25                  30

Ala Ile Asn Trp Val Arg Gln Ala Pro Gly Gln Gly Leu Glu Trp Met
        35                  40                  45

Gly Asn Ile Glu Pro Glu Thr Gly Glu Ala Asn Tyr Ala Gln Lys Phe
50                  55                  60

Ala Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Met Ser Tyr Lys His Leu Ser Asp Tyr Trp Gly Gln
            100                 105                 110

Gly Thr Leu Val Thr Val Ser Ser
        115                 120
```

<210> SEQ ID NO 53
<211> LENGTH: 120
<212> TYPE: PRT
<213> ORGANISM: Artificial sequence
<220> FEATURE:
<223> OTHER INFORMATION: VH

<400> SEQUENCE: 53

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ala Ala Ala Tyr
            20                  25                  30
```

Ala Ile Asn Trp Val Arg Gln Ala Pro Gly Gln Gly Leu Glu Trp Met
         35                  40                  45

Gly Asn Ile Glu Pro Glu Thr Gly Glu Ala Ile Tyr Ala Gln Lys Phe
 50                  55                  60

Ala Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Met Ser Tyr Lys His Leu Ser Asp Tyr Trp Gly Gln
            100                 105                 110

Gly Thr Leu Val Thr Val Ser Ser
        115                 120

<210> SEQ ID NO 54
<211> LENGTH: 29
<212> TYPE: PRT
<213> ORGANISM: Artificial sequence
<220> FEATURE:
<223> OTHER INFORMATION: Loop swap

<400> SEQUENCE: 54

Thr Ala Val Tyr Tyr Cys Ala Ile Leu Gly Ala Trp Gly Ala Asn Ala
 1               5                  10                  15

Gly Gly Gly Gly Met Asp Val Trp Gly Gln Gly Thr Leu
            20                  25

<210> SEQ ID NO 55
<211> LENGTH: 27
<212> TYPE: PRT
<213> ORGANISM: Artificial sequence
<220> FEATURE:
<223> OTHER INFORMATION: Loop swap

<400> SEQUENCE: 55

Thr Ala Val Tyr Tyr Cys Ala Arg Gln Gly Tyr Ala Ala Arg Ser Gly
 1               5                  10                  15

Ala Gly Phe Asp Tyr Trp Gly Gln Gly Thr Leu
            20                  25

<210> SEQ ID NO 56
<211> LENGTH: 27
<212> TYPE: PRT
<213> ORGANISM: Artificial sequence
<220> FEATURE:
<223> OTHER INFORMATION: Loop swap

<400> SEQUENCE: 56

Thr Ala Val Tyr Tyr Cys Val Arg Arg Ala Ala Lys Asp Trp Gly
 1               5                  10                  15

Val Ala Ala Ala Tyr Trp Gly Gln Gly Thr Leu
            20                  25

<210> SEQ ID NO 57
<211> LENGTH: 26
<212> TYPE: PRT
<213> ORGANISM: Artificial sequence
<220> FEATURE:
<223> OTHER INFORMATION: Loop swap

<400> SEQUENCE: 57

Thr Ala Val Tyr Tyr Cys Ala Arg Arg Thr Ala Ser Asp Gly Arg Ala
 1               5                  10                  15

Ala Met Asp Tyr Trp Gly Gln Gly Thr Leu
            20                  25

<210> SEQ ID NO 58
<211> LENGTH: 26
<212> TYPE: PRT
<213> ORGANISM: Artificial sequence
<220> FEATURE:
<223> OTHER INFORMATION: Loop swap

<400> SEQUENCE: 58

Thr Ala Val Tyr Tyr Cys Ala Arg Ser Ala Ala Ser Asp Ala Ala Tyr
1               5                   10                  15

Ala Ala Asn Val Trp Gly Gln Gly Thr Leu
            20                  25

<210> SEQ ID NO 59
<211> LENGTH: 26
<212> TYPE: PRT
<213> ORGANISM: Artificial sequence
<220> FEATURE:
<223> OTHER INFORMATION: Loop swap

<400> SEQUENCE: 59

Thr Ala Val Tyr Tyr Cys Ala Arg Ala Tyr Ala Gly Asp Gly Val Tyr
1               5                   10                  15

Tyr Ala Asp Val Trp Gly Gln Gly Thr Leu
            20                  25

<210> SEQ ID NO 60
<211> LENGTH: 25
<212> TYPE: PRT
<213> ORGANISM: Artificial sequence
<220> FEATURE:
<223> OTHER INFORMATION: Loop swap

<400> SEQUENCE: 60

Thr Ala Val Tyr Tyr Cys Ala Arg Trp Gly Tyr Glu Pro Tyr Met Ala
1               5                   10                  15

Met Asp Tyr Trp Gly Gln Gly Thr Leu
            20                  25

<210> SEQ ID NO 61
<211> LENGTH: 25
<212> TYPE: PRT
<213> ORGANISM: Artificial sequence
<220> FEATURE:
<223> OTHER INFORMATION: Loop swap

<400> SEQUENCE: 61

Thr Ala Cys Tyr Tyr Cys Ala Arg Glu Tyr Ala Trp Trp Tyr Ala Ala
1               5                   10                  15

Ala Asp Tyr Trp Gly Gln Gly Thr Leu
            20                  25

<210> SEQ ID NO 62
<211> LENGTH: 25
<212> TYPE: PRT
<213> ORGANISM: Artificial sequence
<220> FEATURE:
<223> OTHER INFORMATION: Loop swap

<400> SEQUENCE: 62

Thr Ala Val Tyr Tyr Cys Ala Arg Ala Glu Ser Gly Asn Val Ala Ala
1               5                   10                  15

Ala Asp Tyr Trp Gly Gln Gly Thr Leu
            20                  25

<210> SEQ ID NO 63
<211> LENGTH: 25
<212> TYPE: PRT
<213> ORGANISM: Artificial sequence
<220> FEATURE:
<223> OTHER INFORMATION: Loop swap

<400> SEQUENCE: 63

Thr Ala Val Tyr Tyr Cys Ala Arg Gly Glu Trp Phe Tyr Gly Ala Leu
1               5                   10                  15

Ser Asp Tyr Ala Gly Gln Gly Thr Leu
            20                  25

<210> SEQ ID NO 64
<211> LENGTH: 25
<212> TYPE: PRT
<213> ORGANISM: Artificial sequence
<220> FEATURE:
<223> OTHER INFORMATION: Loop swap

<400> SEQUENCE: 64

Thr Ala Val Tyr Tyr Cys Ala Arg Asp Asn Gly Arg Ala Arg Ala Thr
1               5                   10                  15

Ala Ala Tyr Ala Gly Gln Gly Thr Leu
            20                  25

<210> SEQ ID NO 65
<211> LENGTH: 25
<212> TYPE: PRT
<213> ORGANISM: Artificial sequence
<220> FEATURE:
<223> OTHER INFORMATION: Loop swap

<400> SEQUENCE: 65

Thr Ala Val Tyr Tyr Cys Ala Arg Cys Arg Ala Ala Ser Ala Tyr Ala
1               5                   10                  15

Ala Asp Ala Ala Gly Gln Gly Thr Leu
            20                  25

<210> SEQ ID NO 66
<211> LENGTH: 25
<212> TYPE: PRT
<213> ORGANISM: Artificial sequence
<220> FEATURE:
<223> OTHER INFORMATION: Loop swap

<400> SEQUENCE: 66

Thr Ala Val Tyr Tyr Cys Ala Arg Arg Gly Asp Tyr Gly Ser Trp Ser
1               5                   10                  15

Phe Ala Tyr Trp Gly Gln Gly Thr Leu
            20                  25

<210> SEQ ID NO 67
<211> LENGTH: 24
<212> TYPE: PRT
<213> ORGANISM: Artificial sequence
<220> FEATURE:
<223> OTHER INFORMATION: Loop swap

<400> SEQUENCE: 67

Thr Ala Val Tyr Tyr Cys Ala Arg Glu Gly Lys Trp Trp Ala Tyr Phe

```
                1               5                   10                  15

Asp Ala Trp Gly Gln Gly Thr Leu
            20

<210> SEQ ID NO 68
<211> LENGTH: 24
<212> TYPE: PRT
<213> ORGANISM: Artificial sequence
<220> FEATURE:
<223> OTHER INFORMATION: Loop swap

<400> SEQUENCE: 68

Thr Ala Val Tyr Tyr Cys Val Ala Pro Arg Val Asp Leu Tyr Ala Ala
1               5                   10                  15

Asp Ala Trp Gly Gln Gly Thr Leu
            20

<210> SEQ ID NO 69
<211> LENGTH: 24
<212> TYPE: PRT
<213> ORGANISM: Artificial sequence
<220> FEATURE:
<223> OTHER INFORMATION: Loop swap

<400> SEQUENCE: 69

Thr Ala Val Tyr Tyr Cys Ala Gly Leu Leu Trp Ser Trp Gly Gly Ala
1               5                   10                  15

Gly Ser Trp Gly Gln Gly Thr Leu
            20

<210> SEQ ID NO 70
<211> LENGTH: 23
<212> TYPE: PRT
<213> ORGANISM: Artificial sequence
<220> FEATURE:
<223> OTHER INFORMATION: Loop swap

<400> SEQUENCE: 70

Thr Ala Val Tyr Tyr Cys Ser Arg Gly Gln Tyr Gly Asp Ala Thr Asp
1               5                   10                  15

Tyr Trp Gly Gln Gly Thr Leu
            20

<210> SEQ ID NO 71
<211> LENGTH: 23
<212> TYPE: PRT
<213> ORGANISM: Artificial sequence
<220> FEATURE:
<223> OTHER INFORMATION: Loop swap

<400> SEQUENCE: 71

Thr Ala Val Tyr Tyr Cys Ala Arg Glu Arg Ala Glu Tyr Ala Ser Asp
1               5                   10                  15

Ala Trp Gly Gln Gly Thr Leu
            20

<210> SEQ ID NO 72
<211> LENGTH: 23
<212> TYPE: PRT
<213> ORGANISM: Artificial sequence
<220> FEATURE:
<223> OTHER INFORMATION: Loop swap

<400> SEQUENCE: 72
```

```
Thr Ala Val Tyr Tyr Cys Ala Arg Met Pro Ala Trp Gly Ser Ala Asp
1               5                   10                  15

Tyr Trp Gly Gln Gly Thr Leu
                20

<210> SEQ ID NO 73
<211> LENGTH: 22
<212> TYPE: PRT
<213> ORGANISM: Artificial sequence
<220> FEATURE:
<223> OTHER INFORMATION: Loop swap

<400> SEQUENCE: 73

Thr Ala Val Tyr Tyr Cys Thr Arg Ala His Ala Tyr Gly Leu Asp Tyr
1               5                   10                  15

Trp Gly Gln Gly Thr Leu
                20

<210> SEQ ID NO 74
<211> LENGTH: 14
<212> TYPE: PRT
<213> ORGANISM: Artificial Sequence
<220> FEATURE:
<223> OTHER INFORMATION: Nrf2 peptide analogue
<220> FEATURE:
<221> NAME/KEY: MISC_FEATURE
<222> LOCATION: (1)..(1)
<223> OTHER INFORMATION: N-terminal biotin-PEG
<220> FEATURE:
<221> NAME/KEY: MISC_FEATURE
<222> LOCATION: (14)..(14)
<223> OTHER INFORMATION: C-terminal amide

<400> SEQUENCE: 74

Leu Gln Leu Asp Glu Glu Thr Gly Glu Phe Leu Pro Ile Gln
1               5                   10
```

DE NOVO ANTIBODY DESIGN

This application is a U.S. national phase application under 35 USC 371 of International Patent Application no. PCT/EP2016/079497, filed Dec. 1, 2016, which claims the benefit of Great Britain Application no. 1521447.1, filed Dec. 4, 2015.

The present invention relates to computational design of antibodies that will bind to a target epitope.

Targeting the correct epitope is a critical step in selection of a monoclonal antibody to achieve the desired mechanism of action. Current approaches for the discovery of novel antibodies for therapeutic and diagnostic use rely on raising antibodies against a target protein in immunised animals, or on in vitro screening of naïve or immunised libraries using display technologies. Neither method allows complete control over affinity, specificity, epitope and binding mode.

Sormanni et al. (Sormanni, P., Aprile, F. A., Vendruscolo, M. Rational design of antibodies targeting specific epitopes within intrinsically disordered proteins. *Proc. Natl. Acad. Sci. USA.* 112, 9902-9907 (2015)), Robinson et al. (Robinson, L. N., et al. Structure-guided design of an anti-dengue antibody directed to a non-immunodominant epitope. *Cell* 162, 493-504 (2015)), Lippow et al. (Lippow, S. M., Wittrup, K. D. & Tidor, B. Computational design of antibody-affinity improvement beyond in vivo maturation. *Nat. Biotechnol.* 25, 1171-1176 (2007)), and Kuroda et al. (Kuroda, D., Shirai, H., Jacobson, M. P. & Nakamura, H. Computer-aided antibody design. *Protein Eng. Des. Sel.*, 25, 507-521 (2012)) have demonstrated some success in attempts to engineer rationally antibodies but also that the computational design of antibodies targeting pre-selected epitopes on target proteins remains a challenging problem.

Computational antibody design has enabled rational engineering of antibodies to enhance affinity and stability by in silico scanning of interfacial CDR sequence spaces (see Lippow et al. above and Jordan et al. (Jordan, A. L., et al. Structural understanding of stabilization patterns in engineered bispecific Ig-like antibody molecules. *Proteins* 77, 832-841 (2009))). Recent development of general antibody design approaches like OptMAVEn (Li, T., Pantazes, R. J., Maranas, C. D. OptMAVEn—a new framework for the de novo design of antibody variable region models targeting specific antigen epitopes. *PLoS One.* 9, e105954 (2014)) and AbDesign (Lapidoth, G. D. et al. AbDesign: An algorithm for combinatorial backbone design guided by natural conformations and sequences. *Proteins* 83, 1385-1406 (2015)) are based on protein-protein docking to sample the possible binding poses of artificial antibody scaffolds, followed by the generation of combinatorial backbone configurations and sequence space scanning. However without ultimate proof of experimental validation of designed antibodies from these methods so far, the computational design of high-affinity antibodies targeting precise epitopes remains a largely unsolved problem. The development of computational methods for the design of antibodies binding with high affinity at pre-selected epitopes would have wide-ranging applications, such as achieving epitope-dependent mechanism of actions and accessing immunisation blind spots which are often biologically relevant, conserved orthosteric sites.

It is an object of the invention to provide an alternative framework for computational design of antibodies.

According to an aspect of the invention, there is provided a computer-implemented method of designing an antibody that will bind to a target epitope, comprising: a) identifying one or more hotspot residues that will each bind to a corresponding one of one or more hotspot sites on the target epitope, each hotspot residue comprising a hotspot sub-structure comprising one or more hotspot sub-structure characteristic atoms; b) selecting from a database of antibody structures one or more candidate antibody structures, each candidate antibody structure having one or more matching residues each comprising a matching residue sub-structure comprising one or more matching residue sub-structure characteristic atoms, wherein the selection is performed such that the relative positions of the matching residue sub-structure characteristic atoms within the antibody structure and the relative positions of the hotspot sub-structure characteristic atoms when bound to the target epitope are such that at least three of the matching residue sub-structure characteristic atoms can be superimposed computationally on a corresponding at least three hotspot sub-structure characteristic atoms with a spatial deviation between each pair of superimposed characteristic atoms averaged over all pairs being less than a predetermined threshold; and c) generating a designed antibody by modifying one of the candidate antibody structures, the modifying comprising replacing at least one of the matching residues with a different residue such that a predicted affinity between the designed antibody and the target epitope is higher than a predicted affinity between the candidate antibody structure and the target epitope or outputting one of the candidate antibody structures as a designed antibody structure in the case where each of the matching residues is already a residue of the same amino acid as the hotspot residue which the matching residue matches.

The present inventors have demonstrated that is possible based on the above framework to design novel antibodies binding at naturally occurring protein-binding sites, guided by pre-identified hotspot-mediated interactions. The novel computational approach offers the potential for structure-based rational design of novel antibodies with precise control of binding mode for therapeutic and diagnostic application.

The binding affinities of the designed antibodies are optionally further optimised by in silico swap and redesign of the CDR sequences. Exemplification has been achieved through computational design of antibodies with nanomolar-level binding affinities to Kelch-like ECH-associated protein 1 (Keap1) at the nuclear factor-like 2 (Nrf2) binding site. An X-ray co-crystal structure of one of the designed antibodies shows atomic-level agreement with the corresponding computational model, demonstrating successful application of an experimentally validated computational design of antibodies targeting a pre-selected epitope.

In an embodiment the selection of candidate antibody structures from the database is performed using a preselection based on matching distances between characteristic atoms, followed by a further selection based on determining whether at least three of the matching residue sub-structure characteristic atoms can be superimposed on the corresponding at least three hotspot sub-structure characteristic atoms with the spatial deviation between each pair of superimposed atoms averaged over all pairs being less than the predetermined threshold. This two step approach enables the candidate antibody structures to be selected from the database particularly efficiently. This increase in efficiency is expected to become increasingly important as available databases of antibody structures get larger.

In an embodiment the generating of the designed antibody further comprises iteratively swapping one or more CDR loops of the candidate antibody structure with CDR loops from a database of CDR loops to increase a predicted affinity between the candidate antibody structure and the target epitope. The inventors have found that this step advantageously provides additional conformational degrees of freedom which allows improved affinity to be achieved between the designed antibody and the target epitope. In the absence of this step the relatively limited number of antibody structures available from databases means that it can be challenging to find high-affinity antibodies bearing CDRs that form optimal shape/electrostatic complementarity to the selected epitope on target proteins. CDR loop swap leverages the large number of sequences and experimentally determined CDR configurations from other antibody structures to construct new chimeric antibody models. Combining CDR loop swap with the other steps of the invention allows fast generation of high affinity antibodies targeting the selected binding site.

Embodiments of the invention will now be described, by way of example only, with reference to the accompanying drawings in which corresponding reference symbols represent corresponding parts, and in which:

FIG. 1 depicts steps in an example method of designing an antibody that will bind to a target epitope;

FIG. 2 depicts example implementation of a step of selecting candidate antibody structures from a database;

FIG. 3 depicts a pre-selection process for multiple matching residues;

FIG. 4 depicts a schematic example geometry for calculating a first set of distances for three hotspot sub-structures;

FIG. 5 depicts a pre-selection process for a single matching residue;

FIG. 6 depicts a schematic example geometry for calculating a first set of distances in a hotspot sub-structure having three characteristic atoms involved in superimposition;

FIG. 7 depicts a schematic example geometry for calculating a first set of distances in a hotspot sub-structure having four characteristic atoms involved in superimposition;

FIG. 8 depicts an example procedure for determining when characteristic atoms superimpose with an average spatial deviation within the predetermined threshold;

FIG. 9 depicts an example procedure for refining a designed antibody where geometrical clashing is detected;

FIG. 10 depicts an example workflow of hotspots-guided antibody scaffold graft design in anti-Keap1 antibodies targeting Nrf2 binding site;

FIG. 11 depicts SPR kinetic profiles for G54.1/keap1 and G85/keap1 interaction, where titrations of keap1 are flowed over chip surfaces comprising immobilized anti-keap1 Fabs and where the Fab designs have been derived from grafted Nrf2 hotspots;

FIG. 12 depicts sequence alignments of the $V_H$ regions of two best hotspots graft designs, G54 (a) and G85 (b), with corresponding original PDB scaffold structures and variants from in silico mutagenesis. Residues labelled "M" represent amino acids that differ from the scaffolds after hotspots graft and alanine mutation to reduce the clashes. "G" indicates residues that are introduced during in silico mutagenesis to yield variants G54.1 and G85.1, respectively. The three Nrf2-inspired hotspots being grafted are marked with asterisks;

FIG. 13 depicts SPR kinetic profiles for G54.1/keap1 and G85/keap1 interaction, in the presence of competing titrations of the cognate high affinity Nrf2 peptide segment that interacts with the keap1 binding site, thus demonstrating specific binding of designed antibody to the Nrf2 binding site of keap1;

FIG. 14 depicts the modelled binding poses of designed antibodies G54.1 (Left) and G85 (Right) in complex with Keap1 in anti-Keap1 antibodies targeting Nrf2 binding site; three hotspot residues (depicted as sticks) backbones on CDRH2 loops and Nrf2 peptide are superimposed;

FIG. 15 depicts workflow of CDRH3 loop swap design in affinity improvement of G54.1 antibody;

FIG. 16 depicts CDR-loop-wise Rosetta ΔG scores decomposition of designed G54.1 antibody; the individual CDR loop's contributions to the Rosetta ΔG scores between G54.1 and Keap1 were estimated by truncating each CDR loop from the Fv fragment of modelled G54.1/Keap1 complex structure;

FIG. 17 depicts sequence alignment of CDRH3 loop in the CDRH3-swap variants of G54.1 in affinity improvement of G54.1 antibody by CDRH3 loop swap;

FIG. 18 depicts relative binding affinity improvements of designed CDRH3-swap variants over parental G54.1 Fab;

FIG. 19 depicts computationally modelled CDRH3 conformations and interaction modes of parental G54.1 and four highest affinity-improved CDRH3-swap designs with Keap1 in affinity improvement of G54.1 antibody by CDRH3 loop swap; key contact residues in CDRH3 loops are depicted as sticks;

FIG. 20 depicts close-ups of conformations and interaction modes of isolated modelled CDRH3 loops of four highest affinity-improved CDRH3-swap designs with Keap1: a, LS171; b, LS145; c, LS168; d, LS146; the conformations and interaction modes of CDRH3 (lighter grey) with Keap1 (darker grey) are show from top (Left) and side view (Right); the key contact residues in CDRH3 loops are depicted as sticks; it is clearly shown that $V_H$99L and $V_H$100Y in LS171, $V_H$97 W in LS168 and $V_H$97Y in LS146 occupy the interfacial void between antibodies and Keap1 that is not occupied by LS145 or G54.1 (see also FIG. 19 for comparison);

FIG. 21 depicts a crystal structure of LS146-scFv/Keap1 complex showing the precision of the computational design;

FIG. 22 depicts crystal packing in LS146-scFv/Keap1 complex; the asymmetric unit contains two copies of LS146-scFv/Keap1 complexes;

FIG. 23 depict grafted hotpots binding site $2F_o$-$F_c$ maps of LS146-scFv/Keap1 complex; $2F_o$-$F_c$ omit map electron densities (grey meshes, contoured at 1.0 σ) of grafted hotspots and other LS146-scFv CDRH2 residues interacting with Keap1 for the two molecules in the asymmetric unit; the crystal waters are shown as grey spheres;

FIG. 24 depicts a crystal structure of LS146-scFv/Keap1 complex confirming occupation of Nrf2 binding site in Keap1;

FIG. 25 depicts a crystal structure of LS146-scFv/Keap1 complex showing the precision of the computational design—close-up of LS146-scFv epitopes of CDRH2, with the key contact residues depicted as sticks, and hydrogen bonds depicted as dot lines;

FIG. 26 depicts a close-up of LS146-scFv epitopes which are mapped onto Keap1 molecular surface coloured in terms of contacting CDRs;

FIG. 27 depicts a crystal structure of LS146-scFv/Keap1 complex showing the precision of the computational design—close-up of LS146-scFv epitopes of CDRH3, with the key contact residues depicted as sticks, and hydrogen bonds depicted as dot lines;

FIG. 28 depicts a crystal structure of LS146-scFv/Keap1 complex showing the precision of the computational design—close-up of LS146-scFv epitopes of CDRH1, with the key contact residues depicted as sticks, and hydrogen bonds depicted as dot lines;

FIG. 29 depicts a crystal structure of LS146-scFv/Keap1 complex showing the precision of the computational design—close-up of LS146-scFv epitopes of $V_H$ framework 3 (FR3), with the key contact residues depicted as sticks, and hydrogen bonds depicted as dot lines;

FIG. 30 depicts a crystal structure of LS146-scFv/Keap1 complex showing the precision of the computational design—comparison of the binding modes of crystal LS146-scFv with modelled LS146-Fab by superimposing onto the Keap1 side;

FIG. 31 depicts a crystal structure of LS146-scFv/Keap1 complex showing the precision of the computational design—comparison of backbone conformations and side-chain orientations of CDRH2 loops (the hotspots acceptor) from crystal (Left) and modelled (Right) structures of LS146 Fv region; the key CDRH3 residues are depicted as sticks, and hydrogen bond that affects $V_H52$ D's conformation from predicted model is depicted as dot lines;

$$Y = \frac{100}{1 + 10^{[(logIC_{50} - X) \times S_{Hill}]}};$$

Figure 36:
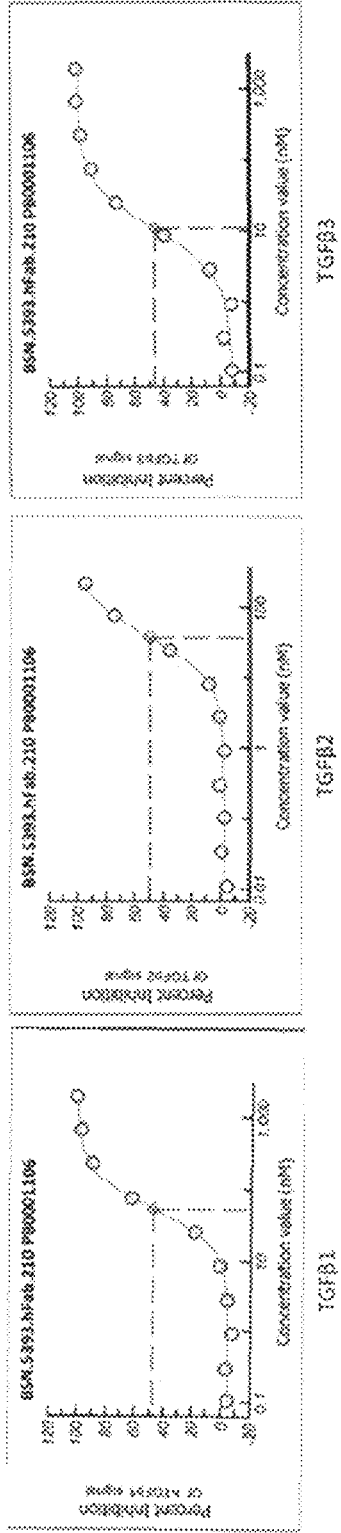
Figure 37:
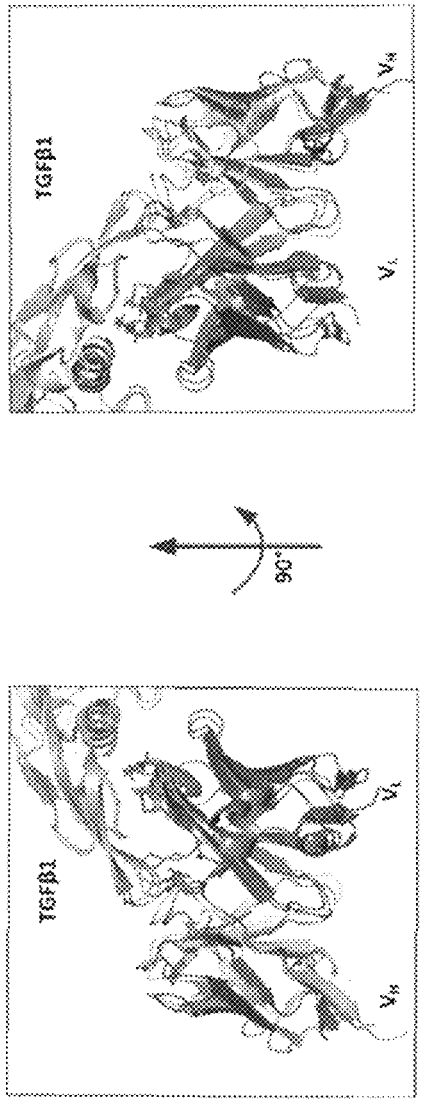

FIG. 34 depicts combined hotspot residues from TGFβR1 & 2 and Fresolimumab in pan-TGFb blocking Fab fragment design by transferring combined receptors- and Fresolimumab-inspired hotspot residues example;

FIG. 35 depicts SPR kinetics profiles for Fab184/TGFβs complexes with designed antibody Fab immobilized on the chips in pan-TGFb blocking Fab fragment design by transferring combined receptors- and Fresolimumab-inspired hotspot residues example;

FIG. 36 depicts neutralisation of TGFβs-receptors binding by titration of Fab184 TGFβs in HEK Blue reporter gene cell assay in pan-TGFb blocking Fab fragment design by transferring combined receptors- and Fresolimumab-inspired hotspot residues example;

FIG. 37 depicts comparison of the binding modes of crystal Fab184 with modelled one by superimposing onto the TGFβ1 side in pan-TGFb blocking Fab fragment design by transferring combined receptors- and Fresolimumab-inspired hotspot residues example.

According to an embodiment, there is provided a computer-implemented method of designing an antibody that will bind to a target epitope. FIGS. 1-9 schematically show example aspects of the method in flow chart form.

The method comprises a) identifying one or more hotspot residues that will each bind to a corresponding one of one or more hotspot sites on the target epitope (step 100 in FIG. 1). Each hotspot residue comprises a hotspot sub-structure. The hotspot sub-structure comprises one or more hotspot sub-structure characteristic atoms. The hotspot sub-structure characteristic atoms are atoms that will be used for matching of residues that are potentially different to the hotspot residue (i.e. derived from a different amino acid). The characteristic atoms are thus atoms which are common to residues of different amino acid type.

The method further comprises b) selecting from a database of antibody structures one or more candidate antibody structures (step 200 in FIG. 1). The antibody structures or relevant portions of the antibody structures may be referred to as antibody scaffolds. The selection is performed to find antibody structures or scaffolds that are capable of being modified to bear residues matching the hotspot residues (as described below). The nature or origin of the database is not particularly limited. The database entries may be filtered or reformatted as required. For example, in an embodiment, only database entries representing structures which have been solved by X-ray crystallography are used. In an embodiment if multiple crystal copies are available for the same antibody structure with different chain identifiers, only the first copy which appears in the PDB file may be retained for use. In an embodiment only the Fv regions are kept from the Fab structures. In an embodiment the Abnum procedure (Abhinandan, K R & Martin, A. C. R. Analysis and improvements to Kabat and structurally correct numbering of antibody variable domains. *Mol. Immunol.* 45, 3832-3839 (2008)) is used to renumber the residues in the Fv structures according to Chothia numbering scheme (Al-Lazikani, B., Lesk, A. M. & Chothia, C. Standard conformations for the canonical structures of immunoglobulins. *J. Mol. Bio.* 273, 927-948 (1997)). In an embodiment any structures with broken polypeptide CDR loops are discarded.

Each candidate antibody structure has one or more matching residues. Each of the matching residues matches a corresponding one of the hotspot residues (in the sense explained below). Each matching residue comprises a matching residue sub-structure. Each matching residue sub-structure comprises one or more matching residue sub-structure characteristic atoms. The selection is performed such that the relative positions of the matching residue sub-structure characteristic atoms within the antibody structure and the relative positions of the hotspot sub-structure characteristic atoms when bound to the target epitope are such that at least three of the matching residue sub-structure characteristic atoms can be superimposed computationally on a corresponding at least three hotspot sub-structure characteristic atoms with a spatial deviation between each pair of superimposed characteristic atoms averaged over all pairs being less than a predetermined threshold. The averaging may be achieved for example by computing a spatial separation between each pair of superimposed characteristic atoms and calculating a mean average or root mean square average of the spatial separations. Each of the corresponding matching residue sub-structure characteristic atoms and hotspot sub-structure characteristic atoms are generally of the same characteristic atom type (e.g. alpha carbon, backbone carbon derived from the carboxyl group, backbone nitrogen, backbone oxygen, beta carbon of the side chain, etc.). A matching residue is thus matched with a hotspot residue when corresponding characteristic atoms from each of the two residues can be superimposed over each other with relatively high precision (such that, overall, the average deviation satisfies the predetermined threshold as described above). The matching residue does not need to be of the same amino acid type as the hotspot residue (i.e. with the same side chain). The matching depends only on whether the two residues have characteristic atoms in the sub-structure that can be superimposed with relatively high precision. An example approach for determining whether this requirement is met for a given antibody structure is described below with reference to FIG. 8.

The matching using at least three matching residue substructure characteristic atoms and a corresponding at least three hotspot sub-structure characteristic atoms constrains the position and orientation of the candidate antibody structure relative to the target epitope to at least partially retain functionally relevant aspects of the paratope/epitope interaction geometry of the one or more identified hotspot residues and the target epitope. Matching more than three characteristic atoms and/or matching using more than one matching residue will tend to increase the geometrical constraints and retain the paratope/epitope interaction geometry more closely (see examples below).

In an embodiment the selection of step (b) is performed by looking for matching residues exclusively within an interaction site on the antibody structure, the interaction site consisting of the CDR loops or the CDR loops and any region on the surface of the antibody Fv domain.

The method further comprises c) generating a designed antibody using one of the candidate antibody structures selected in step b) (step 300 in FIG. 1). In an embodiment the candidate antibody structure is modified by replacing at least one of the matching residues with a different residue such that a predicted affinity between the designed antibody and the target epitope is higher than a predicted affinity between the candidate antibody structure and the target epitope. The different residue may be a residue of the same amino acid type as the corresponding hotspot residue for example. The replacing of a matching residue with a different residue may be referred to as grafting of the different residue. In another embodiment the candidate antibody structure is output as a designed antibody structure, without modification at this stage, in the case where each of the matching residues is already a residue of the same amino acid as the hotspot residue which the matching residue matches. The designed antibody structure produced according to any of the procedures discussed above may be modified in a subsequent step to further improve an affinity between the designed antibody and the target epitope.

In an embodiment the predetermined threshold used in step (b) is 2.0 Angstroms, optionally 1.75 Angstroms, optionally 1.5 Angstroms, optionally 1.25 Angstroms, optionally 1.0 Angstroms. There is some freedom for choosing the predetermined threshold. Choosing a relatively high threshold may lead to more candidate antibody structures being selected from the database. This may increase the chances of finding a designed antibody structure with high affinity but will tend to increase demands on further processing steps used for example to assess the potential of the selected candidate antibody structures (e.g. by assessing real or predicted affinity and the extent to which further modifications may improve affinity). Choosing a relatively low threshold may result in fewer candidate antibody structures being selected from the database but these selected structures may on average be of greater potential. This may allow further processing steps to be more focussed and thereby potentially find high affinity novel antibody structures more quickly.

In an embodiment, in step (c) the modifying comprises replacing each of at least one of the matching residues with a residue of the same amino acid as the hotspot residue which the matching residue matches. In many cases this will result in the designed antibody structure achieving relatively high affinity by presenting at least one residue that is identical to a hotspot residue in terms of side chain and which is positioned and oriented in a very similar manner to the hotspot residue when the hotspot residue is bound to the target epitope (which by definition occurs with high affinity).

However it is not essential that all matching residues are replaced with residues of the same amino acid type as the corresponding hotspot. In some cases, for at least a subset of the matching residues, a higher affinity may be obtained by not replacing the matching residue or by replacing the matching residue with a residue of an amino acid type which is not the same as the corresponding hotspot residue.

The characteristic atoms (either of the hotspot residue sub-structures or the matching residue sub-structures) may comprise one or more of the following: the alpha carbon, the backbone carbon atom derived from the carboxyl group, the backbone nitrogen, the backbone oxygen, and the beta carbon of the side chain.

In an embodiment, the alpha carbon atom of at least one of the matching residues is in one of the pairs of superimposed characteristic atoms.

In an embodiment, the pairs of superimposed characteristic atoms comprise the alpha carbon and at least one of the backbone carbon atom derived from the carboxyl group, the backbone nitrogen, the backbone oxygen, and the beta carbon of the side chain of each of at least one of the matching residues. Thus in this embodiment at least one of the matching residues has two characteristic atoms involved in the superimposition process. This provides relatively good matching in terms of position and orientation without overly constraining the selection process.

In an embodiment, the pairs of superimposed characteristic atoms comprise the alpha carbon and at least two of the backbone carbon atom derived from the carboxyl group, the backbone nitrogen, the backbone oxygen, and the beta carbon of the side chain of each of at least one of the matching residues. Thus in this embodiment at least one of the matching residues has three characteristic atoms involved in the superimposition process. This provides a relatively high degree of matching of position and orientation of the residue.

In an embodiment, the one or more matching residues consists of a single matching residue only. In such an embodiment each of the pairs of superimposed characteristic atoms will comprise a different characteristic atom from the single matching residue. In an example embodiment of this type, the at least three of the matching residue sub-structure characteristic atoms that can be superimposed on the corresponding at least three hotspot sub-structure characteristic atoms optionally comprise the alpha atom of the matching residue and at least two of the backbone carbon derived from the carboxyl group of the matching residue, the backbone nitrogen of the matching residue, the backbone oxygen of the matching residue, and the beta carbon of the side chain of the matching residue.

In an embodiment the one or more matching residues consists of a first matching residue and a second matching residue (optionally a first matching residue and a second matching only). In an example of an embodiment of this type the first matching residue comprises at least two of the matching residue sub-structure characteristic atoms that can be superimposed on the corresponding hotspot sub-structure characteristic atoms and the second matching residue comprises at least one of the matching residue sub-structure characteristic atoms that can be superimposed on the corresponding hotspot sub-structure atoms.

In an embodiment the one or more matching residues consists of a first matching residue, a second matching residue and a third matching residue (optionally a first matching residue, a second matching and a third matching residue only). In an example of an embodiment of this type each of the first matching residue, second matching residue and third matching residue comprises three of the matching residue sub-structure characteristic atoms that can be superimposed on the corresponding hotspot sub-structure characteristic atoms. This approach imposes a relative high constraint on the relative positions and orientations of the three matching residues, thereby providing a relatively focussed selection of candidate antibody structures having a relatively high average affinity (relative to less restrictive selections of candidate antibody structures) even without further modifications to improve affinity further. In a particular example of this embodiment the three of the matching residue sub-structure characteristic atoms in each of the three matching residues that are involved in the superimposition comprise the alpha carbon atom, the backbone carbon atom and the backbone nitrogen atom. The inventors have found this combination to be particularly effective, as demonstrated in the detailed Keap1 example discussed below.

As shown in FIG. 2, in an embodiment the selection of the one or more candidate antibody structures (step 200 in FIG. 1) comprises a pre-selection of a subset of antibody structures (step 210 in FIG. 2) followed by a further selection (step 220 in FIG. 2).

Figure 3:
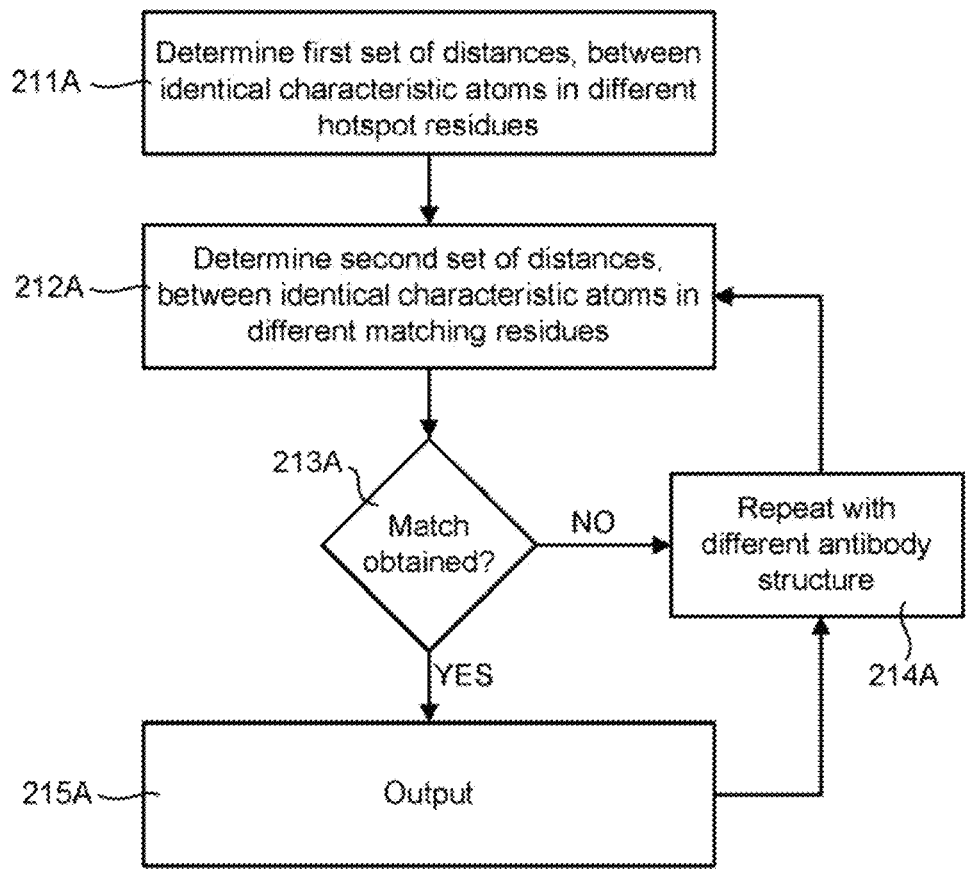
Figure 4:
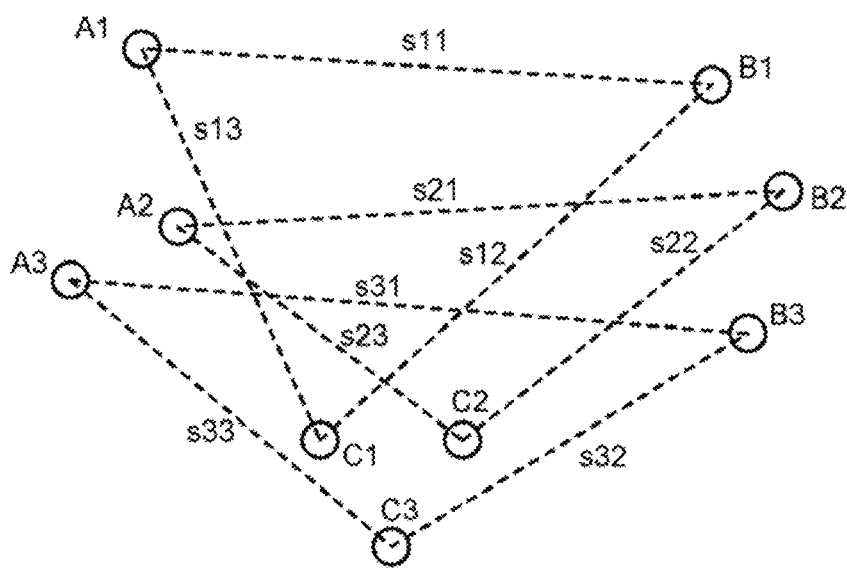

In an embodiment the pre-selection (step 210) comprises the steps set out in FIG. 3 and explained below with reference to the schematic example geometry depicted in FIG. 4. The pre-selection comprises (step 211A) determining a first set of distances representing separations between all possible pairings between identical characteristic atoms in different sub-structures of the hotspot residues. This is illustrated schematically, simplified into a two dimensional view, in FIG. 4. FIG. 4 shows the hotspot residue sub-structure characteristic atoms for three different hotspot residues: circles A1-A3 represent the characteristic atoms for a first hotspot residue, circles B1-B3 represent the characteristic atoms for a second hotspot residue, and circles C1-C3 represent the characteristic atoms for a third hotspot residue. The broken lines connect together all possible pairs of characteristic atoms of the same characteristic atom type (e.g. alpha carbon, backbone carbon derived from the carboxyl group, backbone nitrogen, backbone oxygen, beta carbon of a side chain, etc.). The lengths of all the broken lines represents the first set of distances: {s11, s12, s13, s21, s22, s23, s31, s32, s33}.

The pre-selection further comprises (step 212A) determining a second set of distances representing separations between all possible pairings between identical characteristic atoms in different sub-structures of the matching residues. This process is the same as the process of step 211A except that characteristic atoms of the matching residues are used instead of the hotspot residues. The second set of distances will take the same form as the first set of distances (e.g. a set comprising 9 numbers). In an embodiment, the numbers are expressed to a predetermined level of accuracy (e.g. rounded up to the nearest Angstrom). In an embodiment the first and second sets of distances are expressed as a sequence of numbers in a canonicalized form to allow easy comparison between sequences obtained from different antibody structures. The sequence of numbers may be used as an index for searching the database of antibody structures (see Keap1 example discussed below).

The pre-selection further comprises (step 213A) comparing the first set of distances to the second set of distances to determine if a match has been obtained within a predetermined separation threshold. For example, a sequence of numbers representing the first set, expressed to the predetermined level of accuracy (which effectively defines the predetermined separation threshold—a lower level of accuracy will correspond to a larger predetermined separation threshold and vice versa), is compared with a sequence of numbers representing the second set, expressed to the same predetermined level of accuracy. If YES, the process proceeds to step 215A and the antibody structure is output for further processing. If NO, the process loops through steps 214A, 212A and 213A to iteratively repeat the determination of the second set of distances and the comparison with the first set of distances until a match is obtained. The process may also loop through steps 214A, 212A and 213A after the output step 215A in order to select multiple antibody structures for further processing.

Figure 5:
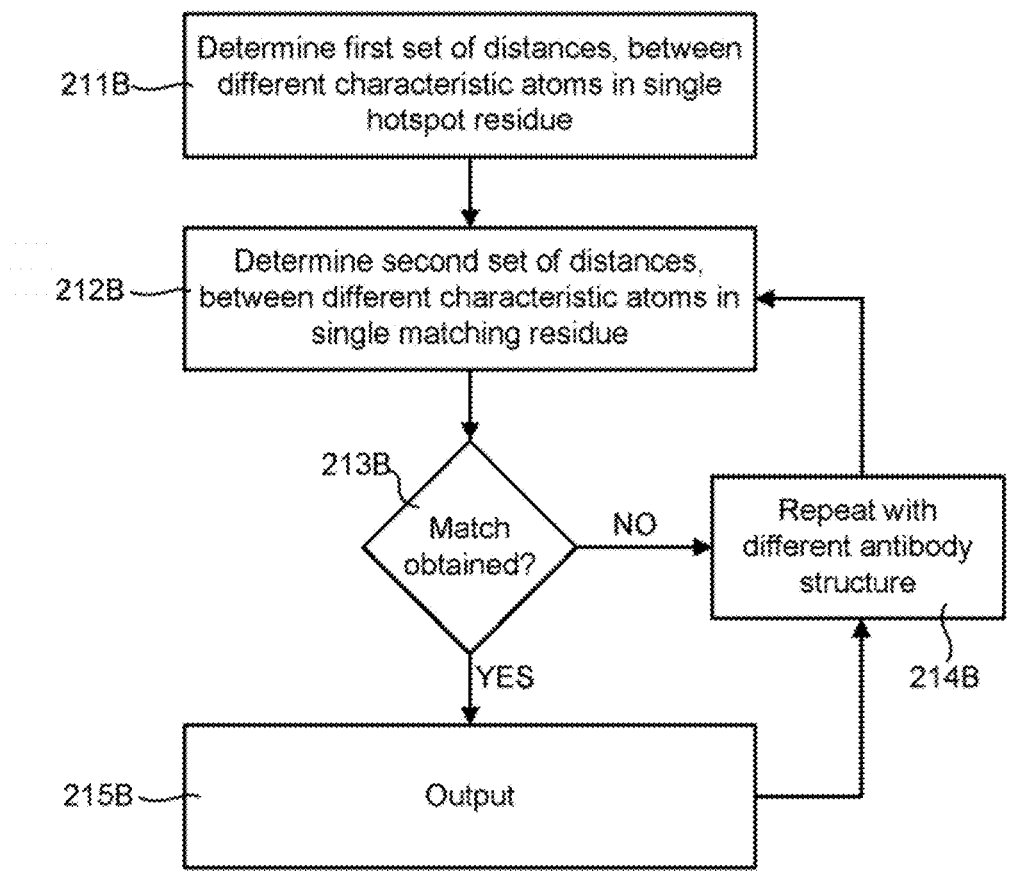
Figure 6:
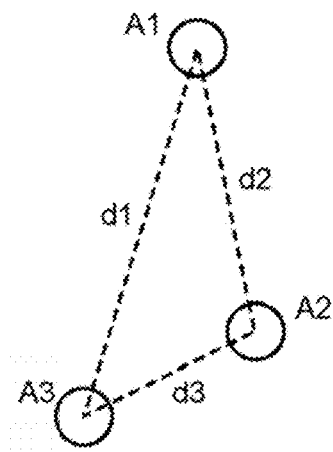
Figure 7:
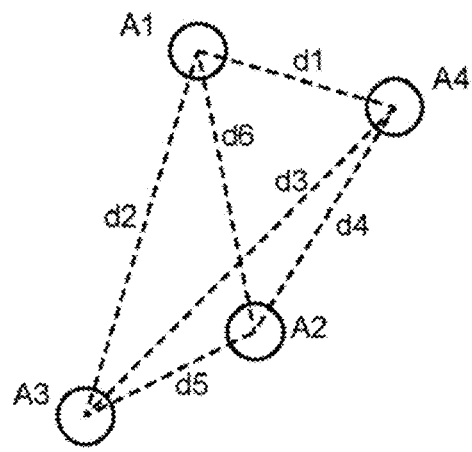

In an embodiment the pre-selection (step 210) comprises the steps set out in FIG. 5 and explained below with reference to the schematic example geometries depicted in FIGS. 6 and 7. In this embodiment the pre-selection comprises (step 211B) determining a first set of distances representing separations between all possible pairings between different characteristic atoms of the sub-structure of a single hotspot residue. This is illustrated schematically, simplified into two dimensional views, for different example hotspot sub-structures in FIGS. 6 and 7. FIG. 6 shows an example hotspot sub-structure in which three characteristic atoms A1, A2 and A3 are involved in the superimposition with a corresponding matching residue sub-structure (having a corresponding three characteristic atoms of corresponding type). FIG. 7 shows an alternative example hotspot sub-structure in which four characteristic atoms A1, A2, A3 and A4 are involved in the superimposition with a corresponding matching residue sub-structure (having a corresponding four characteristic atoms of corresponding type). In FIGS. 6 and 7 the broken lines connect together all possible pairs of characteristic atoms in the hotspot residue. By definition each pair will involve a pairing between characteristic atoms of different type to each other because they are in the same residue. The lengths of all the broken lines represents the first set of distances: {d1, d2, d3} for FIG. 6 and {d1, d2, d3, d4, d5, d6} for FIG. 7.

The pre-selection further comprises (step 212B) determining a second set of distances representing separations between all possible pairings between different characteristic atoms of the sub-structure of the matching residue. This process is the same as the process of step S211B except that the characteristic atoms of the matching residue are used instead of the characteristic atoms of the hotspot residue. The second set of distances will take the same form as the first set of distances (e.g. a set comprising 3 or 6 numbers for the particular geometries shown in FIGS. 6 and 7). In an embodiment, the numbers are expressed to a predetermined level of accuracy (e.g. rounded up to the nearest Angstrom). In an embodiment the first and second sets of distances are expressed as a sequence of numbers in a canonicalized form to allow easy comparison between sequences obtained from different antibody structures.

The pre-selection further comprises (step 213B) comparing the first set of distances to the second set of distances to determine if a match has been obtained within a predetermined separation threshold. For example, a sequence of numbers representing the first set, expressed to the predetermined level of accuracy (which effectively defines the predetermined separation threshold—a lower level of accuracy will correspond to a larger predetermined separation threshold and vice versa), is compared with a sequence of numbers representing the second set, expressed to the same predetermined level of accuracy. If YES, the process proceeds to step 215B and the antibody structure is output for further processing. If NO, the process loops through steps 214B, 212B and 213B to iteratively repeat the determination of the second set of distances and the comparison with the first set of distances until a match is obtained. The process may also loop through steps 214B, 212B and 213B after the output step 215B in order to select multiple antibody structures for further processing.

In an embodiment, the further selection step 220 of FIG. 2 comprises determining whether at least three of the matching residue sub-structure characteristic atoms can be superimposed on the corresponding at least three hotspot sub-structure characteristic atoms with the spatial deviation between each pair of superimposed atoms averaged over all pairs being less than the predetermined threshold. FIG. 8 depicts an example approach for determining when this requirement is met for a given antibody structure.

In step 221 of FIG. 8, the matching residue sub-structure characteristic atoms are computationally superimposed (i.e. overlaid) over the hotspot sub-structure characteristic atoms in the relative position or positions they occupy when bound to the target epitope. The way in which this initial superimposition is performed is not particularly limited. In step 222 a spatial deviation is calculated for each pair of identical characteristic atoms in each pair of matching residue and corresponding hotspot residue. An average of these spatial deviations is then obtained, for example by calculating a mean average or a root mean square average. If the characteristic atoms are all exactly superimposed then the average spatial deviation will be zero. Otherwise, the average spatial deviation will be a measure of the extent to which the set of pairs of characteristic atoms superimpose for the particular relative positions and orientations of the antibody structure for this iteration. In step 223 it is determined whether the average spatial deviation is below a predetermined threshold. This determination tests whether the fit is sufficiently close to be satisfactory. If YES, it is concluded that the antibody structure is a candidate antibody structure and the result is output for further processing (step 227). If NO, the process loops through steps 224, 225, 222 and 223 where the antibody structure is shifted relative to the hotspot residues and the average spatial deviation is recalculated and compared with the threshold. The process continues until either a sufficiently good match is obtained (by reaching step 227) or a predetermined maximum number of iterations has been achieved, in which case the YES branch of step 224 is followed to step 226 and the process starts again from step 221 with a different antibody structure.

In an embodiment the generating of the designed antibody comprises one or more further processing steps to modify the candidate antibody structure to further improve a predicted affinity with the target epitope (e.g. by iteratively mutating residues or iteratively swapping CDR loops—see below) or to discard antibody structures which will not work (for example due to clashing—see below). These further processing steps comprise computationally modifying the candidate antibody structure while the designed antibody is in a binding position defined by the matching to the identified hotspot residues. The sub-structure atoms of the antibody structure that correspond to the sub-structure characteristic atoms used in the superimposition of the selecting step (b) discussed above are therefore positioned relative to the target epitope at the same positions as the corresponding hotspot sub-structure characteristic atoms. In this way the superimposition process not only assists with selecting the most suitable candidate antibody structures from the database but also in providing an efficient reference for fixing the antibody structures in a way which conserves the critical paratope/epitope interaction geometry, therefore enabling the further processing steps to be performed in an efficient and effective way.

Figure 9:
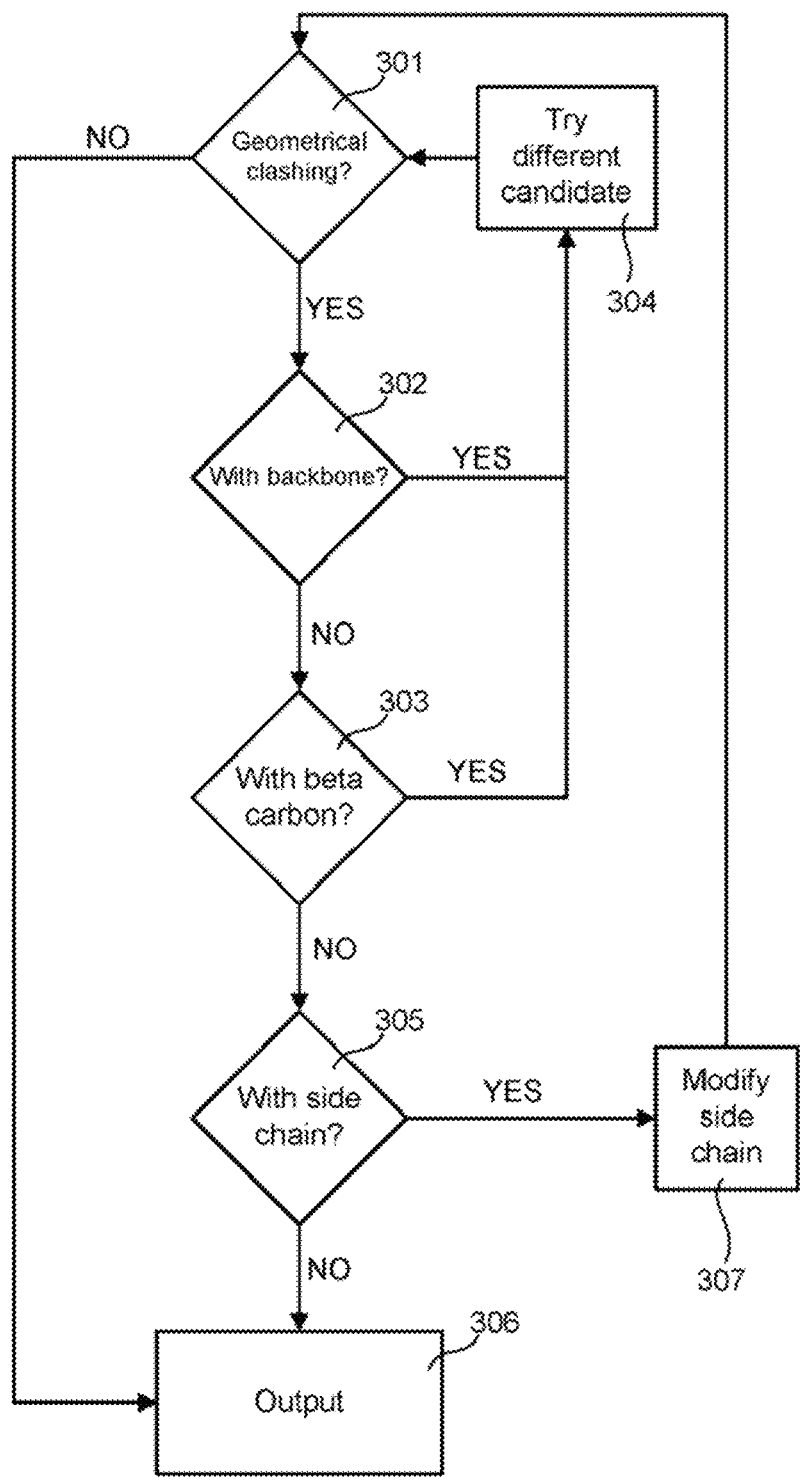

In an embodiment the generating of the designed antibody comprises detecting geometrical clashing. Geometrical clashing is where one or more atoms are predicted to occupy positions that are closer together than is physically possible when a candidate antibody structure is computationally bound to the target epitope. An example procedure for dealing with geometrical clashing is depicted in FIG. 9.

In step 301 it is determined whether geometrical clashing has occurred and, if so, which atoms are involved in the geometrical clashing. If NO, the process proceeds to step 306 where the candidate antibody structure is output for further processing. If YES, the process proceeds to step 302.

In step 302 it is determined whether the geometrical clashing involves a backbone of any candidate antibody residue. If YES, the process proceeds to steps 304 and 301, whereby the candidate antibody structure is discarded and the process is repeated with a different candidate antibody structure. If NO, the process proceeds to step 303.

In step 303 it is determined whether the geometrical clashing involves a beta carbon atom of any candidate antibody residue. If YES, the process proceeds to steps 304 and 301, whereby the candidate antibody structure is discarded and the process is repeated with a different candidate antibody structure. If NO the process proceeds to step 305.

In step 305 it is determined whether the geometrical clashing is with a side chain of a residue of the candidate antibody structure. If YES, the process proceeds to step 307 where the side chain is modified. The modification may involve swapping the side chain for a side chain of a different amino acid, for example a smaller amino acid. For example, the side chain may be modified to an alanine side chain, a glycine side chain, a valine side chain, a serine side chain, a threonine side chain, or homo-alanine side chain. The process then proceeds to step 301 where it is determined whether there is still a geometrical clash. If NO at step 305 the process proceeds to step 306 where the candidate antibody structure is output for further processing.

In an embodiment the generating of the designed antibody further comprises iteratively mutating the amino acid types of residues in the candidate antibody structure to increase a predicted affinity between the designed antibody and the target epitope. This process may be referred to as in silico mutagenesis. In an embodiment the selection of residues that are iteratively mutated is constrained so that the hotspot residues are not mutated. In other embodiments the selection of residues is not constrained to avoid mutation of the hotspot residues. Subject to the potential constraint mentioned above, the iterative mutation may comprise singly mutating all residues in a region on the candidate antibody that is expected to participate significantly in the interaction with the target epitope (e.g. an interfacial region), for example to all other amino acid types (excluding glycine, proline, and cysteine). The skilled person would be aware of various algorithms for performing computational analyses involving iterative mutations of residues to reduce a free energy associated with binding of a protein to a target. For example, the Rosetta software suite may be used (https://www.rosettacommons.org/).

In an embodiment the generating of the designed antibody further comprises iteratively swapping each of one or more of the CDR loops of the candidate antibody structure with CDR loops from a database of CDR loops to increase a predicted affinity between the candidate antibody structure and the target epitope. The affinity may be predicted for example using publically available software such as the Rosetta software suite. Swapping CDR loops greatly increases freedom of design, effectively increasing the number antibody structures that can be tested relative to the number of antibody structures available in the original database.

In an embodiment the swapping of the CDR loops is constrained so that all of the hotspot residues are retained. The inventors have found that this approach allows a designed residue of high affinity to be obtained without placing excessive demands on computing resource.

In an alternative embodiment the swapping of the CDR loops is constrained so that at least one of the hotspot residues is retained. The inventors have found that this approach provides more freedom of mutation than embodiments in which all hotspot residues are required, potentially allowing antibodies with higher affinity to be found, without demand on computing resource being increased too much.

In an embodiment the swapping of the CDR loops comprises swapping at least one of the CDRH3 loop and CDRL3 loop. These loops show the most variability. Focussing on swapping these loops allows affinity to be improved most efficiently.

In an embodiment the swapping of the CDR loops comprises swapping at least the CDRH3 loop. This loop is the most variable. Focussing on swapping this loop allows affinity to be improved even more efficiently.

In an embodiment the swapping of the CDR loops further comprises iteratively mutating the amino acid types of residues in the swapping CDR loops to increase predicted affinity between the candidate antibody structure and the target epitope. This step enables affinity to be increased still further.

One or more of the hotspot residues themselves may be identified (step 100 in FIG. 1) in a variety of different ways. In an embodiment the hotspot residues are identified from a cognate protein binder known to bind to the target epitope. This approach provides hotspots residues with a high level of reliability and predictable affinity. However, the range of hotspot residues that can be identified in this way is limited. In the Keap1 example discussed in detail below the hotspot residues were determined based on the known cognate binding partner, Nrf2.

Alternatively or additionally, one or more of the hotspot residues may be identified using a numerical method to iteratively find residues that are predicted to provide an interaction with the target epitope consistent with providing a disproportional amount of a binding energy between an antibody comprising the residues and the target epitope.

The term "hotspot" in the context of protein binding is well known in the art. The skilled person would understand that each pair of hotspot residue and corresponding hotspot site on the target epitope define an interaction between a hotspot residue and the target epitope consistent with providing a disproportional amount of a binding energy between an antibody comprising the hotspot residues and the target epitope. See for example: Fleishman, S. J. et al. Computational design of proteins targeting the conserved stem region of influenza hemagglutinin. *Science* 332, 816-821 (2011); Liu, S. et al. Nonnatural protein-protein interaction-pair design by key residues grafting. *Proc. Natl Acad. Sci. USA*, 104, 5330-5335 (2007); and Fleishman, S. J. et al. Hotspot-centric de novo design of protein binders. *J. Mol. Biol.* 413, 1047-1062 (2011).

In one embodiment multiple designed antibodies are obtained and a preferred designed antibody is selected based on its real affinity for the target epitope, determined for example using surface plasmon resonance.

Any or all of the steps of embodiments of the invention may be performed using computing apparatus known to the skilled person in combination with appropriate software and/or firmware. The software may be provided as a signal from an external source or recorded in a memory or computer readable media.

FURTHER DETAILS, SPECIFIC EXAMPLES AND RESULTS

Keap1 Example

Figure 10:
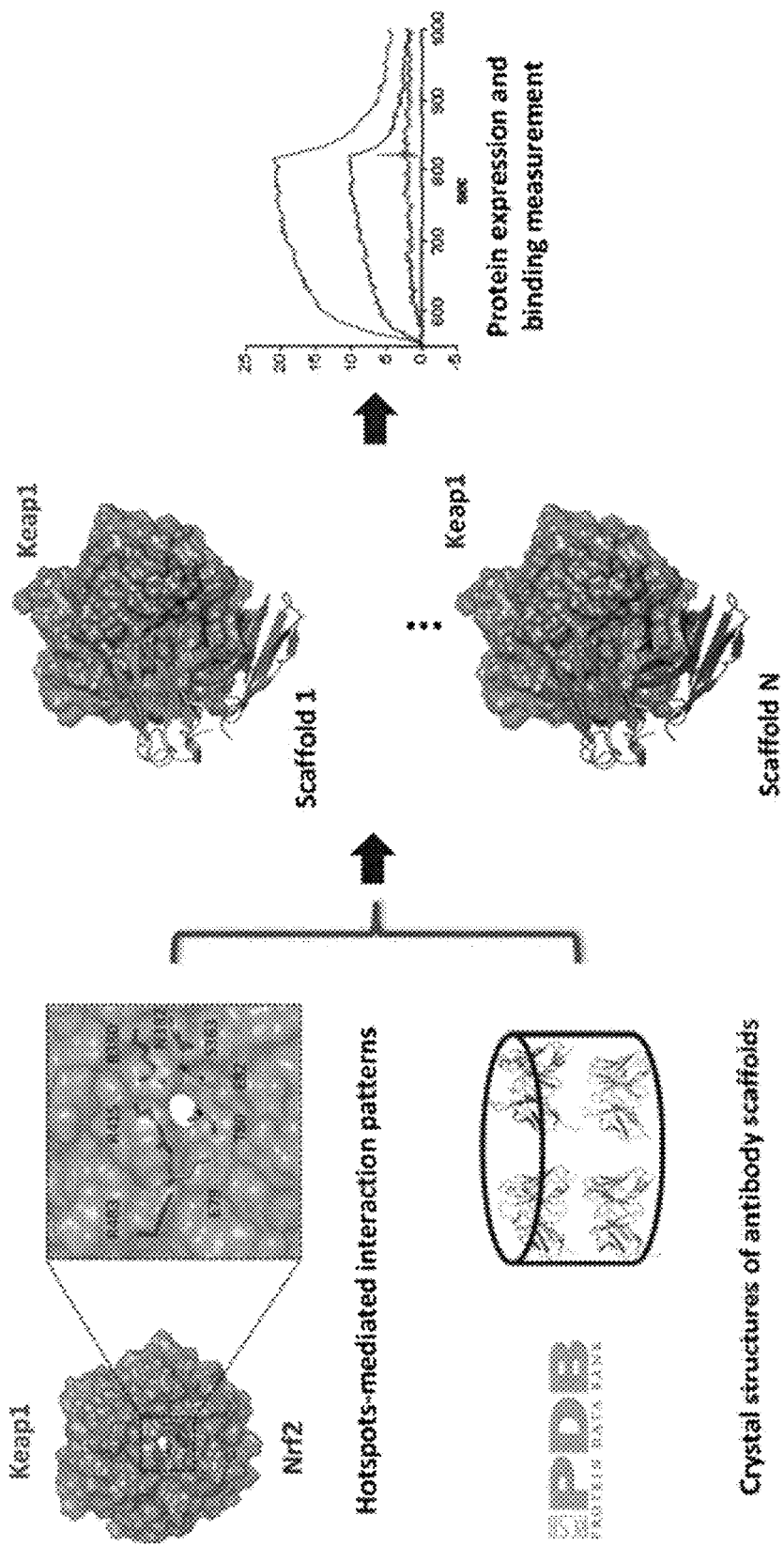
Figure 11:
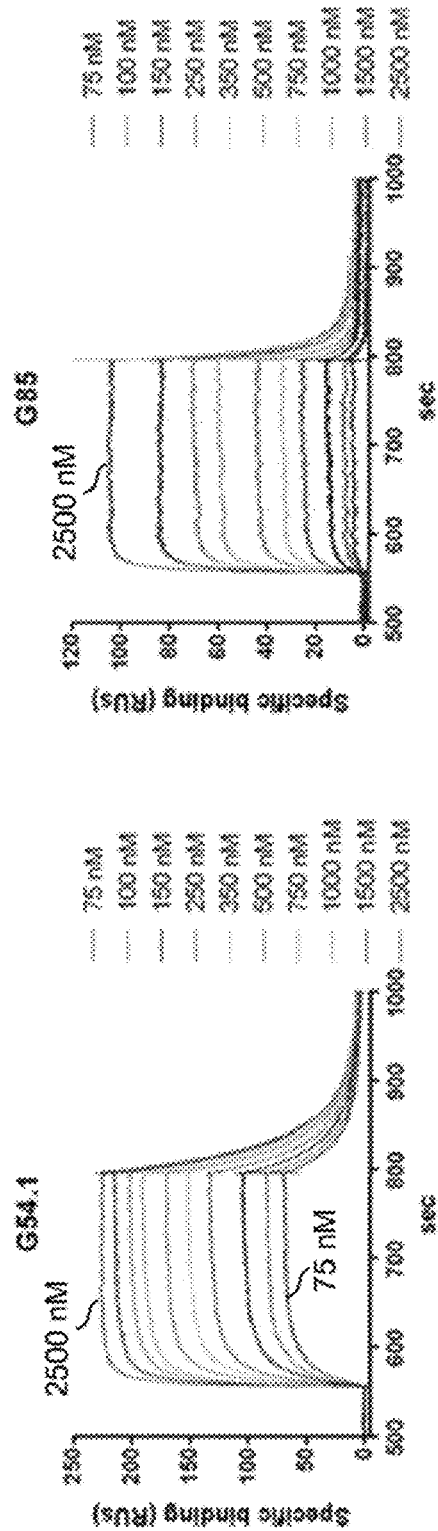
Figure 12:
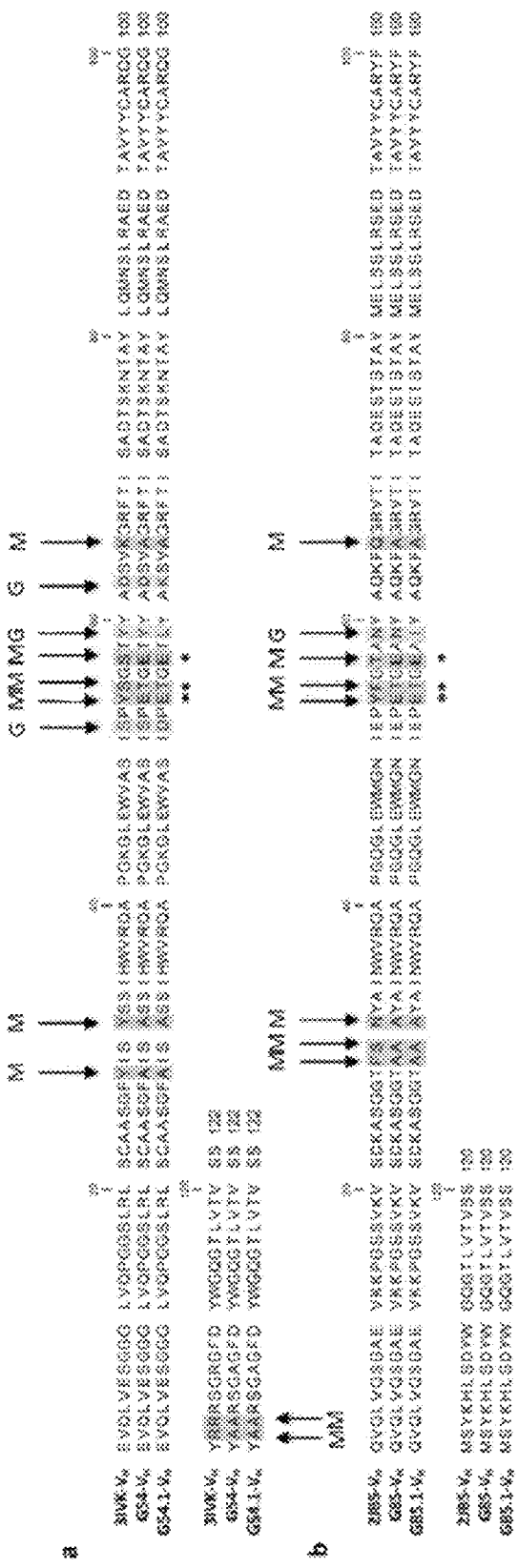
Figure 13:
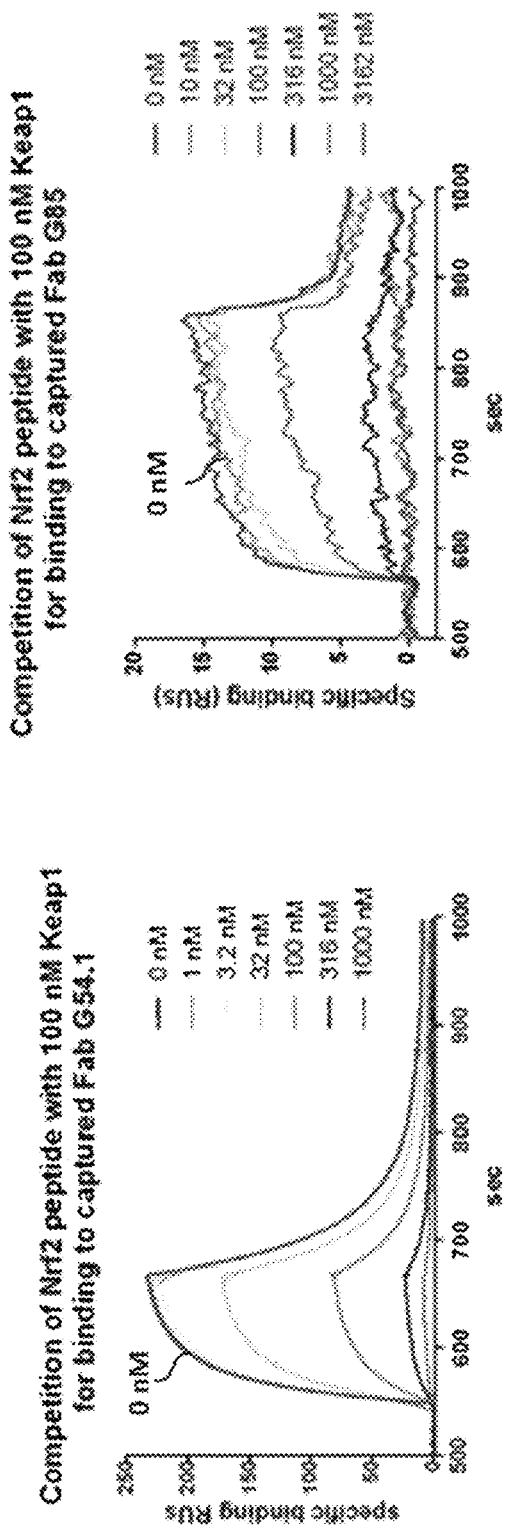

In a specific example, embodiments of the invention were applied to design antibodies binding to Keap1, a BTB-Kelch substrate adaptor protein that regulates steady-state levels of Nrf2, a bZIP transcription factor, in response to oxidative stress. Nrf2 binds to Keap1 in a 1:2 stoichiometric ratio through two hairpin loop motifs with binding affinities of 5 µM and 5 nM, respectively. Three interactional patterns, derived from hotspot residues Glu79, Thr80 and Glu82 in the higher affinity Nrf2 loop (see Supplementary Table 1), were grafted into designed antibodies' binding interfaces and ranked by computed binding energy (FIG. 10 and Supplementary Table 2). Five designs were selected and subjected to in silico mutagenesis to identify extra potential interfacial point mutations in CDR loops with improved binding energies to Keap1, leading to the generation of variants of original designs. The ten designed antibodies, before and after in silico mutagenesis, were expressed in the Fab format, and their binding affinities were measured by surface plasmon resonance (SPR). Eight of the ten selected antibody Fab designs showed detectable binding against Keap1, with the best two (G54.1 and G85) showing binding affinities in the low-to-mid nanomolar range (FIG. 11, FIG. 12 and Supplementary Tables 2-4). Binding was reduced when a cognate Nrf2 peptide binder was added as a competitor (FIG. 13), suggesting that the epitope of the designed antibodies on Keap1 overlapped with that of Nrf2. The original antibody scaffolds of G54.1 and G85 (Protein Data Bank (PDB) accession codes 3IVK and 2JB5, respectively) did not bind to Keap1, and none of the corresponding native antigens were biologically associated with Keap1 or Nrf2 (Supplementary Table 4), strongly suggesting that the Keap1 binding of both antibodies was mediated via the computationally designed interfaces. Modelled structures suggested that the three Nrf2 hotspots grafted onto CDRH2 loops of the two antibody scaffolds presented similar conformations to the Nrf2 peptide and completely occupied the Nrf2 binding sites on Keap1 along with CDRH1 and CDRH3 loops (FIG. 14).

A barrier to designing high affinity antibodies is that current approaches treat their scaffolds as rigid structures with minimal perturbation of their backbone degrees of freedom. However there is an experimentally validated precedent for transplanting CDR loops into different antibody frameworks due to the structural conservation of different loop types, thus providing alternative, additional conformation degrees of freedom that have so far been untapped by rigid-scaffold design methods. See the following publications for example: Clark, L. A. et al. An antibody loop replacement design feasibility study and a loop-swapped dimer structure. *Protein Eng. Des. Sel.* 22, 93-101 (2009); Soderlind, E. et al. Recombining germline-derived CDR sequences for creating diverse single-framework antibody libraries. *Nat. Biotechnol.* 18, 852-856 (2000); North, B., Lehmann, A., Dunbrack, R. L. A New clustering of antibody CDR loop conformations. *J. Mol. Bio.* 406, 228-256 (2011).

Figure 15:
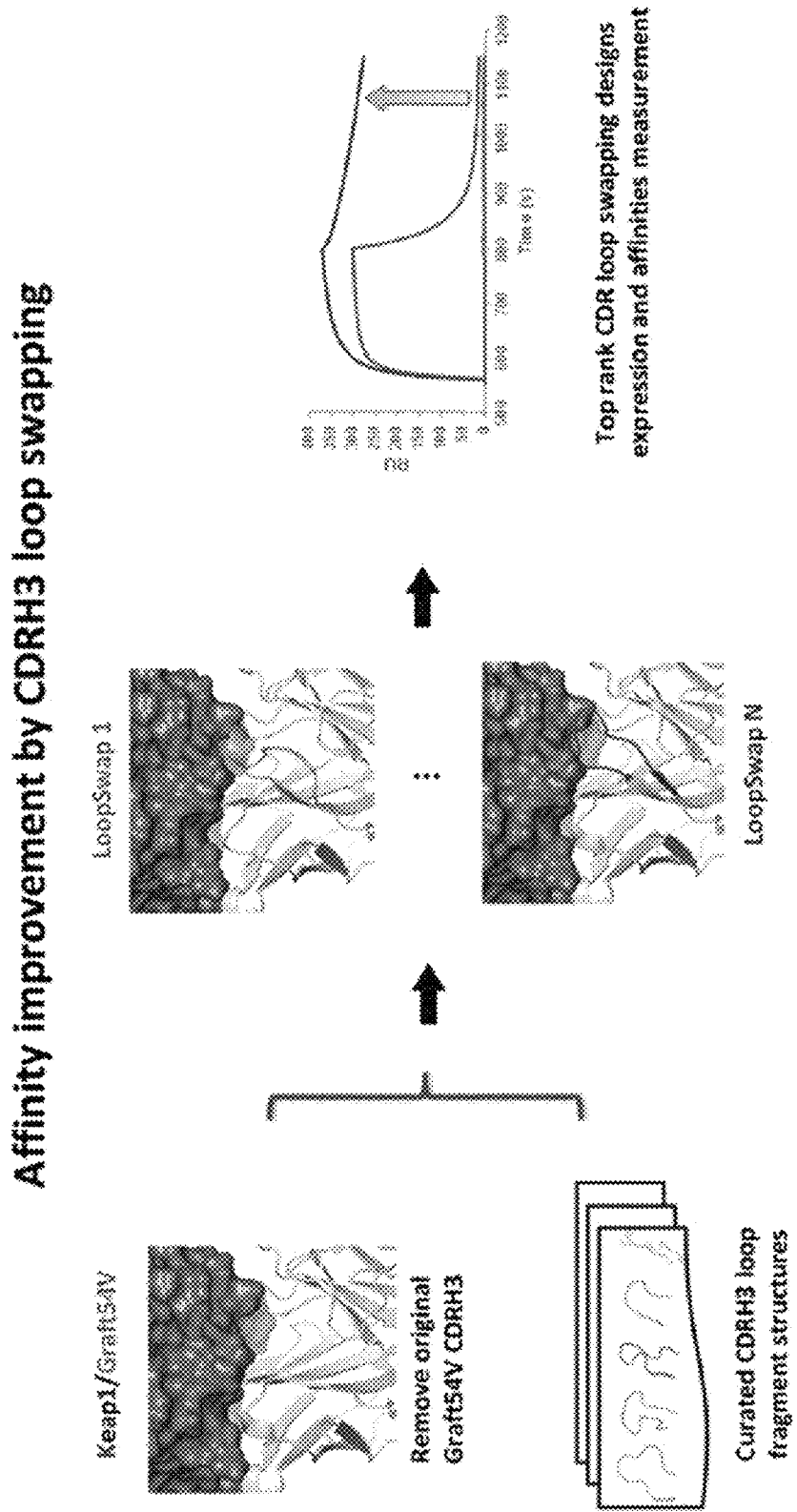
Figures 16, 17:
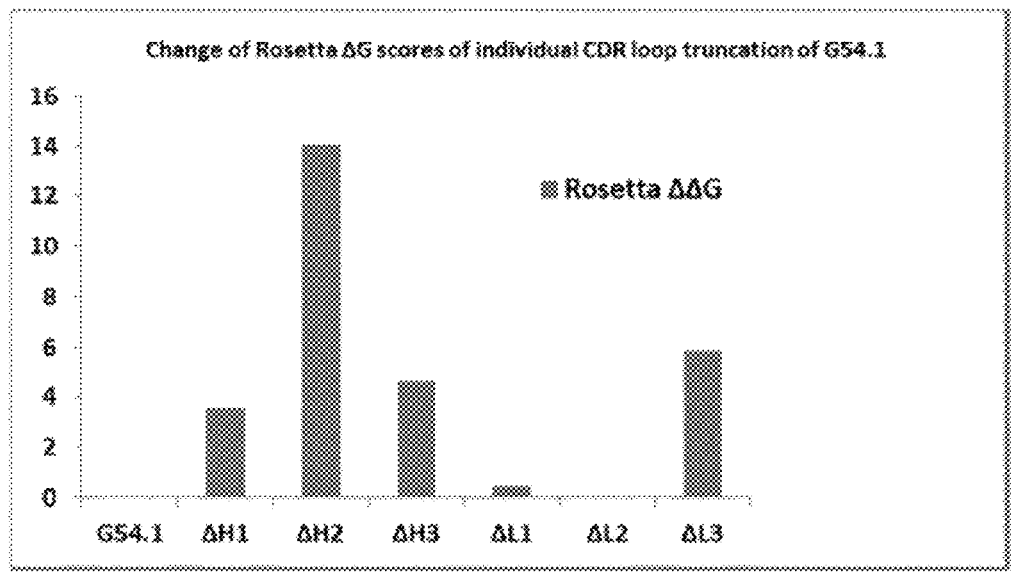
Figure 18:
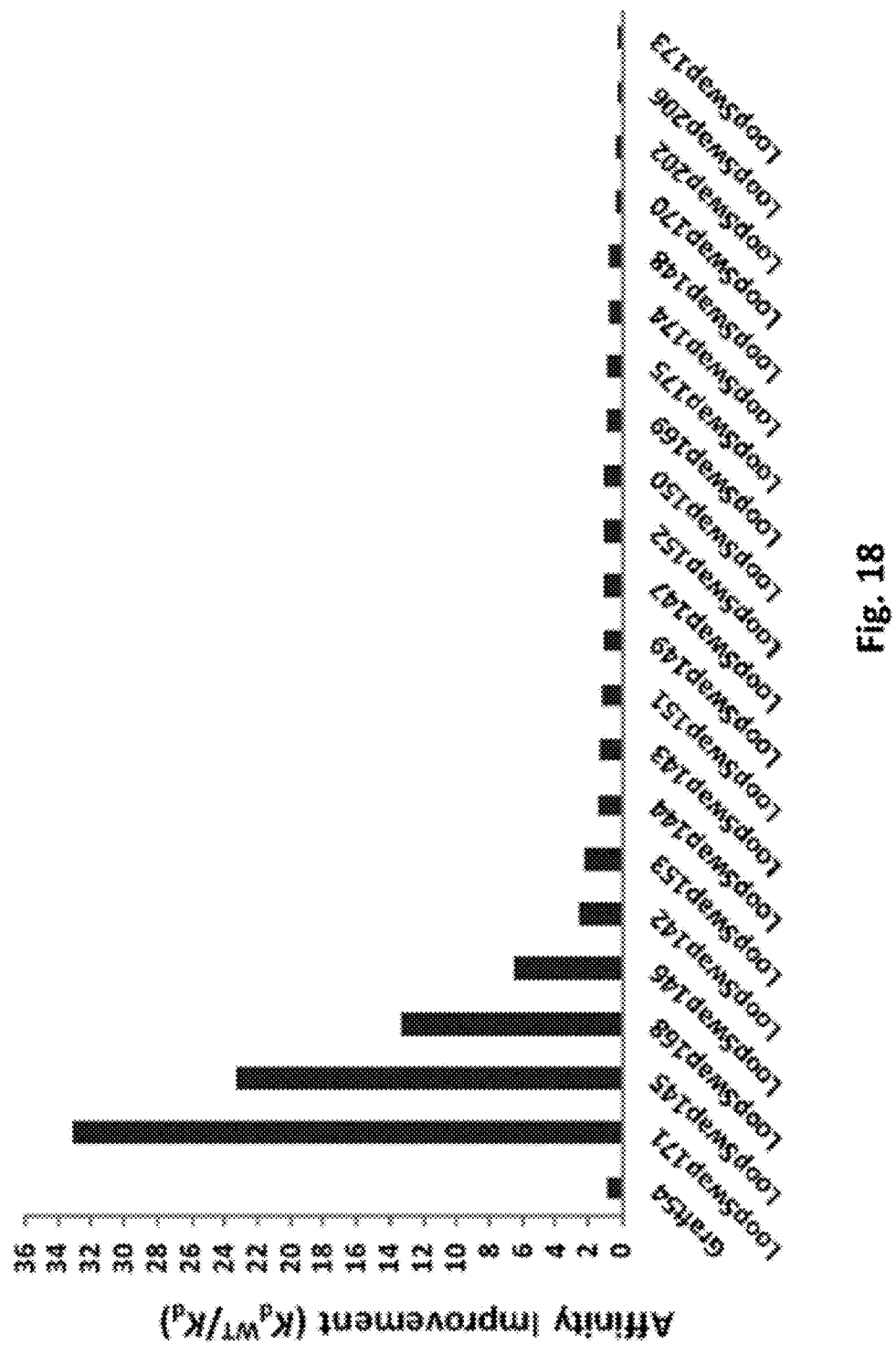
Figure 19:
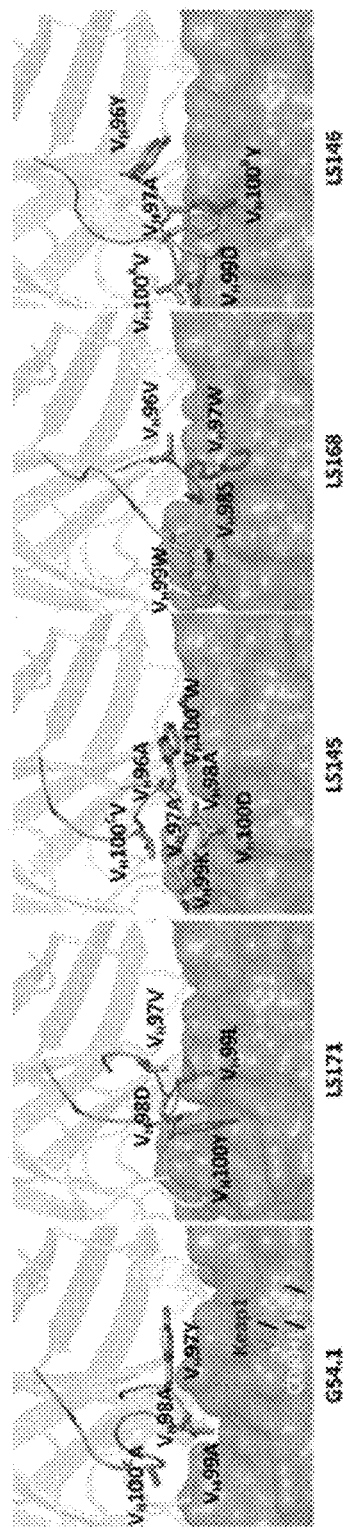
Figure 20:
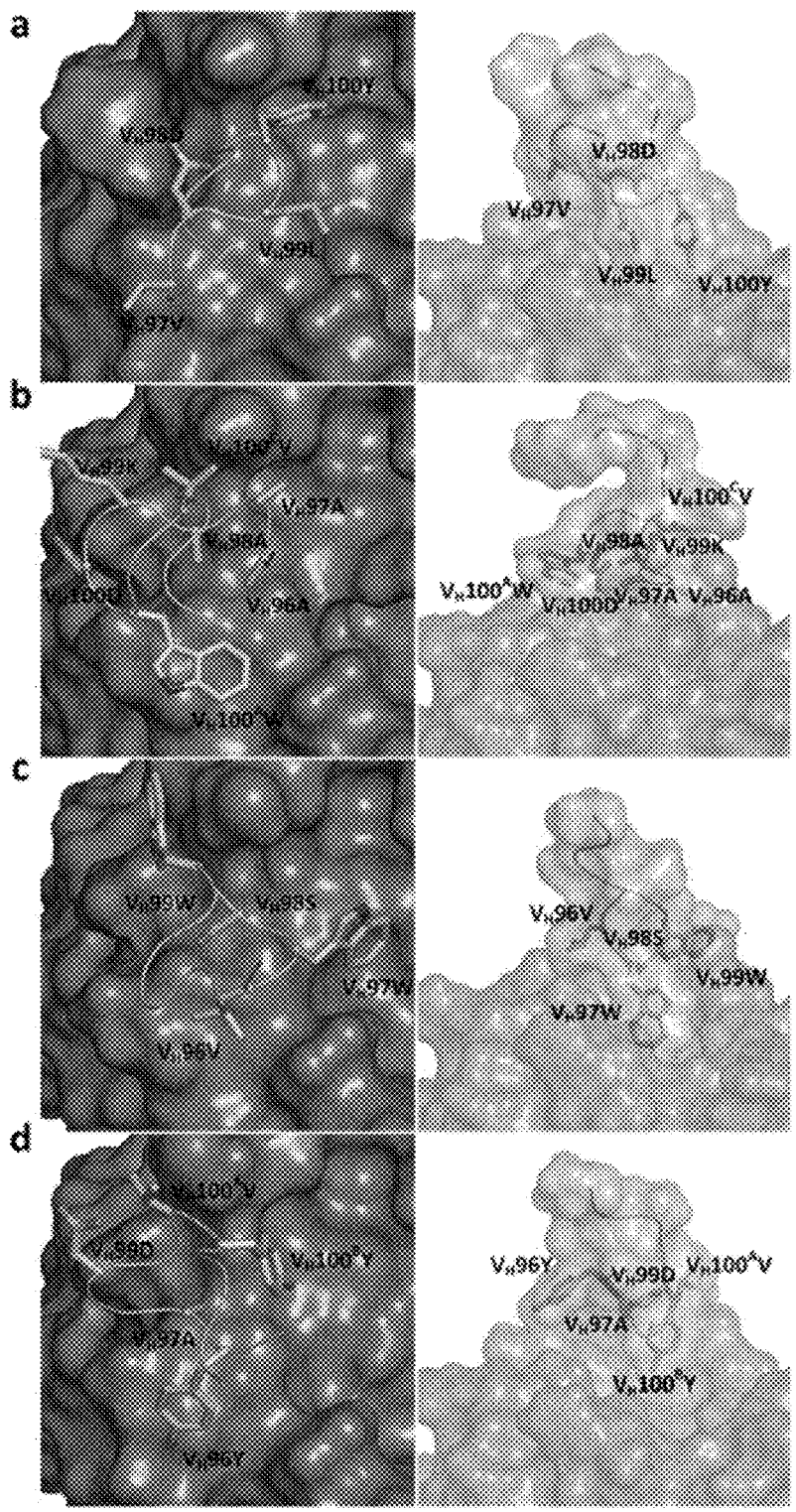

In order to improve further the binding affinity, a computational method was developed to swap the CDRH3 loop of G54.1 with ones from a curated CDRH3 loop fragment structure library (FIG. 15), given that CDRH3 is known as the most diverse antibody loop in terms of length and conformation among the six CDRs, and does not host any hotspot residues in this case (FIG. 14 and FIG. 16). The CDRH3 sequences of generated chimeric Fv fragments in complex with Keap1 were further optimised using Rosetta-Design (Kuhlman, B. et al. Design of a novel globular protein fold with atomic-level accuracy. *Science* 302, 1364-1368 (2003)) and ranked by computed binding energy. Nineteen CDRH3-swap variants of G54.1 were selected (FIG. 17 and Supplementary Tables 5-7), four of which show obviously improved affinities, with the best affinities of 4.1 and 5.4 nM measured from LS171 and LS145, representing respectively a 30- and 23-fold improvement of affinity over parental G54.1 (FIG. 18 and Supplementary Table 7), and rivaling the affinity of cognate Nrf2. LS148 and LS146, albeit with weaker affinities, show respectively 13- and 6-fold improvement. These four CDRH3 swap designs possessed completely new CDRH3 loops (sequences and lengths, FIG. 17) with different conformations from G54.1, presenting improved shape complementarity scores with Keap1 (Supplementary Tables 5). As shown in the modelled structures (FIG. 19 and FIG. 20), these affinity-improved G54.1 variants either adopt aromatic residue substitutions in shorter CDRH3 (10 vs. 13 of G54.1) to fill a void between G54.1 and the Keap1 surface (like $V_H99L$ and $V_H100Y$ in LS171, $V_H97W$ in LS168 and $V_H97Y$ in LS146), or bear larger CDRH3 contact surface areas with Keap1 (like 2734 A2 of LS168 vs. 2583 A2 of G54.1).

Figure 21:
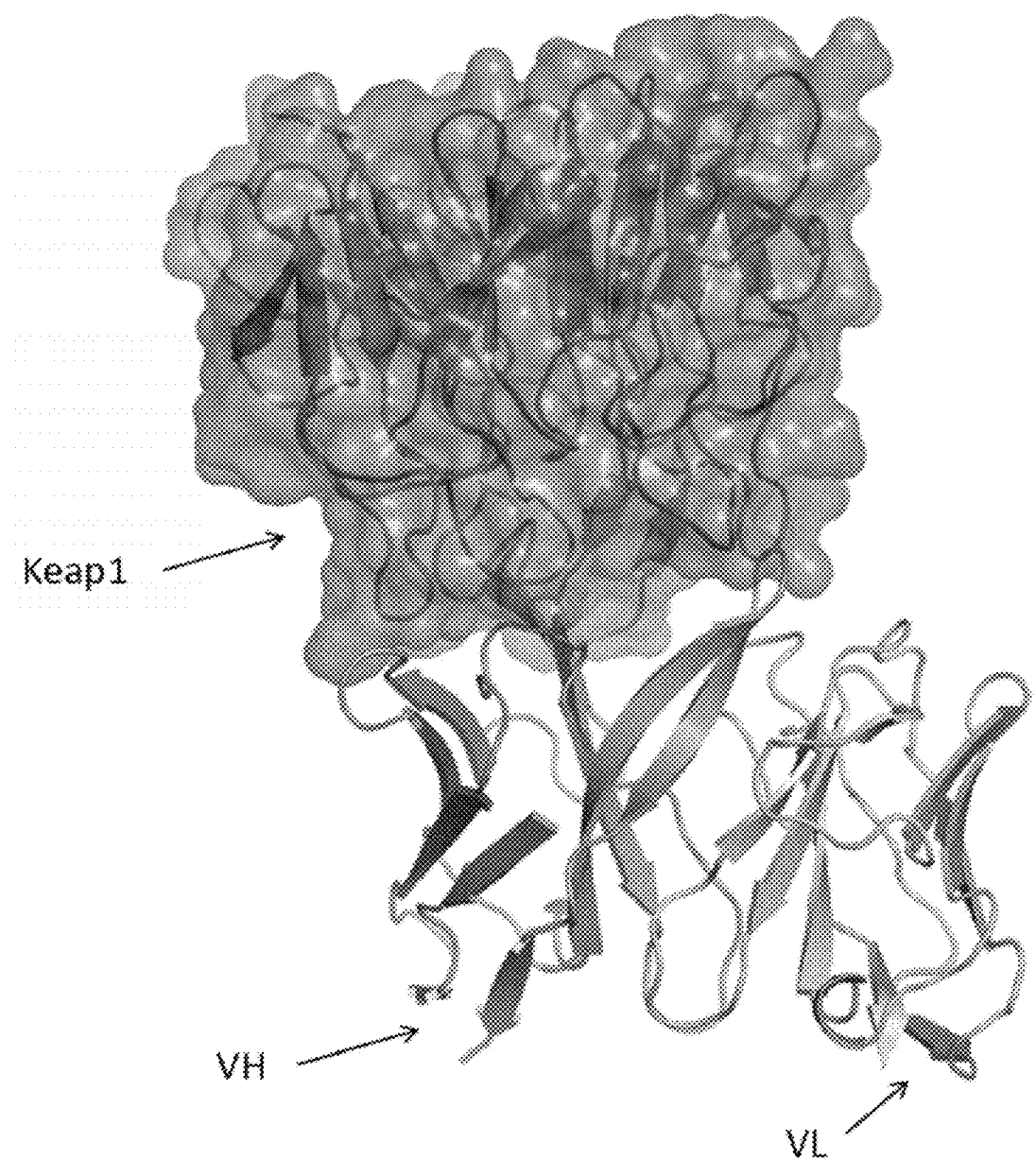
Figure 22:
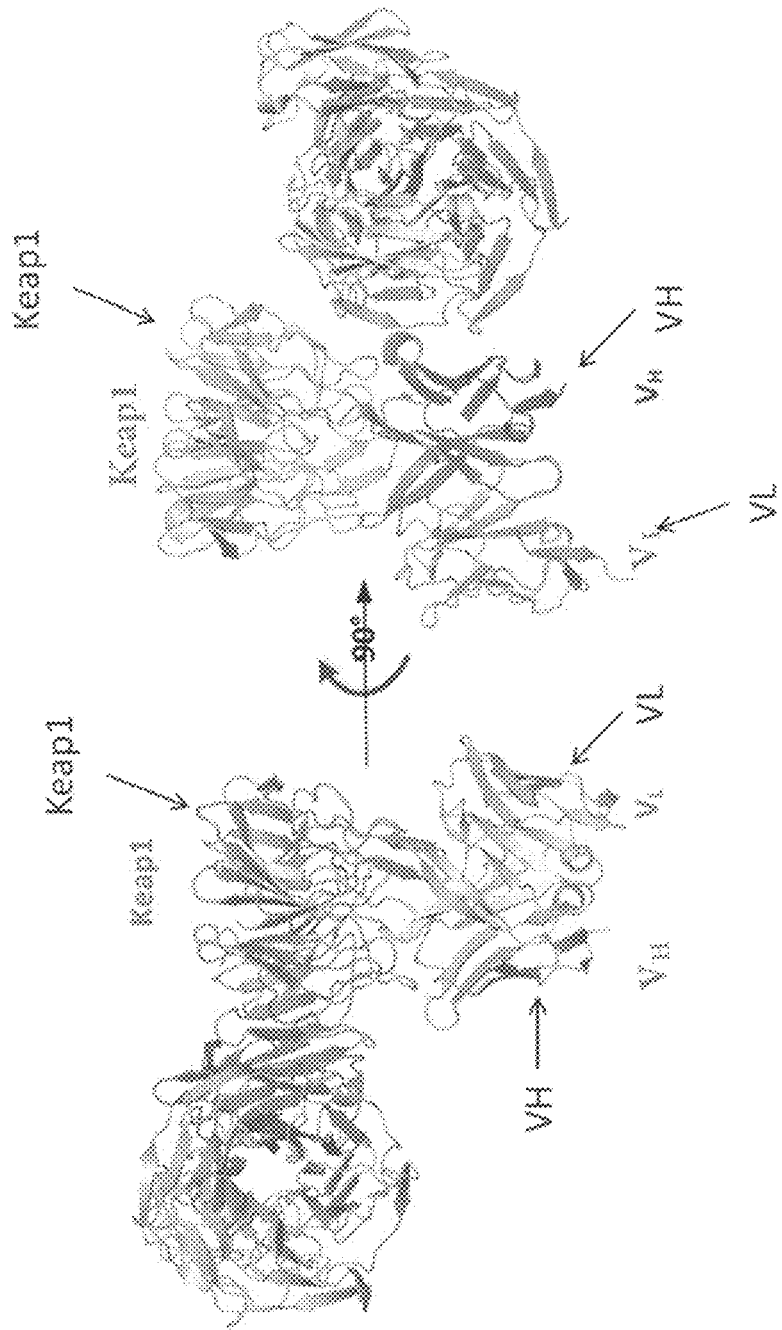
Figure 24:
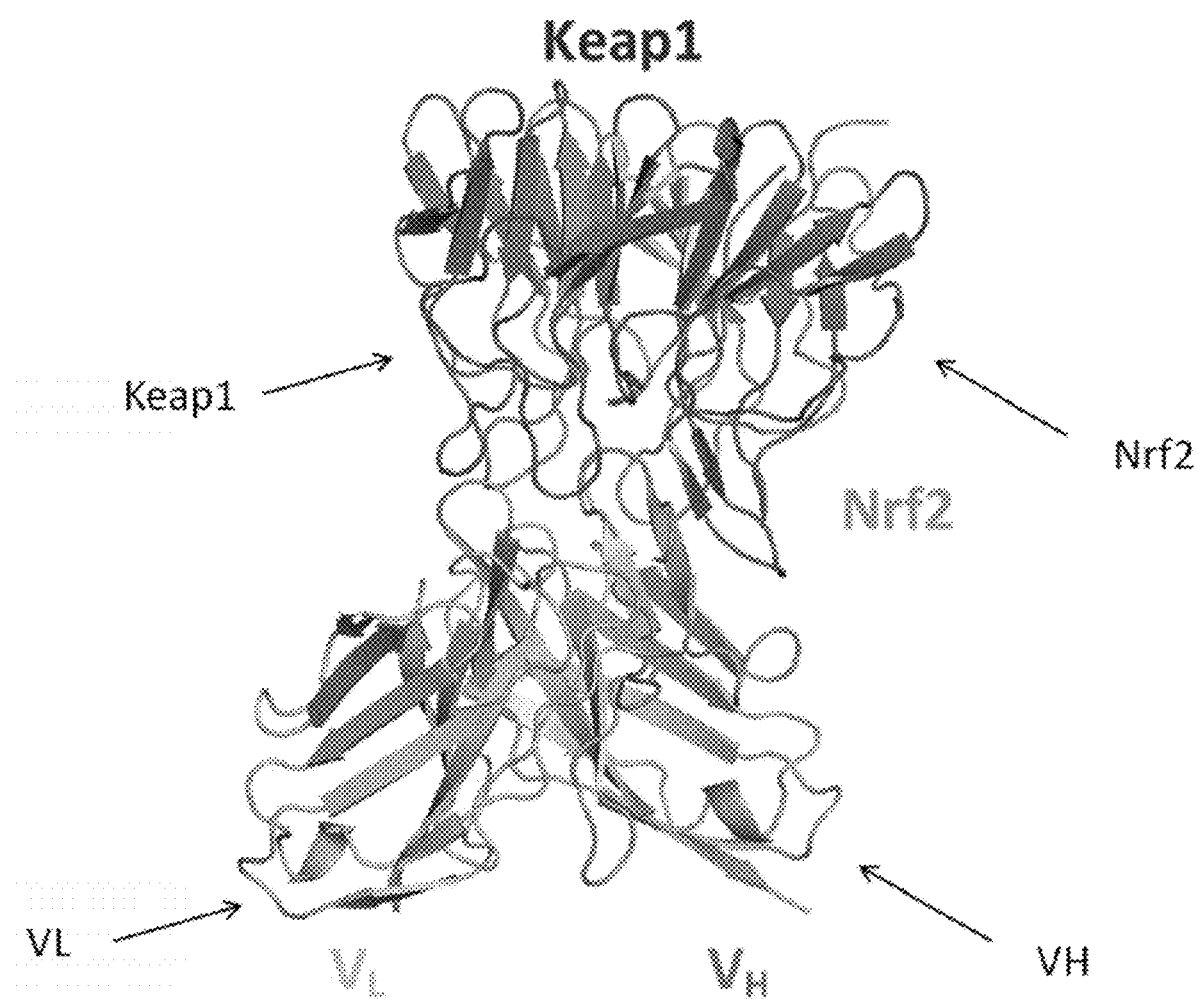
Figure 25:
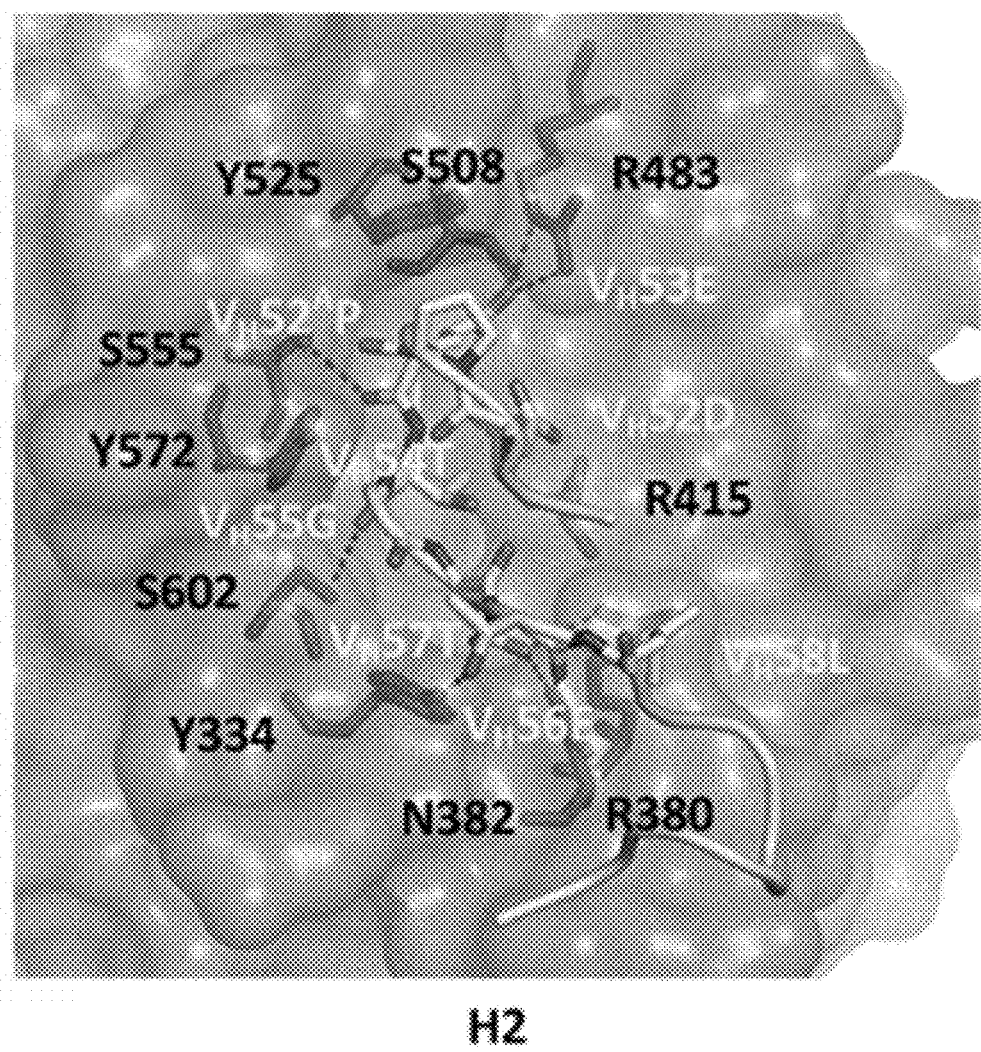
Figure 26:
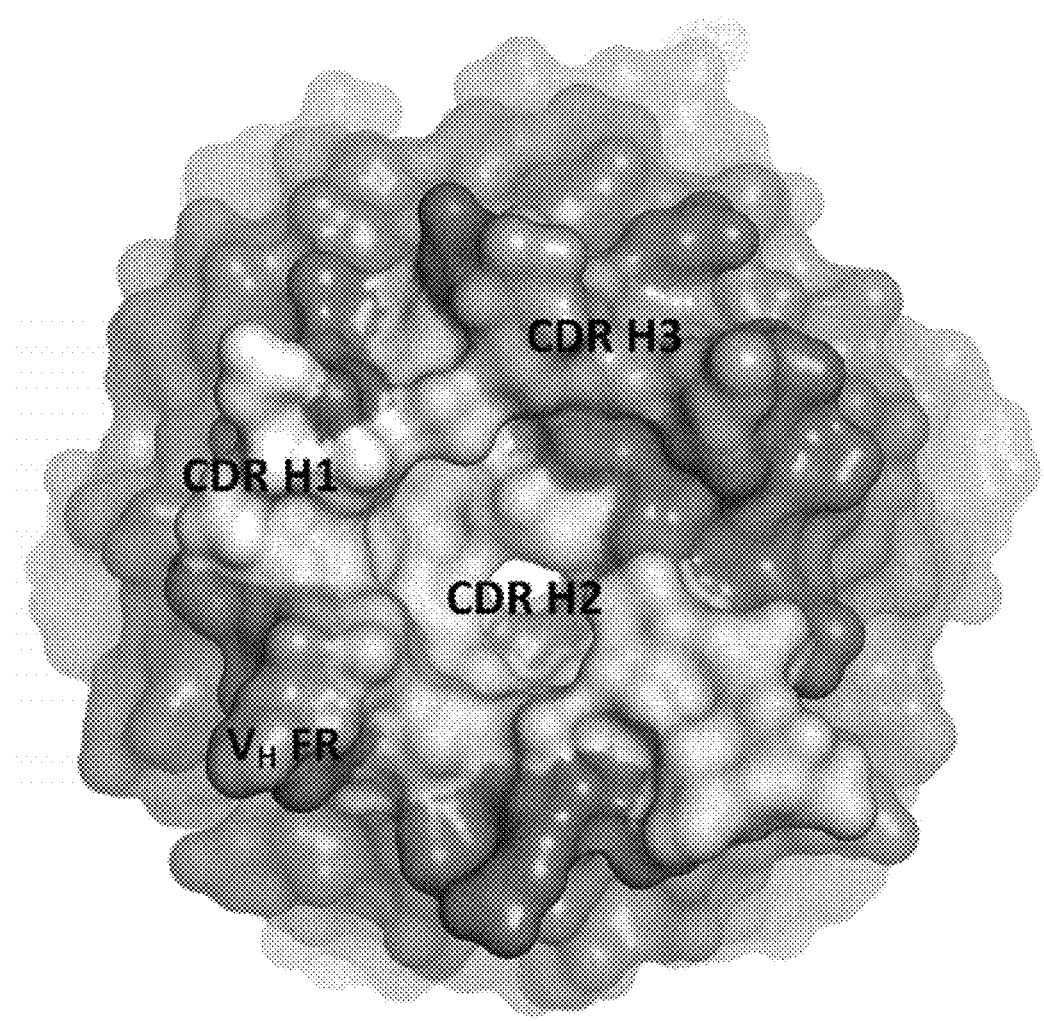
Figure 27:
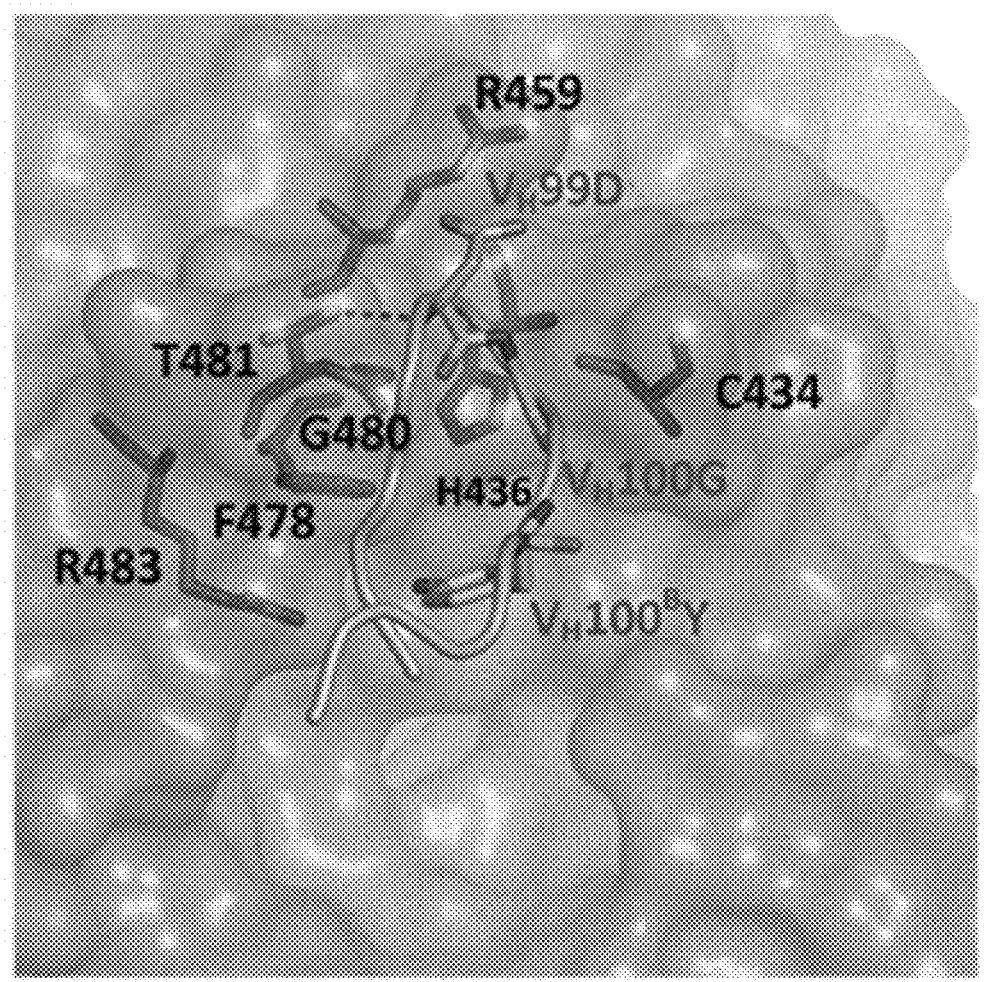
Figure 28:
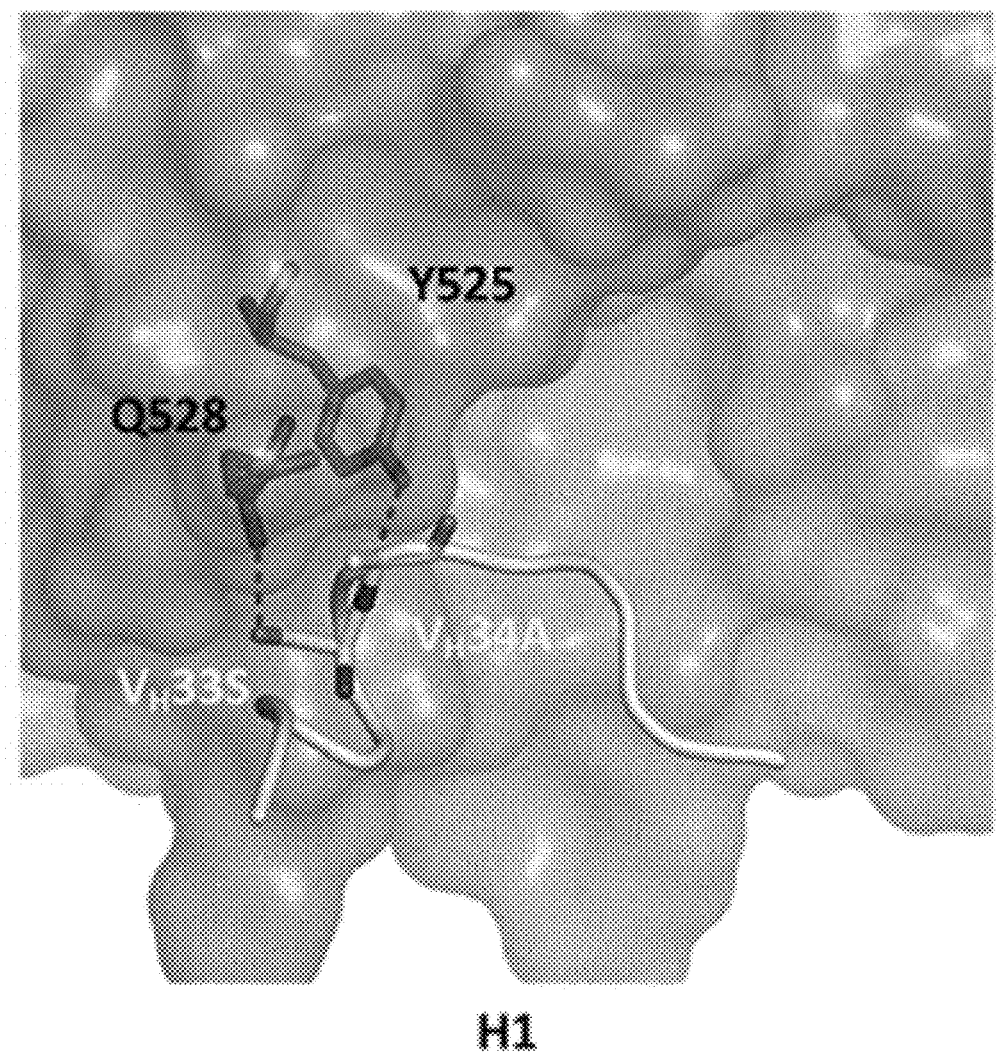
Figure 29:
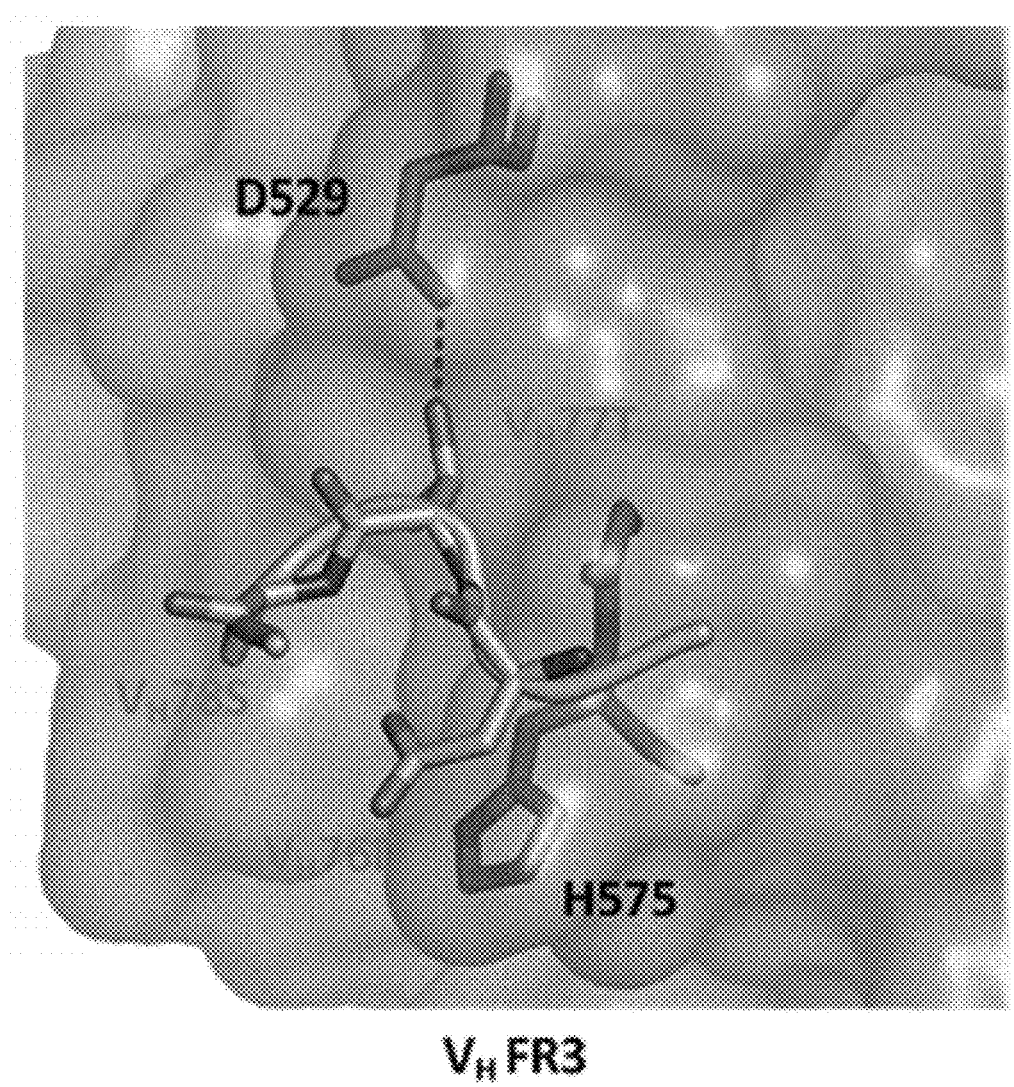
Figure 30:
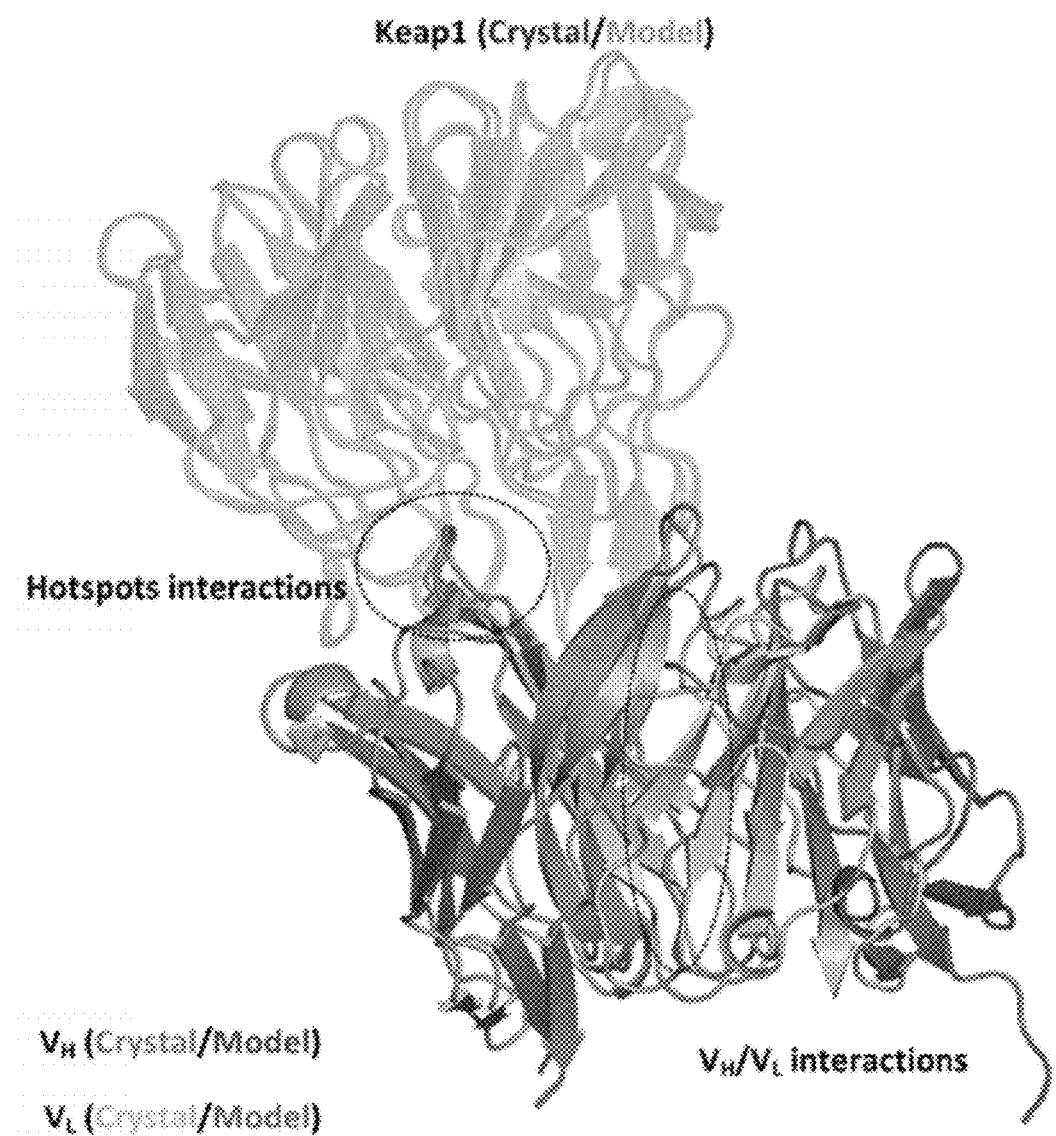
Figure 31:
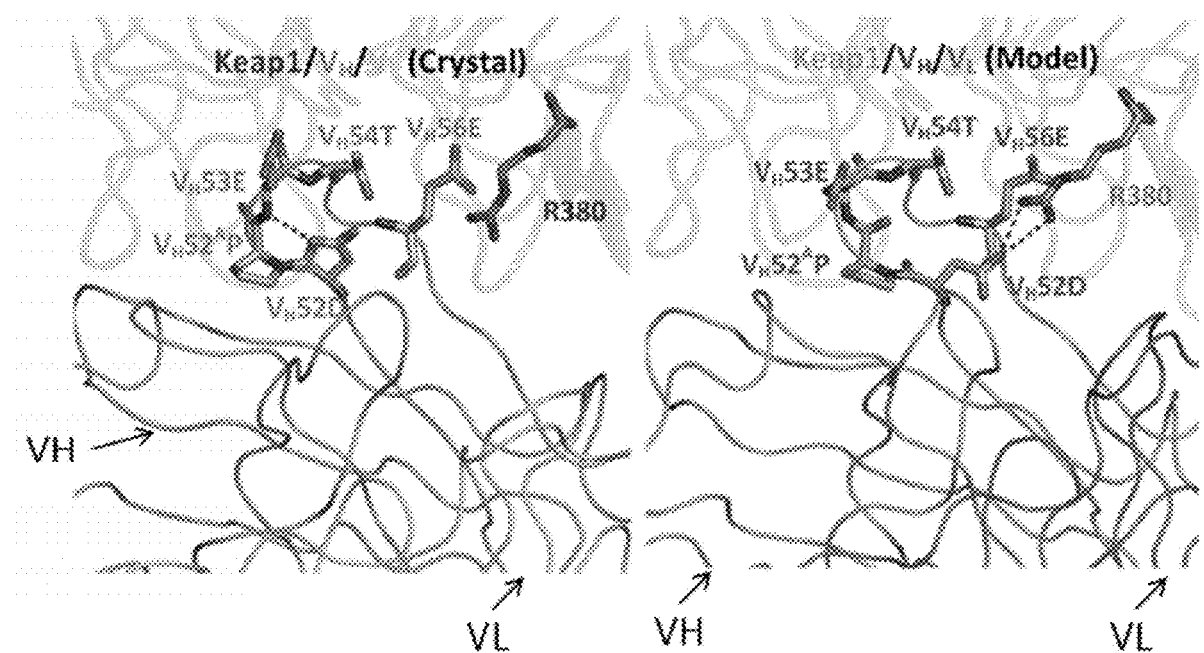
Figure 32:
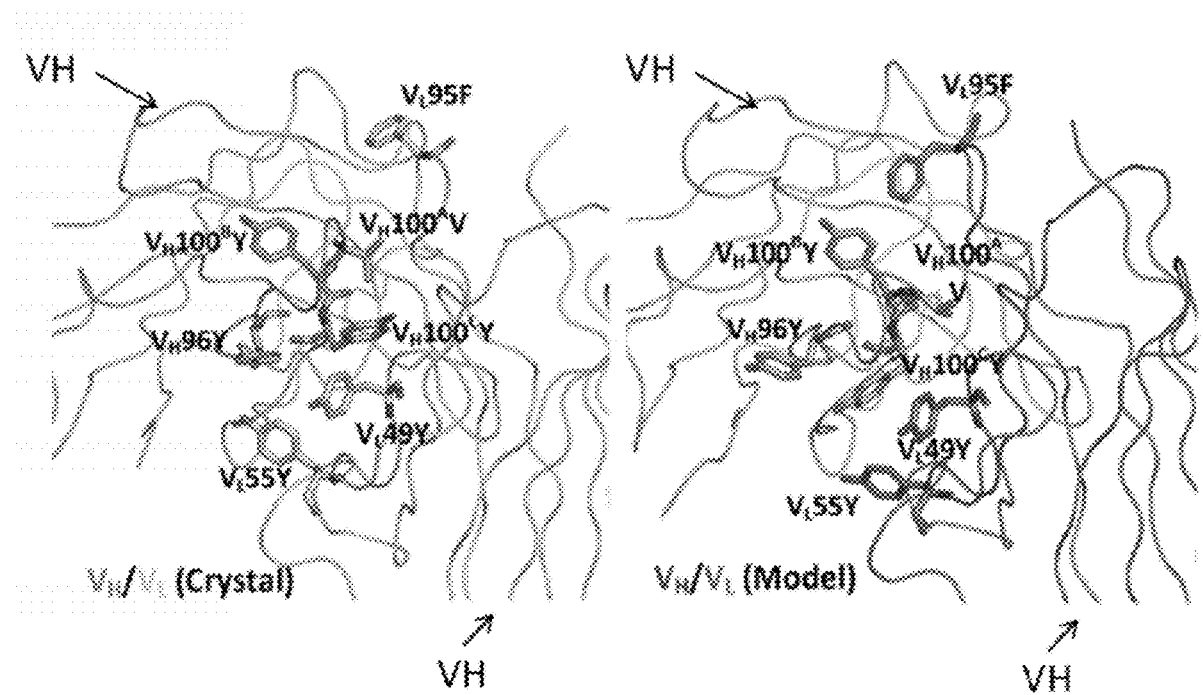
FIG. 32 depicts a crystal structure of LS146-scFv/Keap1 complex showing the precision of the computational design—comparison of residues packing at $V_H/V_L$ interface from crystal (Left) and modelled (Right) structures; the key packing residues that undergo apparent conformational change from prediction are depicted as sticks.
Figure 33:
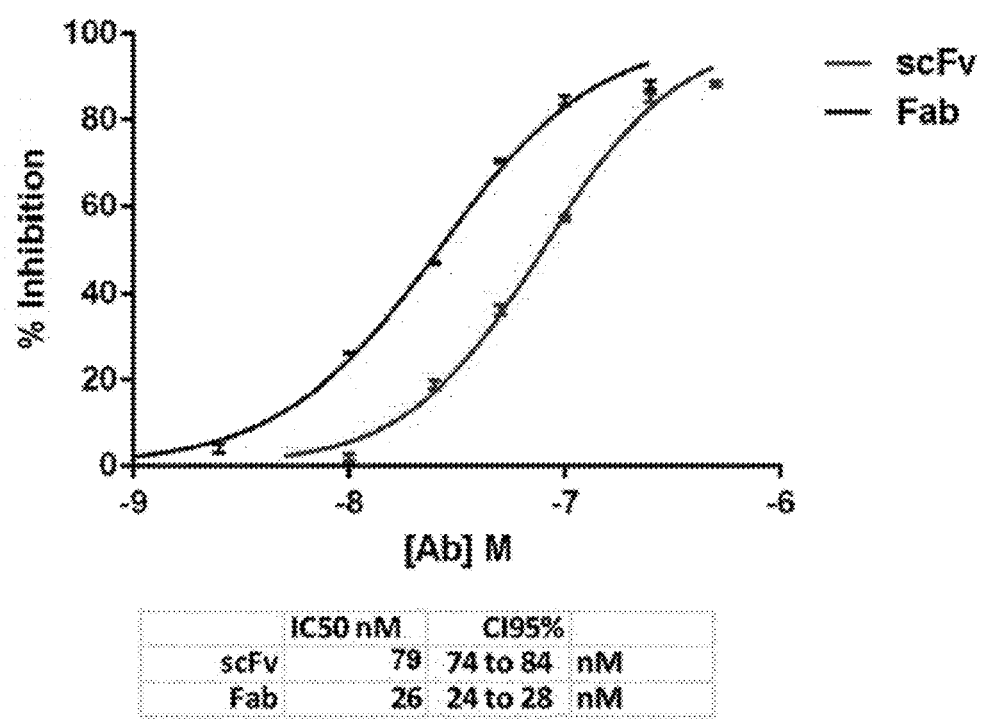
FIG. 33 depicts a comparison of potency of LS146-scFv versus -Fab in Biacore competition assay; $IC_{50}$ values were calculated by fitting to the logarithm concentration versus normalized response/variable slope model.

A high resolution (1.85 Å) crystal structure of Keap1 in complex with LS146 (FIGS. 21-23) was then solved, due to the failure of crystallographic trials with the other three highest-affinity CDRH3-swap designs to yield diffraction-quality crystals. LS146, formatted as a single chain Fv (scFv), binds almost exactly as designed in the Nrf2 binding site on Keap1 (FIG. 24), with CDRH2 making the most extensive contacts (interfacial hydrogen bond networks) to Keap1 residues (FIGS. 25 and 26). The 12-mer long CDRH3 loop folds into a hairpin-like conformation and interacts with the loops at the end of two Keap1 propeller blades as predicted (FIG. 27). Other CDR loops involved in binding are CDRH1 (FIG. 28) and part of $V_H$ framework 3 (FIG. 29). The structure of LS146-scFv bound to Keap1 shows general atomic-level agreement with the design model (interfacial-Cα-atom root-mean-square deviation (RMSD)=2.5 Å, with the two complex structures superimposed on the Keap1 side; FIG. 30). The three grafted hotspots adopt nearly identical side chain orientations as predicted (heavy-atom RMSD=1.6 Å; FIG. 31), with the exception of a flipped sidechain of $V_H52D$ due to an unexpected intramolecular hydrogen bond with backbone amide of $V_H53E$. An obvious conformational drift occurs at the tip of CDRH3 loop led by sidechain reorganisation of $V_H96Y$, $V_H100^CY$, $V_L49Y$, and $V_L55Y$ (FIG. 32), which changes the torsional angle between CDRH1 and L1 and detaches $V_L$ completely from Keap1 (Supplementary Table 8). It is known that conversion to scFv can lead to variation in $V_H/V_L$ orientation and a subsequent loss in affinity, which may explain why the potency of LS146-scFv is three-fold lower than that of its Fab form (FIG. 33).

Although CDRH2 of LS146 displays a similar structural configuration (Cα-atom RMSD=0.27 Å) as well as high sequence identity (83%) with hotspot residue donor Nrf2 'DEETGE' peptide segment, CDRH2 was not the only hotspot residue acceptor identified in antibody scaffold grafting. Because the triplet hashing (see below) was performed against all the surface CDR residues, CDRH3 was also found hosting Nrf2-inspired hotspots in some designs, albeit of much weaker affinities (Supplementary Table 4). Comparison of the properties of strong and weak binding designs suggests that more favourable computed Keap1—antibody binding energies, larger interfacial surface areas, and fewer buried unsaturated polar atoms are the most important factors (FIG. 11 and Supplementary Table 2). These are reminiscent of the well-known challenges of computational antigen-antibody interface design (large, polar binding surfaces dominated loop interactions). Rational swapping of CDR configurations enables exploration of alternative shapes and chemical complementarities that are untapped by hotspot-guided grafting design, which relies on a limited number of scaffold structures (Supplementary Table 5). The tested loop swap designs, with distinctive CDRH3 backbone conformations and sequences, show improved binding affinities by targeting the same epitope, suggesting that use of the computational CDR swap strategy described enables optimisation of in silico designed antibodies for experimental selection of higher-affinity variants.

Although not a conventional target for therapeutic antibodies given that it is an intracellular protein, the Keap1-Nrf2 interaction features readily identifiable hotspot residues that provide an ideal proof-of-concept system for structure-based design of novel antibodies targeting preselected epitopes to directly block the cognate protein-protein interactions, or alternatively to capture predicted transition states, circumventing the need to isolate or stabilise transient conformations. With further improvements in computational accuracy and parallel probing of designed sequence space, using modern oligonucleotide assembly methods, such as focused display library design, and next generation sequencing, for efficient selection of stronger binding variants, the structure-based design method offers the potential for rapid generation of antibodies for therapeutic and diagnostic applications.

Further Details of Computational Methods Applied to Keap1 Example

General Computational Methods

Anti-Keap1 antibodies targeting Nrf2 binding site were designed by a residue-based triplet hashing method to search for antibody scaffold crystal structures that are able to accommodate Nrf2 hotspots-mediated interaction patterns in the geometrically matched positions in CDRs, followed by CDRH3 swap to explore alternative loop configurations of the selected design. RosettaDesign was utilised to optimize the CDR loops' sequences of the designs during these two stages to improve the predicted binding energy to Keap1. The pseudo codes for hotspots graft, CDRH3 swap, and RosettaScripts design protocols used are provided at the end of the description.

Hotspots Graft

The triplet-based hashing method is an example of the process described above with reference to step 200 in FIG. 1, in the case where three matching residues are used, each having three sub-structure characteristic atoms involved in the superimposition. Further information about performing triplet hashing more generally may be found in the following publication: Wolfson, H. J. & Rigoutsos, I. Geometric hashing: an overview. *J. Comput. Sci. Eng.* 4, 10-21 (1997). The triplet hashing was implemented to search for antibody structures ("scaffolds") that were able to host hotspots-mediated interaction patterns from 1417 antibody crystal structures in SAbDab database (Supplementary Table 9). A 'triplet' was defined as consisting of three virtual triangles that connected three residues' backbone Cα, N and C atoms, respectively. Any three Nrf2 hotspots were compiled into a triplet and indexed with a unique key for looking up. All possible triplets of the CDRs residues in antibody scaffold structures were enumerated and indexed in the same way. The identical triplets from hotspots and antibody scaffolds were identified by comparing the respective index keys. The antibody scaffolds were grafted onto the hotspots by superimposing the scaffold triplet onto the corresponding identical hotspots one to minimise the RMSD between two sets of nine vertexes in the three triplet triangles. The three scaffold triplet residues were replaced with corresponding hotspots ones. The designed structures after triplet superimposition and hotspots graft were discarded if the backbone atoms of any residues in the grafted antibody scaffolds clashed with Keap1.

CDRH3 Loop Swap

All the exogenous CDRH3 loops were dissected from the 1417 antibody scaffold structures aforementioned. The original CDRH3 loop was removed from G54.1/Keap1 complex structure in the same way, onto which each exogenous CDRH3 loop was grafted by superimposing the backbone atoms of the anchor residues, and then ligated onto G54.1 framework by connecting the new CDRH3 anchor residues with the adjacent G54.1 framework residues. The designed structures were discarded if the backbone atoms of the new CDRH3 loop clashed with either original G54.1 Fv or Keap1.

Rosetta Sequence Design

Two rounds of Rosetta sequence design were used, aiming for optimising the computed binding energies for the designs obtained from hotspots graft and CDRH3 loop swap, respectively. During the first round, starting from the five designed antibody structures that accommodated the three Nrf2 hotspots-mediated interaction patterns, each interfacial position in antibody side was singly mutated to all other amino acid types (excluding glycine, proline, and cysteine). Each mutation structure was optimized by repack and minimization of all the interfacial residues. The changes of computed binding energies for each point mutation (termed ΔΔG) were evaluated in Rosetta full-atom scoring terms with the long-range electrostatics correction (see Fleishman, S. J. et al. RosettaScripts: A scripting language interface to the Rosetta macromolecular modelling suite. *PLoS ONE* 6, e20161 (2011)). Maximum five top ranked single point mutations in terms of lowest ΔΔG scores were selected for manual incorporation into a combined mutant variant of each original design. During the second round, all CDRH3 residues in CDRH3-swap variants of G54.1 were allowed to mutate into all other amino acid types (excluding glycine, proline, and cysteine) simultaneously, with the backbone conformation of all interfacial residues on CDRs and Keap1 locally perturbed using backrub method, which has been reported to help improving mutant side-chains prediction (Smith, C. A., Kortemme, T. Backrub-like backbone simulation recapitulates natural protein conformational variability and improves mutant side-chain prediction. *J. Mol. Biol.* 380, 742-756 (2008). Three iterations of sequence design were used to increase the likelihood that higher-affinity interactions could be found, starting with a soft-repulsive potential, and ending with the default standard van-der-Waals parameters.

Design Scoring

Designs were evaluated by computed binding energy (Rosetta ΔG score), buried solvent accessible surface area (SASA), and shape complementarity (Sc) score (see Lawrence, M. C., Colman, P. M. Shape complementarity at protein/protein interfaces. *J. Mol. Biol.* 234. 946-950 (1993)). High shape complementarity was enforced by rejecting designs with Sc<0.5 in hotspots graft and Sc<0.6 in CDRH3 swap. Rosetta total energy for each designed complex structure, and number of buried unsaturated polar atoms (Stranges, P. B. & Kuhlman, B. A comparison of successful and failed protein interface designs highlights the challenges of designing buried hydrogen bonds. *Protein Sci.* 22, 74-82 (2013)) were used as the reference of the design quality evaluation as well.

General Experimental Methods

Detailed procedures for the Keap1 protein as well as antibodies expression, cloning, purification, crystallization are given below and Supplementary Tables 10, 11.

Binding Analysis

Surface plasmon resonance (SPR) experiments were carried out on a Biacore 3000 system (GE Healthcare) and detailed experimental details are given below. Briefly, supernatant containing expressed Fab (or sham transfected supernatant control) was injected over immobilized anti-human F(ab')$_2$ polyclonal on a CM5 chip. A second injection of a Keap1 titration or a zero analyte control allowed association and dissociation kinetics to be monitored. Chip regeneration completed each sensorgram cycle. Sensorgrams were corrected for baseline drift, caused by slow dissociation of captured Fab, by subtraction of an adjacent zero analyte control cycle. Non-specific binding of Keap1 at each concentration was corrected for by subtraction of the equivalent, baseline corrected, control supernatant cycle sensorgram. Biaevaluation™ software was used to fit association and dissociation kinetics and hence determine affinity constants ($K_D$). Specificity of Fab binding to Keap1 was assessed by the same protocol by titration of an Nrf2 peptide analogue against a constant concentration of Keap1.

Supplementary Information

Nrf2 Hotspots Identification

Three Nrf2 hotspot residues dominating the binding to Keap1 were identified using Rosetta in silico alanine scanning script AlaScan.xml (see Das, R., Baker, D. Macromolecular modeling with Rosetta. *Annu. Rev. Biochem.* 77, 363-382 (2008)). The binding energy of Nrf2 and Keap1 in the complex structure (PDB accession code 2FLU—see Lo, S. C., Li, X., Henzl, M. T., Beamer, L. J. & Hannink, M. Structure of the Keap1:Nrf2 interface provides mechanistic insight into Nrf2 signalling *Embo J.* 25, 3605-3617 (2006)) was predicted by calculating the Rosetta total energy difference using default all-atom forcefield (score12 weights) between bound and unbound structures, referred as Rosetta ΔG scores hereafter. Each Nrf2 residue was in silico mutated into alanine, and the top ranked three Nrf2 residues (Glu79, Thr80, and Glu82) with the Rosetta ΔG scores decreased by at least 0.8 Rosetta energy unit (REU) after alanine mutation were confirmed as hotspots (Supplementary Table 1). The hotspots conformations were diversified by generation of inverse rotamers starting from their side chain atoms nearest to the Keap1 surface using the Rosetta script InverseRotamers.xml. Extra rotamer sampling (two half step standard deviations) was performed around all side chain torsion angles.

Antibody V-Region Scaffold Structures

The antibody V-region scaffold structures with at least one paired $V_H/V_L$ stored in PDB were extracted from SabDab database in 2014. Only the structures solved by X-ray crystallography were used, including Fab and scFv formats. If multiple crystal copies were available for the same antibody structure with different chain identifiers, only the first copy which appeared in the PDB file was kept. Only the Fv regions were kept from the Fab structures. Abnum (Abhinandan, K. R. & Martin, A. C. R. Analysis and improvements to Kabat and structurally correct numbering of antibody variable domains. *Mol. Immunol.* 45, 3832-3839 (2008)) was used to renumber the residues in the Fv structures according to Chothia numbering scheme (Al-Lazikani, B., Lesk, A.M. & Chothia, C. Standard conformations for the canonical structures of immunoglobulins. *J. Mol. Bio.* 273, 927-948 (1997)). Any structures with broken polypeptide CDR loops were discarded. Finally 1417 antibody Fv scaffold structures were kept for hotspots graft design (Supplementary Table 8).

Graft Nrf2 Hotspots onto Antibody Scaffold Structures

The residue-based triplet hashing method was implemented to search for the best antibody scaffold structures to graft the three Nrf2 hotspots onto, while maintaining the hotspots original interaction patterns with Keap1. We defined a 'residue triplet' as consisting of three virtual triangles that connected three residues' backbone Cα, N and C atoms, respectively. The triplet is characterised by nine vertexes (Vα1, Vα2, Vα3, VN1, VN2, VN3, VC1, VC2 and VC3, corresponding to the positions of nine backbone Cα, N, and C atoms of the three residues consisting of the triplet) and nine edges (Eα1, Eα2, Eα3, EN1, EN2, EN3, EC1, EC2 and EC3, corresponding to the edges from the three triangles). On the hotspots side, any three inverse rotamers were enumerated from the three Nrf2 hotspot residues (Glu79, Thr80, and Glu82) and compiled into a residue triplet. Each triplet was canonicalized by ensuring that the longest and second longest Cα edges always corresponded to Eα1 and Eα2, respectively. Each triplet was indexed into a unique string key by concatenating six edges' round-off (RO) lengths in order. For example, for a given triplet with Eα1=6.32, Eα2=4.67, Eα3=8.8, EN1=4.3, EN2=3.93, EN3=7.21, EC1=5.28, EC2=5.4 and EC3=9.82 the key is expressed as:

Key=Concatenate [RO(E)]=6594475510

All of the non-redundant index keys of hotspots' triplets were stored into a lookup table for fast access to corresponding hotspot triplet's information, including vertex residue types and atomic coordinates to facilitate later grafting onto the CDRs of antibody scaffold structures.

On the antibody scaffold side, any three CDR residues were enumerated and compiled into a triplet. The index key lookup table was generated in the same way as for hotspots triplet. To find the antibody scaffold structures which are able to accommodate the three hotspot residues in the geometrically matched positions in CDRs, the identical hotspots and antibody scaffold triplets were identified by directly comparing the respective index keys. The antibody scaffolds were grafted onto the hotspots by superimposing the scaffold triplet onto the corresponding identical hotspots one to minimise the RMSD between two sets of nine vertexes of the three triplet triangles. The three scaffold triplet residues were replaced with corresponding hotspots' ones by fitting the hotspots backbone atoms onto those of antibody triplet ones.

For each antibody designs obtained from hotspots graft, the sidechains of interfacial residues in antibody scaffolds clashing with Keap1 atoms were mutated into alanine to reduce clashes. The heavy-atom RMSD of the hotspots sidechain atoms before and after replacement was calculated. All residues were repacked and minimised using the Rosetta ppk.xml script. Several filters described below were applied to triage the designs:

The heavy-atom RMSD of the hotspots before and after replacement onto the antibody scaffold was smaller than 2.0 Å.

The buried solvent accessible surface area (SASA) upon binding was greater than 1200 Å (Hu, Z., Ma, B., Wolfson, H. & Nussinov, R. Conservation of polar residues as hot spots at protein interfaces. *Proteins* 39, 331-342 (2000).

Shape-complementarity (Sc) score was greater than 0.5.

The Rosetta ΔG score (binding energy) was lower than 0.0 REU.

The surviving designs that passed the filtering rules were finally ranked by Rosetta ΔG scores.

CDRH3 Loop Swap

The individual CDR loop's contributions to the Rosetta ΔG scores of G54.1 were calculated by truncating each CDR loop from the Fv region of modelled G54.1/Keap1 complex structure (FIG. 16). The Rosetta ΔG scores of each CDR truncation mutant were re-calculated. Individual CDR's contribution to binding was estimated by computing the Rosetta ΔG scores difference between each CDR truncation mutant and the original G54.1 antibody.

All the exogenous CDRH3 loops from the antibody scaffold crystal structures used in previous hotspots graft stage were dissected at the positions from $V_H93$ to $V_H103$ (according to Chothia numbering scheme) of Fv structures and labelled as the CDRH3 anchor residues. To graft an exogenous CDRH3 loop onto G54.1, the original CDRH3 loop of G54.1 was removed at the positions from $V_H94$ to $V_H102$, leaving $V_H93$ and $V_H103$ as the Fv anchor residues. Each exogenous CDRH3 loop was fitted onto the G54.1 Fv structure by superimposing the backbone atoms from two sets of anchor residues. The Fv anchor residues of G54.1 were later removed and the grafted exogenous CDRH3 loop was ligated onto G54.1 Fv by connecting the CDRH3 anchor residues with the neighbouring G54.1 residues ($V_H92$ and $V_H104$). The resulting structures were discarded if the backbone atoms of the new CDRH3 loop clashed with original G54.1/Keap1 complex structure. Any CDRH3 residue sidechains clashing with G54.1/Keap1 residues were mutated to alanine to reduce clashes. The final structures obtained from CDRH3 swap were repacked and minimised using Rosetta ppk.xml script as in Step 2 and ranked by Rosetta ΔG scores.

Rosetta Sequence Design

Two rounds of Rosetta sequence design were performed to optimise the binding affinities of the designed antibodies from hotspots graft and CDRH3 swap, respectively.

During the first round, starting from the five designed antibody structures that accommodated the three Nrf2 hotspots-mediated Keap1 interaction patterns, each interfacial CDR residue in the antibody side was mutated into other amino acid types (except cysteine, glycine and proline) to probe the mutation effect on Rosetta ΔG scores in order to identify mutants that were potentially able to improve the computed binding energies of designed antibodies with Keap1. The Rosetta script MutationScanPB.xml for computing change in binding free energy during in silico mutagenesis using the scoring function with the modified electrostatics scoring term was used to generate the single point mutants list. The point mutations were ranked by calculating the change of Rosetta ΔG scores, or, between each mutant and corresponding wild type structures. The top ranked single point mutations were selected and combined (maximum 5 mutations) to generate a variant of the original antibody graft.

During the second round, all residues of the swapped CDRH3 loops on G54.1 were allowed to mutate into all other amino acid types (excluding glycine, proline, and cysteine) simultaneously, with the backbone conformation of all interfacial residues on CDRs and Keap1 locally perturbed using backrub method, using the Rosetta flexbb-interfacedesign.xml script. Explicit electrostatics was not used in the scoring function. Three iterations of redesign and minimization were used to increase the likelihood that higher-affinity interactions could be found, starting with a soft-repulsive potential (soft rep weights), and ending with the default all-atom forcefield (score12 weights). Similar filter rules previously described for hotspots grafting designs were used to triage and rank the resulting CDRH3-swap designed structures:

The buried SASA upon binding was greater than 2000 Å.
The Rosetta ΔG score was lower than −20.0 REU.
Sc score was greater than 0.6.

Design Scoring

All the previously described computational features used for filtering or ranking the designs (Supplementary Table 2, 5) were calculated by Rosetta3.4 InterfaceAnalyzer application:

Rosetta ΔG score, or binding energy was defined as the difference between the total system energy in the bound and unbound states. In each state, interface residues were allowed to repack.
Rosetta total energy of the modelled complex structures.
Buried solvent accessible surface areas (SASAs) were defined as the difference between the total system SASAs in the bound and unbound states.
Shape-complementarity (Sc) score of the modelled antibody/Keap1 complex structures.
Buried unsaturated polar atoms.

Finally, 10 designs in 5 unique scaffolds after hotspots graft (Supplementary Table 3) and 19 CDRH3-swap variants of G54.1 were chosen for experimental testing (Supplementary Table 6).

Keap1 Expression & Purification

The gene encoding the Kelch domain of Keap1 was cloned into the expression vector pET-28a in frame with an N-terminal His tag and a TEV protease cleavage site. The construct was transformed into *E. Coli* strain BL21 (DE3), which was subsequently cultured in 2TY medium containing 25 ug/ml kanamycin at 37° C. Protein production was induced with 0.3 mM isopropyl β-D-1-thiogalactopyranoside (IPTG) at an O.D.600 of 4. Glycerol-based feed (50 mM MOPS, 1 mM MgSO4/MgCl2, 2% glycerol) was added to the culture immediately after addition of IPTG, and the cultured was incubated further at 17° C. overnight. Cells were harvested by centrifugation and lysed in a buffer containing 50 mM Tris pH8.5, 50 mM NaCl, 10% glycerol, 0.5% tritom-X100, 20 mM imidazole and sufficient amount of protease inhibitors (Roche). The lysate, pre-cleared by centrifugation, was filtered with a 0.2 μNI filter and then mixed with Ni-NTA beads (Qiagen). The beads were washed with 50 mM Tris pH8, 150 mM NaCl, 50 mM imidazole and 1 mM DTT before Keap1 was eluted with the former buffer supplemented with imidazole to a concentration of 250 mM. After the His tag was cut off, the sample was applied to a Ni-NTA (Qiagen) column to remove any Ni-binding contaminating proteins. The flow-through was collected and further purified by size exclusion (Superdex 75, GE Healthcare) and, if necessary, ion exchange (Mono Q, GE Healthcare) chromatography. The purified keap1 was concentrated and stored in 20 mM Tris pH7.5 and 5 mM DTT at −80° C.

Antibody Cloning & Expression

Heavy and light chain variable region genes designed in silico were chemically synthesized by DNA2.0, Inc. Transcriptionally active PCR (TAP) was employed to separately amplify the heavy and light chain variable regions and subsequently introduce DNA sequences encoding the hCMV promotor sequence, human γ1 $C_H1$ and $C_K$ (Km3 allotype) constant regions and poly(A) tail. The resultant constructs contained all of the required components for transient cellular expression. To generate Fab fragments for SPR analysis, HEK-293 cells were transiently transfected with TAP products using 293Fectin lipid transfection (Life Technologies, according to the manufacturer's instructions).

Crystallographic trials with the top four high affinity CDRH3-swap antibodies in Fab formats failed to yield diffraction-quality crystals in complex with Keap1. To convert LS146 from a Fab to a scFv construct, a gene encoding $V_H$ fused to $V_L$ through a $(Gly_4Ser)_4$ linker, a $His_{10}$ tag along with a TEV protease cleavage site was synthesized and cloned into a UCB proprietary expression vector by DNA2.0, Inc. The amino acid sequence of the gene product is given in Supplementary Table 10. CHO-S XE cells, a CHO-K1 derived cell line were transiently transfected with plasmid DNA using electroporation. Cells were removed by centrifugation and scFv-TEV-His tagged protein was purified by IMAC. Supernatant was filtered with a 0.2 uM filter and then loaded into a HisTrap excel column (GE healthcare). The column was washed with 50 mM Tris pH8, 150 mM NaCl, 45 mM imidazole before the antibody was eluted with 50 mM Tris pH8, 150 mM NaCl, 250 mM imidazole. After the His tag was removed, the sample was applied to the HisTrap excel column again to remove the Ni-binding contaminating proteins. The flowthrough was collected and further purified by size exclusion (Superdex 75, GE Healthcare) chromatography. Purified antibody was concentrated, in 50 mM HEPES pH7.5, 150 mM NaCl, 5% glycerol, and stored in aliquots at −80° C. until required.

Binding Analysis

Surface plasmon resonance (SPR) experiments were carried out on a Biacore 3000 system (GE Healthcare) using reagents from the same manufacturer. Fabs were captured on the surface of CM5 sensor chips via affinity purified goat polyclonal F(ab')$_2$ fragment specific to anti-human F(ab')$_2$ (Jackson 109-006-097). The latter was immobilised to the activated carboxymethyl dextran surface via amine coupling as follows: a fresh mixture of 50 mM N-hydroxysuccimide and 200 mM 1-ethyl-3-(3-dimethylaminopropyl)-carbodiimide was injected for 5 minutes at a flow rate of 10 μl/min, followed by 50 μg/ml anti-human F(ab')$_2$ in 10 mM acetate pH5.0 buffer for 5 min at the same flow rate. Finally the surface was deactivated with a 10 minute pulse of 1 M ethanolamine·HCl pH8.5. Reference flow cell was on the chip was prepared by omitting the protein from the above procedure, thus in the following experiments sensorgrams were obtained as the response unit difference between anti-F(ab')$_2$ and reference flow cells. Initial binding of Keap1 to expressed Fabs was assessed by injecting 50 μl supernatant, diluted 1 in 5 in running buffer, over the reference and anti-F(ab')$_2$ flow cells at a flow rate of 10 μl/min, followed by a 150 μl injection of 0, 500 or 5000 nM Keap1 in running buffer at a flow rate of 30 μl/min. After the dissociation phase lasting at least 5 min the chip surface was regenerated with two 60 sec pulses of 40 mM HCl interspersed with a 30 sec pulse of 5 mM NaOH at the same flow rate. Association and dissociation kinetics of Keap1 binding to captured Fabs were determined by the same protocol over at least 8 values of the following concentrations: 75, 100, 150, 250, 350, 500, 750, 1000, 1500, 2500, 3500 and 5000 nM. Zero Keap1 controls were interspersed between the former cycles in order to correct for baseline drift and sham transfected supernatant was assessed at each Keap1 concentration in order to determine and correct for non-specific binding of Keap1. Specificity of Fab binding to Keap1 was assessed by competition with a high-affinity Nrf2 peptide analogue, biotin-PEG-LQLDEETGEFLPIQ-amide (SEQ ID NO:74), corresponding to Nrf2 residues 74 to 87 that comprise the stronger Keap1 binding loop motif. Peptide Keap1 binding in the presence of peptide titrations to captured Fabs was followed using the above protocol. Using BIAevaluation™ software all sensorgrams were first transformed by subtracting a zero Keap1 control cycle and the corresponding non-specific control cycle prior to fitting dissociation and association kinetics. Dissociation constants ($K_D$) were estimated as the logarithmic mean of values measured over at least 6 Keap1 concentrations. $IC_{50}$ values were calculated using GraphPad Prism™ software by fitting to the log concentration versus normalized response/variable slope model represented by the following equation, where percent inhibition values for the three report points were treated as replicates at each concentration:

$$Y = \frac{100}{1 + 10^{[(logIC_{50}-X) \times S_{Hill}]}}.$$

Crystallisation

Keap1 was buffer exchanged to the storage buffer of LS146-scFv (50 mM HEPES pH7.5, 150 mM NaCl and 5% glycerol) prior to complex formation. This removed DTT from Keap1 storage buffer and prevented it from breaking the disulphide bonds in the antibody. Keap1 was then mixed with LS146-scFv at a molar ratio of 1:1.5 and incubated at room temperature for 30 minutes. The complex was purified by size exclusion chromatography (Superdex 75™ 26/60, GE Healthcare) and concentrated to 5 mg/ml. Initial crystallisation trials, with 200 nl protein solution plus 200 nl reservoir solution (Qiagen) in sitting-drop vapor-diffusion format, produced crystals in two conditions. Reproduction and optimization of one of the hit crystallization conditions (0.2 M sodium acetate and 20% PEG3500), using seed crystals obtained from the initial screening, generated diffraction quality crystals. The crystals were cryoprotected in mother liquor, supplemented with PEG 3350 to 35% (w/v), and vitrified in liquid nitrogen prior to data collection.

Crystallographic Data Collection and Processing

Datasets from crystals LS146-scFv/Keap1 complex was collected at the Diamond Light Source synchrotron facility (Didcot, United Kingdom) on beamline 104-1 at a wavelength of 0.917 Å. Molecular replacement was performed using program PHASER[9] in the CCP4 software suite[10,11] using Keap1 (PDB accession code 1X2J[12]), $V_H$ and $V_K$ frameworks without CDR loops (PDB accession code 3IVK[13]) as the models. See: McCoy, A. J. et al. *Phaser* crystallographic software. *J. Appl. Crystallogr.* 40, 658-674 (2007); Potterton, E., Briggs, P., Turkenburg, M., & Dodson, E. A graphical user interface to the CCP4 program suite. *Acta Crystallogr. Sect. D* 59, 1131-1137 (2003); Winn, M. D. et al. Overview of the CCP4 suite and current developments. *Acta Crystallogr. Sect. D* 67, 235-242 (2011); Padmanabhan, B. et al. Structural basis for defects of Keap1 activity provoked by its point mutations in lung cancer. *Mol. Cell* 3, 689-700 (2006); and Shechner, D. M. et al. Crystal Structure of the Catalytic Core of an RNA-Polymerase Ribozyme. *Science* 326, 1271-1275 (2009). The solvent content of the crystal was determined as 46.09% and there are two copied of complexes in an asymmetric unit. Solutions were found in three stages; positions of two copies of Keap1 were searched and obtained first, and then the two copies of heavy chains and the two light chains. Refinement and model building were carried out using Refmac5.4 (REFinement of MACromolecular structures) and COOT (Crystallography Object-Oriented Toolkit), respectively. The geometric quality of the final model was validated using Rampage, ProCheck, SFCheck, and the validation tools provided by the RCSB Protein Data Base. Data collection and refinement statistics for LS146-scFv/Keap1 is provided in Supplementary Table 11. See: Murshudov, G. N., Vagin, A. A. & Dodson, E. J. Refinement of macromolecular structures by the maximum-likelihood method. *Acta Cryst.* D53, 240-255 (1997); Emsley, P. & Cowtan, K. Coot: model-building tools for molecular graphics. *Acta Crystallogr. Sect. D* 60, 2126-2132 (2004); Lovell, C. Structure validation by Calpha geometry: phi,psi and Cbeta deviation. *Proteins* 50, 437-450 (2002). 17. Laskowski, R. A., MacArthur, M. W., Moss, D. S., & Thornton, J. M. PROCHECK: a program to check the stereochemical quality of protein structures. *J. Appl. Crystallogr.* 26, 283-291 (1993); and Vaguine, A. A., Richelle, J., & Wodak, S. J. SFCHECK: a unified set of procedures for evaluating the quality of macromolecular structure-factor data and their agreement with the atomic model. *Acta Crystallogr.* Sect. D 55, 191-205 (1999).

Additional Example—Computational Design of Novel Pan-TGFβ Blocking Antibody Fab Fragment by Transplanting Combined Hotspot Residues from Native TGFβ Receptors and a Known Anti-TGFβ Antibody Inspired by the success of antibody design targeting Keap1, we applied the same approaches on TGFβs to design a pan-specific anti-TGFβs antibody. TGFβ is widely expressed and has a multitude of different functions, including immune homeostasis and fibrosis regulation. TGFβs exist in a homodimer format and there are at least three homologous isoforms (TGFβ1, TGFβ2, and TGFβ3), which signal via the same receptors complex consisting of TGFβs dimer and three membrane receptors (TGFβR1, TGFβR2, and TGFβR3). TGFβR2 initially binds at the tip of the "fingers" on TGFβ and later recruits the other two receptors binding to the TGFβ dimer interface. The crystal complex structure of TGFβ1 and the extracellular domains of TGFβR1 and TGFβR2 have been solved. We attempted to design antibodies to bind at the same region as the two receptors do by transplanting five interfacial hotspot residues from two receptors, but unfortunately did not generate any experimentally validated binding. It was speculated that the receptors-inspired hotspots were not strong enough to fix the antibody scaffold templates at the desired binding site because the affinities of hotspot donors, the TGFβ receptors, are very weak ($K_D$ values of 2.5 and 0.4 µM for TGFβR1 and TGFβR2, respectively). Fresolimumab (GC-1008) is a pan-TGFβ blocking antibody with low-nanomolar affinities. The crystal structure of Fresolimumab in complex with TGFβ3 reveals that the epitopes of Fresolimumab are highly overlapped with the receptors binding sites. So it is presumed by mixing the hotspot residues from both two receptors and Fresolimumab as combined query will increase the chance to generate an antibody binder binding at the same region.

Five residues from receptor 1&2 and 9 residues from Fresolimumab were selected by virtual alanine scanning and used as the mixed query hotspots. It is noted that our hotspots transplant approach is based on residue triplet hashing that each time only three out of the 14 hotspot residues are transplanted first to determine an orientation for the given antibody templates, on which the rest of the hotspots are transplanted by checking if their backbone atoms' positions are close to those of any residues on the orientation of the antibody template fixed by the current hotspots triplet. After hotspots transplant, the residues on CDR loops of the antibody templates are mutated by Rosetta to generate new sequences to stabilize the current transplant and orientation using the same method aforementioned in the Keap1 case. Given that the highly homologous of the three TGFβs at the receptors binding site, only TGFβ1 structure from the complex with TGFβR1 and TGFβR2 was used as the antigen target to calculate the Rosetta binding energy for each designed antibody Fab structural model.

The affinities of the designed antibodies Fab fragments were measured using Biacore aforementioned. Only one designed Fab shows obvious affinities against TGFβ1 and TGFβ3 ($K_D$s are 106 and 32.9 nM, respectively), and much weaker affinity against TGFβ2 (the biding curves were difficult to fit). The affinities are much weaker than those of the reference antibody Fresolimumab, but are slightly stronger than those of the receptors. To test if the designed antibody is able to block the receptors' binding and disrupt the initiated downstream signalling, a cellular reporter gene assay driven by TGFβs binding was developed to determine the blocking efficacy of the designed antibody. It is demonstrated that upon antibody binding, the downstream signalling initiated by all three TGFβs binding with the corresponding receptors were partly disrupted in a concentration-dependent manner. The $IC_{50}$s were determined and displayed a correlation with the $K_D$s from biophysical binding assay. It is indicated that the designed antibody Fab, though presenting weak affinities, is probably binding at the region overlapping with receptors and Fresolimumab's epitopes, and therefore blocks the receptors binding as expected in a pan-specific manner.

The complex of the designed Fab with TGFβ1 was crystallized and the structure was solved. As predicted, the Fab completely occupies both receptors binding site on TGF β1, and overlaid very well with the predicted binding pose. The heavy chain of the antibody occupies majority of the binding site using hydrophobic residues, including CDR H2 and H3 hosting four hotspot residues from the receptors and Fresolimumab.

Supplementary Table 12 shows binding affinities of the ordered antibody Fab designs from hotspots graft. Dissociation constants ($K_D$) were determined by SPR.

Supplementary Table 13 shows Fv regions' amino acid sequences of ordered antibody designs from hotspots graft.

Supplementary Table 14 shows pan-blocking $IC_{50}$s of Fab 184 design from hotspots graft in the reporter gene assay (n=2).

FIGS. 34-37 depict pan-TGFb blocking Fab fragment design by transferring combined receptors- and Fresolimumab-inspired hotspot residues: FIG. 34—Combined hotspot residues from TGFβR1 & 2 and Fresolimumab; FIG. 35—SPR kinetics profiles for Fab184/TGFβs complexes with designed antibody Fab immobilized on the chips; FIG. 36—Neutralisation of TGFβs-receptors binding by titration of Fab184 TGFβs in HEK Blue reporter gene cell assay; and FIG. 37—Comparison of the binding modes of crystal Fab184 with modelled one by superimposing onto the TGFβ1 side.

Supplementary Tables

SUPPLEMENTARY TABLE 1

Nrf2 Hotspots identification by in silico alanine scanning.

| Nrf2 residue | Change of Rosetta ΔG scores upon in silico alanine mutation (REU) | Note |
|---|---|---|
| Glu 78 | 0.74 | Not used due to sidechain missing in the crystal structure |
| Glu 79 | 3.15 | Strong hotspot, hydrogen bonds with Keap1 R415 and R433 |
| Thr 80 | 0.95 | Weak hotspot |
| Gly 81 | 34.08 | Not suitable for hotspot without sidechain |
| Glu 82 | 3.11 | Strong hotspot, hydrogen bonds with Keap1 S363, R380, and N382 |
| Phe 83 | 0.01 | Non-hotspot |
| Leu 84 | 0.24 | Non-hotspot |

SUPPLEMENTARY TABLE 2

Computational features of ordered antibody designs from hotspots graft.

| Design | Rosetta ΔG (REU) | Rosetta total energy (REU) | Buried SASA (Å$^2$) | Shape complementarity | Buried unsaturated polar atoms |
|---|---|---|---|---|---|
| G53 | −14.6 | −854.4 | 2276 | 0.59 | 15 |
| G53.1 | −20.8 | −989.4 | 2175 | 0.57 | 14 |
| G54 | −16.8 | −815.6 | 2514 | 0.61 | 9 |
| G54.1 | −32.3 | −993.1 | 2583 | 0.58 | 4 |
| G55 | −15.6 | −981.1 | 1453 | 0.57 | 3 |
| G55.1 | −19.7 | −1089.8 | 1352 | 0.51 | 2 |
| G56 | −14.2 | −973.7 | 1894 | 0.55 | 10 |
| G56.1 | −23.3 | −1074.2 | 1650 | 0.53 | 3 |
| G85 | −15.8 | −791.0 | 2624 | 0.59 | 19 |
| G85.1 | −19.5 | −938.4 | 2706 | 0.56 | 19 |

SUPPLEMENTARY TABLE 3

Fv regions' amino acid sequences of ordered antibody designs from hotspots graft.

| Design | SEQ ID NO: | Sequence $V_H$ | Sequence $V_L$ | SEQ ID NO: |
|---|---|---|---|---|
| G53 | 01 | QVQLQESGPGLMKPSETLSLTCSVSGDSIAADYWSWIRKPPGKGLEYIG YVSETGETYYNPSLKSRVTISVDASKNRFSLNLNSVTAADTAVYYCARW DGDYWGQGILVTVSS | EIVMTQSPATLSVSPGERATLSCRASQSIGNNLHWYQQ KPGQAPRLLIYYASQSISGIPARFSSGSGSGTEFTLTI SSLQSEDFAVYYCQQANSWPYTFGGGTKVEIK | 02 |

SUPPLEMENTARY TABLE 3-continued Fv regions' amino acid sequences of ordered antibody designs from hotspots graft.

| Design | SEQ ID NO: $V_H$ | Sequence $V_H$ | $V_L$ | SEQ ID NO: $V_L$ |
|---|---|---|---|---|
| G53.1 | 03 | VQLQESGPGLMKPSETLSLTCSVSGDSIAADYWSWIRKPPGKGLEYIG YVDETGETYYNPSLKSRVTISVDASKNRFSLNLNSVTAADTAVYYCARW DGDYWGQGILVTVSS | EIVMTQSPATLSVSPGERATLSCRASQSIGNNLHWYQQ KPGQAPRLLIYYASQSISGIPARFSSGSGSGTEFTLTI SSLQSEDFAVYYCQQANSWPYTFGGGTKVEIK | 04 |
| G54 | 05 | EVQLVESGGGLVQPGGSLRLSCAASGFAISASSIHWVRQAPGKGLEWV ASISPETGETYYADSVAGRFTISADTKNTAYLQMNSLRAEDTAVYYCA RQGYAARSGAGFDYWGQGTLVTVSS | DIQMTQSPSSLSASVGDRVTITCRASQSVSSAVAWYQQ KPGKAPKLLIYSASSLVSGVPSRFSGSRSGTDFTLTIS SLQPEDFATYYCQQSYSFPSTFGQGTKVEIK | 06 |
| G54.1 | 07 | EVQLVESGGGLVQPGGSLRLSCAASGFAISASSIHWVRQAPGKGLEWV ASIDPETGETYYADSVAGRFTISADTKNTAYLQMNSLRAEDTAVYYCA RQGYAARSGAGFDYWGQGTLVTVSS | DIQMTQSPSSLSASVGDRVTITCRASQSVSSAVAWYQQ KPGKAPKLLIYSASSLVSGVPSRFSGSRSGTDFTLTIS SLQPEDFATYYCQQSYSFPSTFGQGTKVEIK | 08 |
| G55 | 09 | EVQLVESGGGLIRPGGSLRLSCKGSGFIFENFGFGWVRQAPGKGLEWV SGTNWNGGDSRYGDSVKGRFTISRDNSNNFVYLQMNSLRPERDTAIVY CARGTDYTIDETGERYQGSGTFWYFDVWGRGTLVTVSS | EIVLTQSPDTLSLSPGERATLSCRASQSVHSRYFAWYQHK PGQPPRLLIYGGSTRATGIPNRSFAGGSGTOFTLTVNRLE AEDFAVVYCQQYGASPYTFGQGTKVEIR | 10 |
| G55.1 | 11 | EVQLVESGGGLIRPGGSLRLSCKGSGFIFENFGFGWVRQAPGKGLEWV SGTNWNGGDSRYGDSVKGRFTISRDNSNNFVYLQMNSLRPERDTAIVY CARGTDYTIDETGERYQGSGTFWYFDVWGRGTLVTVSS | EIVLTQSPDTLSLSPGERATLSCRASQSVHSRYFAWYQHK KPQPPRLLIYGGSTRATGIPNRSFAGGSGTOFTLTVNRL EAEDFAVVYCQQYGASPYTFGQGTKVEIR | 12 |
| G56 | 13 | EVQLVESGGGLIRPGGSLRLSCKGSGFIFENFGFGWVRQAPGKGLEWV SGTNWNGGDSRYGDSVKGRFTISRDNSNNFVYLQMNSLRPERDTAIVY CARGTDYTIDETGERYQGSGTFWYFDVWGRGTLVTVSS | EIVLTQSPATLSVSPGERATLSCRASQSVHSRYFAWYQQ KRGQPQSPRLLIYGGSTRATGIPNRSFAGGSGTOFTLTI TRVEPEDFAVVYCQQYGASPYTFGQGTKVELR | 14 |
| G56.1 | 15 | EVQLVESGGGLIRPGGSLRLSCKGSGFIFENFGFGWVRQAPGKGLEWV SGTNWNGGDSRYGDSVKGRFTISRDNSNNFVYLQMNSLRPERDTAIVY CARGTDYTIDETGERYQGSGTFWYFDVWGRGTLVTVSS | EIVLTQSPATLSVSPGERATLSCRASQSVHSRYFAWYQQ KRGQPQSPRLLIYGGSTRATGIPNRSFAGGSGTOFTLTI TRVEPEDFAVVYCQQYGASPYTFGQGTKVELR | 16 |
| G85 | 17 | QVQLVQSGAEVKKPGSSVKVSCKASGGTAAAYAINWVRQAPGQGLE WMGNIEPETGEANYAQKFAGRVTITADESTSTAYMELSSLRSEDTAVY YCARYFMSYKHLSDYWGQGTLVTVSS | DIALTQPASVSGSPGQSITISCTGTSSDVGSNNYVSWYQ QHPGKAPKLMIYGGSNRPGVSNRFSGSKSGNTASLTIS GLQAEDEADYYCRSWQSAAAYSVFGGGTKLTVL | 18 |
| G85.1 | 19 | QVQLVQSGAEVKKPGSSVKVSCKASGGTAAAYAINWVRQAPGQGLE WMGNIEPETGEANYAQKFAGRVTITADESTSTAYMELSSLRSEDTAVY CARYFMSYKHLSDYWGQGTLVTVSS | DIALTQPASVSGSPGQSITISCTGTSSDVGSNNYVSWYQ QHPGKAPKLMIYGGSNRPGVSNRFSGSKSGNTASLTIS GLQAEDEADYYCRSWQSAAAYSVFGGGTKLTVL | 20 |

SUPPLEMENTARY TABLE 4

Binding affinities of the ordered antibody Fab designs from hotspots graft. Dissociation constants ($K_g$) were determined by SPR.

| Design | Scaffold[1] | Hotspots positions | #Mutations from scaffolds (except grafted hotspots) | Fraction of Fab binding sites occupied @ 500 nM Keap1[3] | $k_{on}$ ($M^{-1}s^{-2}$) | $k_{off}$ ($s^{-1}$) | $K_g$ (nM) | $K_g$ 95% CI[4] |
|---|---|---|---|---|---|---|---|---|
| G53 | 2YSS[a] | $V_H$53E, $V_H$54T, | 3 | 0.002 | ND[2] | ND | ND | ND |
| G53.1 | | $V_H$56E | 5 | 0.0009 | ND | ND | ND | ND |
| G54 | 3IVK[b] | $V_H$53E, $V_H$54T, | 6 | 0.01 | ND | ND | ND | ND |
| G54.1 | | $V_H$56E | 9 | 0.468 | $2.1 \times 10^5$ | $2.6 \times 10^{-2}$ | 126 | 110-143 |
| G55 | 3TCL[c] | $V_H$102E, | 1 | 0.015 | ND | ND | ND | ND |
| G55.1 | | $V_H$102$^4$T, $V_H$102$^C$E | 3 | 0.016 | ND | ND | ND | ND |
| G56 | 3U4B[d] | $V_H$102E, | 1 | 0.023 | ND | ND | ND | ND |
| G56.1 | | $V_H$102$^4$T, $V_H$102$^C$E | 2 | 0.027 | ND | ND | ND | ND |
| G85 | 2JB5[e] | $V_H$54E, | 6 | 0.179 | $2.3 \times 10^5$ | $4.9 \times 10^{-2}$ | 236 | 137-405 |
| G85.1 | | $V_H$55T, $V_H$57E | 7 | 0.171 | $6.8 \times 10^4$ | $2.3 \times 10^4$ | 341 | 209-555 |

[1]Original antigens in the PDB structures: [a]Hen Lysozyme; [b]RNA fragment; [c,d]HIV-1 Envelope Glycoprotein Gp120; [e]Diagnostic dye molecule.
[2]ND: Not determined.
[3]Limit if detection = 0.008
[4]95% confidence intervals of $K_D$

SUPPLEMENTARY TABLE 5

Computational features of ordered CDRH3-swap variants of G54.1.

| Design | Rosetta ΔG (REU) | Rosetta total energy (REU) | Buried SASA (Å²) | Shape complementarity | Buried unsaturated polar atoms |
|---|---|---|---|---|---|
| 171 | −43.24 | −1063.6 | 2590 | 0.63 | 14 |
| 145 | −46.25 | −1058.7 | 2734 | 0.65 | 10 |
| 168 | −46.4 | −1063.0 | 2656 | 0.64 | 15 |
| 146 | −45.6 | −1080.4 | 2663 | 0.63 | 12 |
| 142 | −46.9 | −1071.0 | 2628 | 0.65 | 8 |
| 153 | −45.5 | −1080.5 | 2548 | 0.65 | 9 |
| 144 | −45.1 | −1976.5 | 2618 | 0.67 | 10 |
| 143 | −45.1 | −1554.6 | 2643 | 0.65 | 11 |
| 151 | −46.8 | −1085.5 | 2557 | 0.65 | 13 |
| 149 | −39.5 | −1054.5 | 2615 | 0.6 | 5 |
| 147 | −43.3 | −1068.8 | 2512 | 0.64 | 7 |
| 152 | −41.7 | −1040.1 | 2497 | 0.66 | 12 |
| 150 | −38.2 | −1065.6 | 2507 | 0.62 | 8 |
| 169 | −41.5 | −1060.5 | 2429 | 0.63 | 9 |
| 175 | −43.3 | −1071.3 | 2588 | 0.64 | 9 |
| 174 | −43.5 | −1060.1 | 2335 | 0.67 | 10 |
| 148 | −43.6 | −1066.3 | 3645 | 0.66 | 9 |
| 170 | −43.4 | −1073.7 | 2498 | 0.67 | 10 |
| 173 | −45.9 | −1083.4 | 2680 | 0.61 | 10 |

SUPPLEMENTARY TABLE 6

Fv regions' amino acid sequences of ordered CDRH3-swap variants of G54.1.
All CDRH3-swap $V_L$ sequences are identical to that of G54.1.

| Design | SEQ ID NO: | $V_H$ sequence |
|---|---|---|
| 171 | 21 | EVQLVESGGGLVQPGGSLRLSCAASGFAISASSIHWVRQAPGKGLEWVASIDPETGETLYAKSVAGRFTISADTSKNTAYLQMNSLRAEDTAVYYCVAPRVDLYAADAWGQGTLVTVSS |
| 145 | 22 | EVQLVESGGGLVQPGGSLRLSCAASGFAISASSIHWVRQAPGKGLEWVASIDPETGETLYAKSVAGRFTISADTSKNTAYLQMNSLRAEDTAVYYCVRRAAAKDWGVAAAYWGQGTLVTVSS |
| 168 | 23 | EVQLVESGGGLVQPGGSLRLSCAASGFAISASSIHWVRQAPGKGLEWVASIDPETGETLYAKSVAGRFTISADTSKNTAYLQMNSLRAEDTAVYYCAGLLWSWGGAGSWGQGGTLVTVSS |
| 146 | 24 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARAYAGDGVYYADVWGQGTLVTVSS |
| 142 | 25 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARWGYEPYAMAMDYWGQGTLVTVSS |
| 153 | 26 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARMPAWGSADYWGQGTLVTVSS |
| 144 | 27 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARSAASDAAYAANVWGQGTLVTVSS |
| 143 | 28 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARGEWFYGALSDYAGQGTLVTVSS |
| 151 | 29 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARRTASDGRAAMDYWGQGTLVTVSS |
| 149 | 30 | EVQLVESGGGLVQPGGSLRLSCAASGFAISASSIHWVRQAPGKGLEWVASIDPETGETLYAKSVAGRFTISADTSKNTAYLQMNSLRAEDTAVYYCSRGQYGDATDYWGQGTLVTVSS |
| 147 | 31 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARRGDYGSWSFAYWGQGTLVTVSS |
| 152 | 32 | EVQLVESGGGLVQPGGSLRLSCAASGFAISASSIHWVRQAPGKGLEWVASIDPETGETLYAKSVAGRFTISADTSKNTAYLQMNSLRAEDTAVYYCAILGAWGANAGGGMDVWGQGTLVTVSS |
| 150 | 33 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARERAEYASDAAWGQGTLVTVSS |
| 169 | 34 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARAESGNVAAADYWGQGTLVTVSS |
| 175 | 35 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARCRAASAYAADAAGQGTLVTVSS |
| 174 | 36 | EVQLVESGGGLVQPGGSLRLSCAASGFAISASSIHWVRQAPGKGLEWVASIDPETGETLYAKSVAGRFTISADTSKNTAYLQMNSLRAEDTAVYYCTRAHAYGLDYWGQGTLVTVSS |
| 148 | 37 | EVQLVESGGGLVQPGGSLRLSCAASGFAISASSIHWVRQAPGKGLEWVASIDPETGETLYAKSVAGRFTISADTSKNTAYLQMNSLRAEDTAVYYCAREGKWWAYFDAWGQGTLVTVSS |
| 170 | 38 | EVQLVESGGGLVQPGGSLRLSCAASGFAISASSIHWVRQAPGKGLEWVASIDPETGETLYAKSVAGRFTISADTSKNTAYLQMNSLRAEDTAVYYCARDNGRARATAAYAGQGTLVTVSS |

SUPPLEMENTARY TABLE 6-continued

Fv regions' amino acid sequences of ordered CDRH3-swap variants of G54.1.
All CDRH3-swap $V_L$ sequences are identical to that of G54.1.

| Design | SEQ ID NO: | $V_H$ sequence |
|---|---|---|
| 173 | 39 | EVQLVESGGGLVQPGGSLRLSCAASGFAISASSIHWVRQAPGKGLEWVASIDPETGETLYAKSVAGRFTISADTSKNTAYLQMNSLRAEDTAVYYCAREYAWWYAAADYWGQGTLVTVSS |

SUPPLEMENTARY TABLE 7

Binding affinities of ordered antibody Fab fragments of CDRH3-swap variants of G54.1. Dissociation constants ($K_D$) were determined by SPR.

| Design | CDRH3 donor[1] | CDRH3 length | #Mutations from original CDRH3 donor | $k_{on}$ ($M^{-1}s^{-2}$) | $k_{off}$ ($s^{-1}$) | $K_D$ (nM) | $K_D$ 95% CI |
|---|---|---|---|---|---|---|---|
| 171 | 2VDO | 10 | 6 | $2.4 \times 10^5$ | $9.0 \times 10^{-2}$ | 4.1 | 3.2-5.3 |
| 145 | 2R0Z | 13 | 8 | $2.1 \times 10^5$ | $1.1 \times 10^{-3}$ | 5.4 | 4.9-5.9 |
| 168 | 1ND0 | 10 | 2 | $2.7 \times 10^5$ | $2.5 \times 10^{-3}$ | 3.5 | 8.5-10.4 |
| 145 | 3DET | 12 | 5 | $2.7 \times 10^5$ | $5.2 \times 10^{-3}$ | 19.6 | 18.6-20.5 |
| 142 | 1ISC | 11 | 3 | $2.3 \times 10^5$ | $1.1 \times 10^{-3}$ | 47 | 45-50 |
| 153 | 4HWE | 9 | 2 | $3.5 \times 10^5$ | $1.9 \times 10^{-2}$ | 54 | 50-58 |
| 144 | 2OSL | 12 | 9 | $3.2 \times 10^5$ | $2.9 \times 10^{-2}$ | 93 | 80-107 |
| 143 | 1NC0 | 11 | 5 | $3.2 \times 10^5$ | $3.1 \times 10^{-2}$ | 99 | 83-118 |
| 151 | 3TT1 | 12 | 4 | $3.1 \times 10^5$ | $3.1 \times 10^{-2}$ | 103 | 95-111 |
| 175 | 3U9P | 11 | 4 | $1.8 \times 10^5$ | $2.0 \times 10^{-3}$ | 110 | 87-139 |
| 149 | 3NTC | 9 | 5 | $3.9 \times 10^5$ | $4.4 \times 10^{-2}$ | 113 | 105-122 |
| 147 | 3GK8 | 11 | 3 | $1.1 \times 10^5$ | $1.3 \times 10^{-2}$ | 119 | 98-143 |
| 152 | 3UJJ | 15 | 2 | $8.6 \times 10^4$ | $1.0 \times 10^{-2}$ | 119 | 112-126 |
| 150 | 3SQO | 9 | 3 | $3.4 \times 10^5$ | $4.1 \times 10^{-2}$ | 122 | 104-143 |
| 169 | 2ADG | 11 | 4 | $2.0 \times 10^5$ | $2.4 \times 10^{-2}$ | 123 | 96-160 |
| 174 | 3E8U | 8 | 3 | $2.8 \times 10^5$ | $3.3 \times 10^{-2}$ | 125 | 87-183 |
| 148 | 3KYK | 10 | 5 | $4.5 \times 10^5$ | $7.1 \times 10^{-2}$ | 160 | 129-199 |
| 170 | 2V17 | 11 | 2 | $1.6 \times 10^5$ | $5.0 \times 10^{-3}$ | 393 | 294-524 |
| 173 | 3DVN | 11 | 3 | $2.4 \times 10^5$ | $9.5 \times 10^{-2}$ | 413 | 283-601 |

[1]PDB antibody structures of the exogenous CDRH3 loops

SUPPLEMENTARY TABLE 8

Structural $V_H/V_L$ orientation analysis using Abangle[18]. Two reference frame planes are mapped onto Fv structures. $V_H/V_L$ orientation is described as equivalent to measuring the orientation between the two planes by defining a vector C and three points on each plane as described in 18.

| Structure | $HL_{tension}(°)$[1] | $HC1_{bead}(°)$[5] | $LC1bead(°)$[3] | $HC2bead(°)$[4] | $LC1_{bead}(°)$[5] | dc(Å)[3] |
|---|---|---|---|---|---|---|
| Fab-LS146 model | −56.50 | 71.59 | 123.30 | 118.94 | 79.80 | 16.06 |
| scFv-LS146 X-ray structure | −66.89 | 71.89 | 120.40 | 117.29 | 81.48 | 16.10 |

[1]torsion angle between H1 and L1;
[2]bend angle between H1 and C;
[3]bend angle between H2 and C;
[4]bend angle between L1 and C;
[5]bend angle between L2 and C;
[6]length of C.

SUPPLEMENTARY TABLE 9

List of antibody V-region scaffold structures used in this study for hotspots graft design. Each scaffold is designated as: PDB + "_" + $V_H$ chain ID + $V_L$ chain ID.

| | | | | | | | | |
|---|---|---|---|---|---|---|---|---|
| 12e8_HL | 15c8_HL | 1a14_HL | 1a2y_BA | 1a31_HL | 1a3r_HL | 1a4j_BA | 1a4k_BA | 1a6t_BA | 1a6u_HL |
| 1a6v_HL | 1a6w_HL | 1a7n_HL | 1s7o_HL | 1a7p_HL | 1a7q_HL | 1a7r_HL | 1acy_HL | 1ad0_BA | 1ad9_BA |
| 1adq_HL | 1ae6_HL | 1afv_HL | 1ahw_BA | 1ail_HL | 1aif_BA | 1aj7_HL | 1ap2_BA | 1aqk_HL | 1arl_CD |
| 1axs_HL | 1axt_HL | 1ay1_HL | 1b2w_HL | 1b4j_HL | 1baf_HL | 1bbd_HL | 1bbj_BA | 1bey_HL | 1bfo_BA |
| 1bfv_HL | 1bgx_HL | 1bj1_HL | 1bln_HL | 1bog_BA | 1bq1_HL | 1bvk_HL | 1bvl_AB | 1bz7_BA | 1c08_BA |
| 1c12_BA | 1c1e_HL | 1c5b_HL | 1c5c_HL | 1c5d_BA | 1cbv_HL | 1ce1_HL | 1cf8_HL | 1cfn_BA | 1cfq_BA |
| 1cfs_BA | 1cft_BA | 1cfv_HL | 1cgs_HL | 1cic_BA | 1ck0_HL | 1c17_HL | 1clo_HL | 1cly_HL | 1clz_HL |

SUPPLEMENTARY TABLE 9-continued

List of antibody V-region scaffold structures used in this study for hotspots graft design. Each scaffold is designated as: PDB + "_" + $V_H$ chain ID + $V_L$ chain ID.

| | | | | | | | | | |
|---|---|---|---|---|---|---|---|---|---|
| 1cr9_HL | 1ct8_BA | 1cu4_HL | 1cz8_HL | 1d5b_BA | 1d5i_HL | 1d6v_HL | 1dba_HL | 1dbb_HL | 1dbj_HL |
| 1dbk_HL | 1dbm_HL | 1dee_BA | 1dfb_HL | 1d17_HL | 1dlf_HL | 1dn0_BA | 1dqd_HL | 1dqj_BA | 1dql_HL |
| 1dqm_HL | 1dqq_BA | 1dsf_HL | 1dvf_BA | 1dzb_Aa | 1e4w_HL | 1e4x_HL | 1e6j_HL | 1e6o_HL | 1eap_BA |
| 1egj_HL | 1ehl_HL | 1ejo_HL | 1emt_HL | 1eo8_HL | 1ecz_BA | 1ezv_XY | 1fl1_BA | 1f3d_HL | 1f3r_Bb |
| 1f4w_HL | 1f4x_HL | 1f4y_HL | 1f58_HL | 1f8t_HL | 1f90_HL | 1fai_HL | 1fbi_HL | 1fdl_HL | 1fe8_HL |
| 1fgn_HL | 1fig_HL | 1fj1_HL | 1fl3_AB | 1fl5_HL | 1fl6_BA | 1fn4_DC | 1fns_HL | 1for_HL | 1fpt_HL |
| 1frg_HL | 1fsk_CB | 1fvc_BA | 1fvd_BA | 1fve_BA | 1g7h_BA | 1g7i_BA | 1g7j_BA | 1g7l_BA | 1g7m_BA |
| 1g9m_HL | 1g9n_HL | 1gaf_HL | 1gc1_HL | 1ggb_HL | 1ggc_HL | 1ggi_HL | 1ghf_HL | 1gig_HL | 1gpo_HL |
| 1h0d_BA | 1h3p_HL | 1h8n_aA | 1h8o_aA | 1h8s_aA | 1hez_BA | 1hh5_BA | 1hh9_BA | 1hi6_BA | 1hil_BA |
| 1him_LH | 1hin_HL | 1hkl_HL | 1hq4_BA | 1hys_DC | 1hzh_HL | 1i3g_HL | 1i7z_BA | 1i8i_BA | 1i8k_BA |
| 1i8m_BA | 1i9i_HL | 1i9j_HL | 1i9r_HL | 1iai_HL | 1ibg_HL | 1ic4_HL | 1ic5_HL | 1ic7_HL | 1ifh_HL |
| 1igc_HL | 1igf_HL | 1igi_HL | 1igj_BA | 1igm_HL | 1igc_BA | 1igy_BA | 1ikf_HL | 1ili_AB | 1ind_HL |
| 1ine_HL | 1iqd_BA | 1iqv_HL | 1it9_HL | 1j05_BA | 1j1o_HL | 1j1p_HL | 1j1x_HL | 1j5o_HL | 1jfq_HL |
| 1jgu_HL | 1jgv_HL | 1jhl_HL | 1jn6_BA | 1jnh_BA | 1jnl_HL | 1jnn_HL | 1jp5_aA | 1jps_HL | 1jpt_HL |
| 1jrh_HL | 1jv5_BA | 1k4c_AB | 1k4d_AB | 1k6q_HL | 1kb9_JK | 1kb5_HL | 1kc5_HL | 1kcr_HL | 1kcs_HL |
| 1kcu_HL | 1kcv_HL | 1keg_HL | 1kel_HL | 1kem_HL | 1ken_HL | 1kfa_HL | 1kip_BA | 1kiq_BA | 1kir_BA |
| 1kn2_HL | 1kn4_HL | 1kno_BA | 1ktr_HL | 1kyo_JK | 1l7i_HL | 1l7t_HL | 1lk3_HL | 1lo0_HL | 1lo2_HL |
| 1lo3_HL | 1lo4_HL | 1m7d_BA | 1m7i_BA | 1mam_HL | 1mco_HL | 1mcp_HL | 1mex_HL | 1mf2_HL |
| 1mfa_HL | 1mfb_HL | 1mfc_HL | 1mfd_HL | 1mfe_HL | 1mh5_BA | 1mhh_BA | 1mhp_HL | 1mim_HL | 1mj8_HL |
| 1mjj_BA | 1mju_HL | 1mlb_BA | 1mlc_BA | 1mnu_HL | 1mpa_HL | 1mqk_HL | 1mvu_BA | 1n0x_HL | 1n4x_HL |
| 1n5y_HL | 1n64_HL | 1n6q_HL | 1n7m_LH | 1n8z_BA | 1nak_HL | 1nbv_HL | 1nby_BA | 1nbz_BA | 1nc2_BA |
| 1nc4_BA | 1nca_HL | 1nch_HL | 1ncc_HL | 1ncd_HL | 1ncw_HL | 1nd0_BA | 1ndg_BA | 1ndm_BA | 1nfd_FE |
| 1ngp_HL | 1ngq_HL | 1ngw_BA | 1ngx_BA | 1ngy_BA | 1ngz_BA | 1nj9_BA | 1n10_HL | 1n1b_HL | 1n1d_HL |
| 1nms_HL | 1nmb_HL | 1nmc_BC | 1nsn_HL | 1oak_HL | 1oaq_HL | 1oar_HL | 1oau_HL | 1oax_HL | 1oay_HL |
| 1oaz_HL | 1obl_BA | 1ocw_HL | 1om3_HL | 1op3_HL | 1op5_HL | 1opg_HL | 1orq_BA | 1ors_BA | 1osp_HL |
| 1ots_CD | 1ott_CD | 1otu_CD | 1p2c_BA | 1p4b_HL | 1p4i_HL | 1p7k_BA | 1p84_JK | 1pg7_HL | 1pkq_BA |
| 1plg_HL | 1psk_HL | 1pz5_BA | 1q0x_HL | 1q0y_HL | 1q1j_HL | 1q72_HL | 1q9k_BA | 1q9l_BA | 1q9o_BA |
| 1q9w_BA | 1qbl_HL | 1qbm_HL | 1qfu_HL | 1qfw_IM | 1qkz_HL | 1qle_HL | 1qlr_BA | 1qnz_HL | 1qok_aA |
| 1qyg_HL | 1r0a_HL | 1r24_BA | 1r3i_HL | 1r3j_BA | 1r3k_BA | 1r3l_BA | 1rfd_HL | 1rhh_BA | 1rih_HL |
| 1riu_HL | 1riv_HL | 1rjl_BA | 1rmf_HL | 1ru9_HL | 1rua_HL | 1ruk_HL | 1rul_HL | 1rum_HL | 1rup_HL |
| 1ruq_HL | 1rur_HL | 1rvf_HL | 1rz7_HL | 1rz8_BA | 1rzj_HL | 1rzk_HL | 1s3k_HL | 1s5h_BA | 1s5i_HL |
| 1s78_DC | 1sbs_HL | 1seq_HL | 1sm3_HL | 1svz_aA | 1sy6_HL | 1t03_HL | 1t04_BA | 1t2q_HL | 1t3f_BA |
| 1t4k_BA | 1t66_DC | 1tet_HL | 1tjg_HL | 1tjh_HL | 1tji_HL | 1tpx_BC | 1tqb_BC | 1tqc_BC | 1tzg_HL |
| 1tzh_BA | 1tzi_BA | 1u6a_HL | 1u8h_BA | 1u8i_BA | 1u8j_BA | 1u8k_BA | 1u8l_BA | 1u8m_BA | 1u8n_BA |
| 1u8o_BA | 1u8p_BA | 1u8q_BA | 1u91_BA | 1u92_BA | 1u93_BA | 1u95_BA | 1ua6_HL | 1uac_HL | 1ub5_AB |
| 1ub6_AB | 1ucb_HL | 1uj3_BA | 1um4_HL | 1um5_HL | 1um6_HL | 1uwe_HL | 1uwg_HL | 1uwx_HL | 1uyw_HL |
| 1uz6_FE | 1uz8_BA | 1v7m_HL | 1v7n_HL | 1vfa_BA | 1vfb_BA | 1vge_HL | 1vpo_HL | 1w72_HL | 1wc7_BA |
| 1wcb_BA | 1wej_HL | 1wt5_AC | 1wzl_HL | 1x9q_aA | 1xcq_BA | 1xct_BA | 1xft_BA | 1xf3_BA | 1xf4_BA |
| 1xf5_BA | 1xgp_BA | 1xgq_BA | 1xgt_BA | 1xgu_BA | 1xiw_DC | 1y01_BA | 1y18_BA | 1yjd_HL |
| 1yec_HL | 1yed_BA | 1yee_HL | 1yef_HL | 1yeg_HL | 1yeh_HL | 1yei_HL | 1yej_HL | 1yek_HL | 1yjd_HL |
| 1ymh_BA | 1ynk_HL | 1ynl_HL | 1ynt_BA | 1yqv_HL | 1yuh_BA | 1yy8_BA | 1yy9_DC | 1yyl_HL | 1yym_HL |
| 1z3g_HL | 1za3_BA | 1za6_BA | 1zan_HL | 1zea_HL | 1zls_HL | 1zlu_HL | 1zlv_MK | 1zlw_HL | 1ztx_HL |
| 1zwi_AB | 25c8_HL | 2a01_DC | 2a1w_HL | 2a6d_BA | 2a6i_BA | 2a6j_BA | 2a6k_BA | 2a9m_HL | 2a9n_HL |
| 2aab_HL | 2adf_HL | 2adg_BA | 2adi_BA | 2adj_BA | 2aep_HL | 2aeq_HL | 2agj_HL | 2ai0_IM | 2aj3_BA |
| 2ajs_HL | 2aju_HL | 2ajv_HL | 2ajx_HL | 2ajy_HL | 2ajz_BA | 2ak1_HL | 2ap2_BA | 2arj_BA | 2atk_AB |
| 2b0s_HL | 2b1a_HL | 2blh_HL | 2b2x_HL | 2b4c_HL | 2bdn_HL | 2bfv_HL | 2bjm_HL | 2bmk_BA | 2bab_AB |
| 2boc_AB | 2brr_HL | 2clo_BA | 2c1p_BA | 2cgr_HL | 2cja_HL | 2ck0_HL | 2cmr_HL | 2d03_HL | 2d7t_HL |
| 2dbl_HL | 2dd8_HL | 2ddq_HL | 2dlf_HL | 2dqc_HL | 2dqd_HL | 2dqe_HL | 2dqf_BA | 2dqq_HL | 2dqh_HL |
| 2dqi_HL | 2dqj_HL | 2dqt_HL | 2dqu_HL | 2dtg_AB | 2dwd_AB | 2dwe_AB | 2e27_HL | 2eh7_HL | 2eh8_HL |
| 2eiz_BA | 2eks_BA | 2exw_CD | 2exy_CD | 2ez0_CD | 2f19_HL | 2f58_HL | 2f5a_HL | 2f5b_HL | 2fat_HL |
| 2fb4_HL | 2fbj_HL | 2fd6_HL | 2fec_HL | 2fed_CD | 2fee_HL | 2fjf_HL | 2fjg_BA | 2fjh_BA | 2fl5_BA |
| 2fr4_BA | 2fx7_HL | 2fx8_HL | 2fx9_HL | 2g2r_BA | 2g5b_BA | 2g60_HL | 2g75_HL | 2gcy_BA | 2gfb_BA |
| 2ghw_bB | 2gjj_Aa | 2gjz_BA | 2gk0_HL | 2gki_Aa | 2gsg_BA | 2gsi_HG | 2h1p_HL | 2h2p_CD | 2h2s_CD |
| 2h8p_AB | 2h9g_BA | 2hfe_AB | 2hfg_HL | 2hg5_AB | 2hh0_HL | 2hjf_AB | 2hkf_HL | 2hkh_HL | 2hlf_CD |
| 2hmi_DC | 2hrp_HL | 2ht2_CD | 2ht3_CD | 2ht4_CD | 2htk_CD | 2htl_CD | 2hvj_AB | 2hvk_AB | 2hwz_HL |
| 2i5y_HL | 2i60_HL | 2i9l_BA | 2ibz_XY | 2iff_HL | 2ig2_HL | 2igf_HL | 2ihl_AB | 2ih3_AB | 2ipt_HL |
| 2ipu_GK | 2iq9_HL | 2itc_AB | 2itd_AB | 2j4w_HL | 2j5l_CB | 2j6e_HL | 2j88_HL | 2jb5_HL | 2jel_HL |
| 2jix_DG | 2jk5_AB | 2kh2_bB | 2ltq_FE | 2mop_HL | 2mpa_HL | 2nlj_BA | 2nr6_DC | 2ntf_BA | 2nxy_DC |
| 2nxz_DC | 2ny0_DC | 2ny1_DC | 2ny2_DC | 2ny3_DC | 2ny4_DC | 2ny5_HL | 2ny6_DC | 2ny7_HL | 2nyy_DC |
| 2nz9_DC | 2o5x_HL | 2o5y_HL | 2ojz_HL | 2ok0_HL | 2op4_HL | 2oqj_BA | 2or9_HL | 2osl_AB |
| 2otu_BA | 2otw_HL | 2oz4_HL | 2p7t_AB | 2p81_BA | 2p8p_BA | 2pop_BA | 2pw1_BA | 2pw2_BA | 2q76_BA |
| 2q8a_HL | 2q8b_HL | 2qhr_HL | 2qqk_HL | 2qql_HL | 2qqn_HL | 2qr0_BA | 2qsc_HL | 2r0k_HL | 2r01_HL |
| 2r0w_HL | 2r0z_HL | 2r1w_BA | 2rlx_BA | 2rly_BA | 2r23_BA | 2r29_HL | 2r2b_BA | 2r2e_BA | 2r2h_BA |
| 2r4r_HL | 2r4s_HL | 2r56_HL | 2r69_HL | 2r8s_HL | 2r9h_CD | 2rcs_HL | 2uud_HL | 2uyl_BA | 2uzi_HL |
| 2v17_HL | 2v7h_BA | 2v7n_BA | 2vc2_HL | 2vdk_BA | 2vdl_HL | 2vdm_HL | 2vdn_HL | 2vdo_HL | 2vdp_HL |
| 2vdq_HL | 2vdr_HL | 2vh5_HL | 2vir_BA | 2vis_BA | 2vit_BA | 2vl5_AB | 2vql_BA | 2vwe_EC | 2vxq_HL |
| 2vxs_HL | 2vxt_HL | 2vzu_HL | 2vxv_HL | 2w0f_AB | 2w60_AB | 2w65_AB | 2w9d_HL | 2w9e_HL | 2wub_HL |
| 2wuc_HL | 2x7l_AB | 2xa8_HL | 2xkn_HL | 2xqy_GL | 2xra_HL | 2xtj_DB | 2xwt_AB | 2xza_HL | 2xzc_HL |
| 2xzq_HL | 2y06_HL | 2y07_HL | 2y36_HL | 2y5t_AB | 2y6s_DC | 2ybr_AB | 2yc1_AB | 2yk1_HL | 2ykl_HL |
| 2ypv_HL | 2yss_BA | 2z4q_BA | 2z91_AB | 2z92_AB | 2zch_HL | 2zck_HL | 2zcl_HL | 2zjs_HL | 2zkh_HL |
| 2zpk_HL | 2zuq_FE | 32c2_BA | 35c8_HL | 3a67_HL | 3a6b_HL | 3a6c_HL | 3aaz_AB | 3ab0_BC | 3auv_Aa |
| 3b2u_CD | 3b2v_HL | 3b9k_DC | 3bae_HL | 3be1_HL | 3bgf_BC | 3bkc_HL | 3bkj_HL | 3bkm_HL |
| 3bky_HL | 3bn9_DC | 3bpc_BA | 3bqu_DC | 3bsz_HL | 3bt2_HL | 3bz4_BA | 3c09_CB | 3c2a_HL | 3c5s_DC |
| 3c6s_BA | 3cfb_BA | 3cfc_HL | 3cfd_BA | 3cfe_BA | 3cfj_BA | 3cfk_BA | 3ck0_HL | 3cle_HL | 3clf_HL |
| 3cmo_HL | 3cvh_HL | 3cvi_HL | 3cx5_JK | 3cxd_HL | 3cxh_JK | 3d0v_BA | 3d69_BA | 3d85_BA | 3d9a_HL |
| 3det_CD | 3dgg_BA | 3dif_BA | 3dsf_HL | 3dur_BA | 3dus_BA | 3duu_BA | 3dv4_BA | 3dv6_BA | 3dvg_BA |
| 3dvn_BA | 3e8u_HL | 3efd_HL | 3eff_BA | 3ehb_CD | 3ejy_CD | 3ejz_CD | 3eo0_BA | 3eol_BA | 3eo9_HL |

SUPPLEMENTARY TABLE 9-continued

List of antibody V-region scaffold structures used in this study for hotspots graft design. Each scaffold is designated as: PDB + "_" + $V_H$ chain ID + $V_L$ chain ID.

| | | | | | | | | | |
|---|---|---|---|---|---|---|---|---|---|
| 3eoa_BA | 3eob_BA | 3eot_HL | 3esu_fF | 3esv_Ff | 3et9_Ff | 3etb_Ff | 3eyf_BA | 3eyo_DC | 3eys_HL |
| 3eyu_HL | 3eyv_BA | 3f58_HL | 3f5w_AB | 3f7v_AB | 3f7y_AB | 3fb5_AB | 3fb6_AB | 3fb7_AB | 3fb8_AB |
| 3fct_BA | 3ffd_AB | 3fku_Ss | 3fmg_HL | 3fn0_HL | 3fo0_HL | 3fol_BA | 3fo2_BA | 3fo9_BA | 3fzu_CD |
| 3g04_BA | 3g5v_BA | 3g5x_BA | 3g5y_BA | 3g5z_BA | 3g6a_BA | 3g6d_HL | 3g6j_FE | 3gb7_AB | 3gbn_HL |
| 3ggw_BA | 3ghb_HL | 3ghe_HL | 3gi8_HL | 3gi9_HL | 3giz_HL | 3gje_BA | 3gjf_HL | 3gk8_HL | 3gkw_HL |
| 3gkz_aA | 3gm0_Aa | 3gnm_HL | 3go1_HL | 3grw_HL | 3h0t_BA | 3h3b_cC | 3h42_HL | 3hae_HL | 3hb3_CD |
| 3hc0_AB | 3hc3_HL | 3hc4_HL | 3hfm_HL | 3hi1_BA | 3hi5_HL | 3hi6_HL | 3hmw_HL | 3hmx_HL | 3hns_HL |
| 3hnt_HL | 3hnv_HL | 3hpl_AB | 3hr5_BA | 3hzk_HL | 3hzm_BA | 3hzv_BA | 3hzy_BA | 3i02_BA | 3i2c_HL |
| 3i50_HL | 3i75_HL | 3i9g_HL | 3idg_BA | 3idj_BA | 3idm_BA | 3idn_BA | 3idz_HL | 3idy_BC | 3iet_BA |
| 3if1_BA | 3ifl_HL | 3ifn_HL | 3ifo_AB | 3ifp_AB | 3iga_AB | 3ijh_BA | 3ijs_BA | 3ijy_BA | 3ikc_BA |
| 3inu_HL | 3iu3_AB | 3ivk_AB | 3ixt_AB | 3iy0_HL | 3iy1_BA | 3iy2_BA | 3iy3_BA | 3iy4_BA | 3iy5_BA |
| 3iy6_BA | 3iy7_BA | 3iyw_HL | 3jls_HL | 3j2x_BA | 3j2y_BA | 3j2z_BA | 3j30_BA | 3juy_Aa | 3jwd_HL |
| 3jwo_HL | 3k2u_HL | 3kdm_BA | 3kj4_CB | 3kj6_HL | 3klh_DC | 3kr3_HL | 3ks0_HL | 3kyk_HL | 3kym_BA |
| 3llo_HL | 3l5w_BA | 3l5x_HL | 3l5y_HL | 3l7e_BA | 3l7f_BA | 3l95_BA | 3ld8_CB | 3ldb_CB | 3lev_HL |
| 3lex_AB | 3ley_HL | 3lh2_JN | 3liz_HL | 3lmj_HL | 3loh_AB | 3lqs_HL | 3ls4_HL | 3ls5_HL | 3lzf_HL |
| 3m8o_HL | 3ma9_HL | 3mac_HL | 3mbx_HL | 3mck_BA | 3mcl_HL | 3mj8_BA | 3mj9_HL | 3mlr_HL | 3mlu_HL |
| 3mlw_HL | 3mlx_HL | 3mly_HL | 3mlz_HL | 3mme_AB | 3mnv_BA | 3mnw_BA | 3mnz_BA | 3mol_BA | 3moa_HL |
| 3mob_HL | 3mod_HL | 3mxv_HL | 3mxw_HL | 3n85_HL | 3n9g_HL | 3na9_HL | 3naa_HL | 3nab_HL | 3nac_HL |
| 3ncj_HL | 3ncy_PS | 3nfp_AB | 3nfs_HL | 3ngb_BC | 3nh7_HL | 3nid_EF | 3nif_EF | 3nig_EF | 3nn8_AB |
| 3nps_BC | 3ncc_HL | 3nz8_AB | 3nzh_HL | 3o0r_HL | 3o11_BA | 3o2d_HL | 3o2v_HL | 3o2w_HL | 3o41_AB |
| 3o45_AB | 3o6k_HL | 3o6l_HL | 3o6m_HL | 3oau_HL | 3oay_HL | 3oaz_HL | 3ob0_HL | 3ogc_AB | 3ojd_BA |
| 3okd_BA | 3oke_BA | 3okk_BA | 3okl_BA | 3okm_BA | 3okn_BA | 3oko_BA | 3opz_IM | 3or6_AB | 3or7_AB |
| 3oz9_HL | 3p0v_HL | 3p0y_HL | 3p11_BA | 3p30_HL | 3pgf_HL | 3pho_BA | 3phq_BA | 3piq_CD | 3pjs_BA |
| 3pnw_BA | 3pp3_HL | 3pp4_HL | 3q1s_HL | 3q3g_BA | 3q6g_HL | 3qa3_BA | 3qct_HL | 3qcu_HL | 3qcv_HL |
| 3qeh_AB | 3qg6_BA | 3qg7_HL | 3qhf_HL | 3qnx_BA | 3qo0_BA | 3qo1_BA | 3qos_HL | 3qot_HL | 3qpq_DC |
| 3qpx_HL | 3qq9_DC | 3qrg_HL | 3qum_BA | 3qwo_AB | 3r06_BA | 3r08_HL | 3r1g_HL | 3ra7_HL | 3raj_HL |
| 3rhw_FN | 3ri5_FN | 3ria_FN | 3rif_FN | 3rkd_DC | 3ru8_HL | 3rvt_DC | 3rvu_DC | 3rvv_DC | 3rvw_DC |
| 3rvx_DC | 3s34_HL | 3s35_HL | 3s36_HL | 3a37_HL | 3s62_HL | 3s88_HL | 3s96_AB | 3sdy_HL | 3se8_HL |
| 3se9_HL | 3sgd_HL | 3sge_HL | 3skj_HL | 3sm5_HL | 3so3_CB | 3sob_HL | 3sqo_HL | 3stl_AB | 3stz_AB |
| 3sy0_BA | 3t3m_EF | 3t3p_EF | 3t4y_BA | 3t65_HL | 3t77_BA | 3tcl_AB | 3tnm_HL | 3tnn_AB | 3tt1_HL |
| 3u0t_BA | 3u0w_HL | 3u30_CB | 3u46_AB | 3u4b_HL | 3u6r_AB | 3u7w_HL | 3u7y_HL | 3u9p_HL | 3u9u_AB |
| 3uaj_CD | 3ubx_GI | 3uc0_HL | 3uji_HL | 3ujj_HL | 3ujt_HL | 3uls_EA | 3ulu_DC | 3ulv_DC | 3umt_Aa |
| 3uo1_HL | 3utz_BA | 3ux9_Bb | 3uyp_Aa | 3uyr_HL | 3uze_Aa | 3uzq_aA | 3uzv_Bb | 3v0v_AB | 3v0w_HL |
| 3v4p_HL | 3v4u_HL | 3v4v_HL | 3v52_HL | 3v6f_AB | 3v6o_CE | 3v6z_AB | 3v7a_EH | 3ve0_HL | 3vfg_HL |
| 3vg0_HL | 3vg9_CB | 3vga_CB | 3vi3_FE | 3vi4_FE | 3vrl_EF | 3vw3_HL | 3w11_CD | 3w12_CD | 3w13_CD |
| 3w14_CD | 3zdx_EF | 3zdy_EF | 3zdz_EF | 3ze0_EF | 3ze1_EF | 3ze2_EF | 3zkm_CD | 3zkn_CD | 3ztj_GH |
| 3ztn_HL | 43c9_BA | 43ca_BA | 4a6y_BA | 4aeh_HL | 4aei_HL | 4ag4_HL | 4a18_HL | 4ala_HL | 4am0_AB |
| 4amk_HL | 4at6_AB | 4d9l_HL | 4d9q_ED | 4d9r_ED | 4dag_HL | 4dcq_BA | 4dgi_HL | 4dgv_HL | 4dgy_HL |
| 4dke_HL | 4dkf_HL | 4dn3_HL | 4dn4_HL | 4dtg_HL | 4dvb_AB | 4dvr_HL | 4dw2_HL | 4ebq_HL | 4ene_CD |
| 4eow_HL | 4ers_HL | 4etq_AB | 4evn_AB | 4f2m_AB | 4f33_BA | 4f37_FK | 4f3f_BA | 4f57_HL | 4f58_HL |
| 4f9l_cC | 4f9p_cC | 4fab_HL | 4ffv_DC | 4ffw_DC | 4ffy_HL | 4ffz_HL | 4fg6_CD | 4fnl_HL | 4fp8_HL |
| 4fq1_HL | 4fq2_HL | 4fqc_HL | 4fqh_AB | 4fqi_HL | 4fqj_HL | 4fqk_EF | 4fql_HL | 4fqq_BA | 4fqr_ab |
| 4fqv_HL | 4fqy_HL | 4g3y_HL | 4g5z_HL | 4g6a_CD | 4g6f_BD | 4g6j_HL | 4g6k_HL | 4g6m_HL | 4gag_HL |
| 4gay_HL | 4gms_HL | 4gmt_HL | 4gw4_AB | 4gxu_MN | 4gxv_HL | 4h0g_Aa | 4h0h_bB | 4h0i_aA | 4h20_HL |
| 4hbc_HL | 4hc1_HL | 4hcr_HL | 4hdi_BA | 4hf5_HL | 4hfu_HL | 4hfw_BA | 4hg4_JK | 4hgw_BA | 4hix_HL |
| 4hj0_CD | 4hk0_CD | 4hk3_JN | 4hlz_GH | 4hpo_HL | 4hpy_HL | 4hs6_BA | 4hs8_HL | 4htl_HL | 4hwb_HL |
| 4hwe_HL | 4hzl_AB | 4i3r_HL | 4i3s_HL | 4i77_HL | 4i9w_ED | 4idj_HL | 4imk_AD | 4iml_AB | 4jlu_DC |
| 4j6r_HL | 4j8r_BA | 4jam_HL | 4jan_AB | 4jb9_HL | 4jdv_AB | 4jha_HL | 4jhw_HL | 4jkp_HL | 4jm2_AB |
| 4jm4_HL | 4jn1_HL | 4jn2_HL | 4jpi_HL | 4jpk_HL | 4jpw_HL | 4jqi_HL | 4jr9_HL | 4jre_BC | 4jy4_BA |
| 4jy5_HL | 4jy6_BA | 4jzn_IP | 4jzo_AB | 4ktu_HL | 4k3d_HL | 4k3e_IM | 4km_HL | 4k8r_DC | 6fab_HL |
| 7fab_HL | 8fab_HL | 2ymx_HL | 3mls_HL | 3mlv_HL | 3t2n_HL | 3w9d_AB | 3w9e_AB | 3wbd_aA | 3wd5_HL |
| 4fz8_HL | 4fze_HL | 4gq9_HL | 4gsd_HL | 4gw1_BA | 4gw5_BA | 4h88_BA | 4hh9_BA | 4hha_BA | 4hie_BA |
| 4hih_BA | 4hii_BA | 4hij_BA | 4hjg_BA | 4hkz_BA | 4hxa_HL | 4hxb_HL | 4iof_EF | 4ioi_BA | 4irz_HL |
| 4jfx_HL | 4jfy_HL | 4jfz_HL | 4jo1_HL | 4jo2_HL | 4jo3_HL | 4jo4_HL | 4jpv_HL | 4k3j_HL | 4k7p_HL |
| 4k94_HL | 4k9e_HL | 4kjp_CD | 4kjq_CD | 4kjw_DC | 4kk5_CD | 4kk6_CD | 4kk8_CD | 4kk9_CD | 4kka_CD |
| 4kkb_CD | 4kkc_CD | 4kkl_CD | 4kro_DC | 4krp_DC | 4kuc_FE | 4kvc_HL | 4kyl_HL | 4lbe_AB | 4lcu_AB |
| 4leo_AB | 4lkc_BA | 4llv_HL | 4lmq_HL | 4lou_CD | 4lss_HL | 4lst_HL | 4lsu_HL | 4lsv_HL | 4mld_HL |
| 4m43_HL | 4m48_HL | 4m5y_HL | 4m5z_HL | 4mhh_HL | 4mhj_WV | 4msw_AB | | | |

SUPPLEMENTARY TABLE 10

Amino add sequences of Keap1 and LS146-scFv constructs used for crystallisation.

| Protein construct | Sequence |
|---|---|
| Keap1 (Kelch 1-6 domains, AA 314-611) (SEQ ID NO: 40) | GSMGHAPKVGRLIVTAGGYFRQSLSYLEAYNPQGTWLDLADEQVPRSGLAGCWGGLLYAVGGRNNSPDGNTDSSALDCY NPMTNQWSPCAPMSVPRNRIGGVVIDGHIYAVGGSHGCIHHNSVERYEPERDEWHLVAPMLTRRIGVGVAVLNRLLYAVG GFDGTNRLNSAECYYPERNEWRMITAMNTIRSGAGVCVLHNCIYAAGGYDGDDQLNSVERYDVETETWTFVAPMKHRRS ALGITVHQGRTYVLGGYDGHTFLDSVECYDPDTDWSEVTRMTSGRSGVGVAVTME |

SUPPLEMENTARY TABLE 10-continued

Amino add sequences of Keap1 and LS146-scFv constructs used for crystallisation.

| Protein construct | Sequence |
| --- | --- |
| LS146-scFv (SEQ ID NO: 41) | EVQLVESGGGLVQPGGSLRLSCAASGFAISASSIHWVRQAPGKCLEWVASIDPETGETLYAKSVAGRFTISADTSKNTAYLQMNSLRAEDTAVYYCARAYAGDGVYYADVWGQGTLVTVSSGGGGSGGGGSGGGGSGGGGSDIQMTQSPSSLSASVGDRVTITCRASQSVSSAVAWYQQKPGKAPKLLIYASSLYSGVPSRFSGSRSGTDFTLTISSLQPEDFATYYCQQSYSFPSTFGCGTKVEIKRTENLYFQGHHHHHHHHHH |

SUPPLEMENTARY TABLE 11

Crystallography data collection and structure refinement statistics.

| | LS146-scFv/Keap1 |
| --- | --- |
| Data collection | |
| Space group | P2$_1$ |
| Cell dimensions | |
| a, b, c (Å) | 70.5, 69.8, 99.6 |
| α, β, γ (°) | 90.0, 90.2, 90.0 |
| Resolution (Å) | 29.69-1.85 |
| R$_{sym}$ or R$_{merge}$ | 0.049 |
| I/σI | 11.2 |
| Completeness (%) | 99.1% |
| Redundancy | 3.1 |
| Refinement | |
| Resolution (Å) | 1.85 |
| No. reflections | 265541 |
| R$_{work}$/R$_{free}$ | 22.1/26.1 |
| No. atoms | |
| Protein | 7905 |
| Ligand/ion | 0 |
| Water | 532 |
| B-factors | |
| Protein | 25.96 |
| Ligand/ion | N/A |
| Water | 29.41 |
| R.m.s deviations | |
| Bond lenghts (Å) | 0.013 |
| Bond angles (°) | 1.52 |

SUPPLEMENTARY TABLE 12

Binding affinities of the ordered antibody Fab designs from hotspots graft. Dissociation constants (K$_D$) were determined by SPR.

| Design | Scaffold[1] | Hotspots positions | TGFβ1 K$_D$ (nM) | TGFβ2 K$_D$ (nM) | TGFβ3 K$_D$ (nM) |
| --- | --- | --- | --- | --- | --- |
| 184 | 3MXW | V$_L$52I, V$_L$54V, V$_L$56I, V$_H$100L | 106 | Low binding | 32.9 |
| 186 | 3NAC | V$_L$52I, V$_L$54V, V$_L$56I, V$_H$100$^B$L | ND | ND | ND |
| 187 | 3OB0 | V$_H$33I, V$_L$93L, V$_L$94V | ND | ND | ND |

SUPPLEMENTARY TABLE 13

Fv regions' amino acid sequences of ordered antibody designs from hotspots graft.

| Design | SEQ ID NO: | V$_H$ Sequence | V$_L$ Sequence | SEQ ID NO: |
| --- | --- | --- | --- | --- |
| 184 | 42 | QVQLQQSGPELVRPGVSVKISCKGSGYTFIAEMLHWVKQSHAESLEWIGLIIPAVGITYYNQKFKDKATMTVDIASSTAYLELARLTSEDSAIYYCARSWAEGLFFDYWGQGTLVT | DIVMTQTPKFLLVSAGDKVTITCKASQSVSNALTWYQQKPGQSPKLLIYYASNRYTGVPDRFTGSGYGTDFTFTISTVQAEDLAVYFCQQDYGAPPTFGGGTKVEIKRTV | 43 |
| 186 | 44 | EVQLVQSGAEVKKPGESLKISCKGSGYSFTAYWISWVRQMPGKGLEWMGRIIPSVSITNYSPSFQGHVTISADKAISTAYLQWSSLKASDTAMYYCARLLMQGAMLTFDSWGQGTLVT | DIQMTQSPSSLSASVGDRVTITCRASQSIGLALAWYQQKPGKAPKLLIYAASSLQSGVPSRFSGSGSGTDFTLTISSLQPEDFATYYCQQGNTLSYTFGQGTKVEIKRTV | 45 |
| 187 | 46 | EVQLVESGGGLVKAGGSLILSCGVSNFRIAYHIMNWVRRVPGGGLEWVASIVTIDAATAYADAVKGRFTVSRDDASDFVYLQMHKMRVEDTAIYYCARKGSDVTQDNDPFDAWGPGTVVT | DVVMTQSPSTLSASVGDTITITCRASSGGGTWLAWYQQKPGKAPKLLIYKASTLKTGVPSRFSGSGSGTEFTLTISGLQFDDFATYYCQHYSLVYATFGQGTRVEIKRTV | 47 |

SUPPLEMENTARY TABLE 14

Receptors' pan-blocking IC$_{50}$s of Fab 184 design from hotspots graft in the reporter gene assay (n = 2).

| Design | TGFβ1 IC$_{50}$ (nM) | TGFβ2 IC$_{50}$ (nM) | TGFβ3 IC$_{50}$ (nM) |
|---|---|---|---|
| 184 | 52.8 | 36.8 | 10.6 |

Pseudo-Codes
Pseudo Codes of Hotspots Grafting onto Antibody Scaffold Structures:

```
# Main function: iterate all antibody scaffold structures, do graftScaffoldOntoHotspots
DEF Main (String AntigenPDB, String HotspotsPDB, String ScaffoldsPath):
  # load antigen and hotspots
  Protein antigen = readPDB (AntigenPDB)
  Protein hotspots = readPDB (HotspotsPDB)
  # Iterate each template
  FOR scaffoldPDB IN ScaffoldsPath:
    Protein scaffold = readPDB (scaffoldPDB)
    # generate grafted complex structure
    Protein graft = graftScaffoldOntoHotspots (antigen, hotspots, scaffold)
    # dump the transplant structure
    dumpPDB (graft)
# FUNCTION graftScaffoldOntoHotspots: graft one antibody scaffold onto the hotspots
DEF graftScaffoldOntoHotspots (Protein Antigen, Protein Hotspots, Protein Scaffold):
  # Enumerate all hotspots triplets and store in hotspotsTripletList
  List hotspotsTripletList = [ ]
  FOR r1, r2, r3 IN hotspots:
    Triplet hotspotsTriplet = setupTriplet (r1, r2, r3)
    hotspotsTripletList.append (hotspotsTriplet)
  # Enumerate all template CDR triplets and store in scaffoldTripletList
  List scaffoldTripletList = [ ]
  FOR r1, r2, r3 IN scaffold's CDR residues:
    Triplet scaffoldTriplet = setupTriplet (r1, r2, r3)
    scaffoldTripletList.append (scaffoldTriplet)
  # iterate each pair of scaffoldTriplets and hotspotsTriplets, find the pair with identical key,
and align the corresponding triplets
  List SolutionList = [ ]
  FOR hotspotsTriplet IN hotspotsTripletList:
    FOR scaffoldTriplet IN scaffoldTripletList:
      IF hotspotsTriplet.key == scaffoldTriplet.key:
        # Alignment and residue mutation
        Align the antibody template onto the Hotspots by corresponding
triplets using rms fitting
        Replace the three template triplet residues with the corresponding
hotspots
        # Clashing check
        Mutate any clashing residues on antibody with antigen's backbones to
alanines
        IF clashes remain after alanine mutation:
          Discard current Graft
        ELSE:
          Append current Graft to the SolutionList
  Sort SolutionList by ascending hotspots RMSD
  # Output the complex structure of antigen and transplanted antibody scaffold (with mutated
Hotpots)
  Return SolutionList.top
# CLASS Triplet and FUNCTION setup Triplet: Setup residue triplets
CLASS Triplet:
  Residue residue1, residue2, residue3
  String key
DEF setupTriplet (Residue r1, Residue r2, Residue r3):
  # Edge lengths of the resdue triangle by residue1.Ca, residue2.Ca, residue3.Ca
  dC$_a$12 = Distance (r1.C$_a$, r2.C$_a$), dC$_a$23 = Distance (r2.C$_a$, r3.C$_a$), dC$_a$13 = Distance (r1.C$_a$, r3.C$_a$)
  # Edge lengths of the resdue triangle by residue1.N, residue2.N, residue3.N
  dN12 = Distance (r1.N, r2.N), dN23 = Distance (r2.N, r3.N), dN13 = Distance (r1.N, r3.N)
  # Edge lengths of the resdue triangle by residue1.C, residue2.C, residue3.C
  dC12 = Distance (r1.C, r2.C), dC23 = Distance (r2.C, r3.C), dC13 = Distance (r1.C, r3.C)
  # Filter the triangles with any length less than 3.5 A
  IF any dC$_a$, dN, or dC <= 3.5:
    Return False
  # r1 and r2 corresponds to the longest Ca. edge, r1 and r3 corresponds to the shortest Ca
edge
  Reorder r1, r2, r3 corresponding to descending dC$_a$12, dC$_a$23, dC$_a$13
  # Indexing key of the triplets by rounding up the edge lengths and concatenating into string
```

-continued

```
   key = String (roundup (dCa1)) + String (roundup (dCa2)) + String (roundup (dCa3)) +
String (roundup (dN1)) + String (roundup (dN2)) + String (roundup (dN3)) + String (roundup
(dC1)) + String (roundup (dC2)) + String (roundup (dC3))
   # return reordered r1, r2, r3 and key into a triplet
   Return Triplet (r1, r2, r3, key)
Pseudo codes of CDRH3 loop swapping of G54.1:
Main function: iterate all antibody CDRH3 loop structures, do swap CDRH3
DEF Main (String AntibodyAntigenComplexPDB, String CDRH3sPath):
   # load antibody-antigen complex PDB structure
   Protein system = readPDB (AntibodyAntigenComplexPDB)
   # chop off wt CDRH3 loop
   Protein truncatedH3System = chop CDRH3 (system)
   # Iterate each exogenous CDRH3 loop structure
   FOR CDRH3LoopPDB IN CDRH3sPath:
      Protein h3loop = readPDB (CDRH3LoopPDB)
      # generate H3 swapped complex structure
      Protein loopswap = swapCDRH3 (truncatedH3System, h3loop)
      # dump the transplant structure
      dumpPDB (loopswap)
FUNCTION swapCDRH3: graft one exogenous CDRH3 loop onto the CDRH3-truncated antibody-
antigen complex structure
DEF swapCDRH3 (Protein truncatedH3System, Protein h3loop):
   # Alignment of the anchor residues of exogenous H3 loop onto those of CDRH3-truncated Fv
      Align the h3loop anchor residues (VH93 and VH103) onto those of
   truncatedH3System
      Remove the original VH93 and VH103 residues from truncatedH3System
      Ligate the backbones of new h3loop's VH93 and VH103 with VH92 and VH104 of
   truncatedH3System, respectively, generating a swappedH3System (new H3 loop inserted into
   original Fv in complex with antigen)
      # Clashing check
      FOR any clashing residues on h3loop with rest of swappedH3System's backbones,
   mutate them to alanine
      IF clashes remain after alanine mutation:
         Discard current swappedH3System
      ELSE:
      # Output the complex structure of antigen-FY and transplanted new H3 loop
         Return current swappedH3System
```

RosettaScripts: AlaScan.xml:

```
<dock_design>
   <FILTERS>
      <AlaScan name=scan partner1=0 partner2=1 scorefxn=score12
   interface_distance_cutoff=8.0 repeats=3/>
   </FILTERS>
   <MOVERS>
      <RepackMinimize name=intermin scorefxn_repack=score12
   scorefxn_minimize=score12 interface_cutoff_distance=8.0 repack_partner1=0
   repack_partner2=0 design_partner1=0 design_partner2=0 minimize_bb=0
   minimize_sc=1
   minimize_rb=0/>
   </MOVERS>
   <PROTOCOLS>
      <Add mover_name=intermin>
      <Add filter_name=scan>
   </PROTOCOLS>
</dock_design>
```

RosettaScripts: InverseRotamers.xml:

```
<dock_design>
   <FILTERS>
      <EnergyPerResidue name=energy pdb_num=79B
      energy_cutoff=0.0/>
   <Ddg name=ddg threshold=-1.0/>
   </FILTERS>
   <MOVERS>
      <TryRotamers name=try pdb_num=79B/>
   </MOVERS>
   <PROTOCOLS>
      <Add mover_name=try/>
      <Add filter_name=energy/>
      <Add filter_name=ddg/>
```

-continued

```
   </PROTOCOLS>
</dock_design>
```

RosettaScripts: ppk.xml:

```
<dock_design>
   <MOVERS>
      <Prepack name=ppk jump_number=0
      scorefxn=score12/> Jump_number=0 to
   prepack the entire structure without moving the partners apart.
      <MinMover name=min scorfxn=score12 chi=1 bb=0 jump=0/>
```

```
        </MOVERS>
        <PROTOCOLS>
            <Add mover_name=ppk/>
            <Add mover_name=min>
        </PROTOCOLS>
    </dock_design>
```

RosettaScripts: MutationScanPB.xml:

```
<dock_design>
    <SCOREFXNS>
        <local_score weights=score12_full patch="pb_elec.wts_patch"/>
        <local_score_soft weights=soft_rep patch="pb_elec.wts_patch"/>
    <SCOREFXNS>
    <TASKOPERATIONS>
        <InitializeFromCommandline name=init/>
        <ProteinInterfaceDesign name=pid repack_chain1=1 repack_chain2=1 design_chain1=0 design_chain2=1 interface_distance_cutoff=8/>
        <ProteinInterfaceDesign name=pio repack_chain1=1 repack_chain2=1 design_chain1=0 design_chain2=0 interface_distance_cutoff=8/>
    </TASKOPERATIONS>
    <MOVERS>
        <AtomTree name=docking_tree docking_ft=1/>
        <MinMover name=min_sc scorefxn=local_score bb=0 chi=1 jump=1/> minimize sc,
rb
        <PackRotamersMover name=pack_interface scorefxn=local_score task_operations=init,pio/>
        <PackRotamersMover name=pack_interface_soft scorefxn=local_score_soft task_operations=init,pio/>
        <ParsedProtocol name=relax_before_baseline>
            <Add mover=docking_tree/>
            <Add mover=pack_interface/>
            <Add mover= min_sc/>
        </ParsedProtocol>
    </MOVERS>
    <FILTERS>
        <Ddg name=ddg scorefxn=local_score confidence=0.0/>
        <Delta name=delta_ddg filter=ddg upper=1 lower=0 range=-0.5 relax_mover=relax_before_baseline/>
        <FilterScan name=scan_binding scorefxn=local_score relax_mover=relax_before_baseline task_operations=pid,init filter=delta_ddg triage_filter=delta_ddg resfile_name="scan.resfile"/>
        <Time name=scan_binding_timer/>
    </FILTERS>
    <PROTOCOLS>
        <Add mover=docking_tree/>
        <Add filter=scan_binding_timer/>
        <Add filter=scan_binding/>
        <Add filter=scan_binding_timer/>
    </PROTOCOLS>
</dock_design>
```

RosettaScripts: FlexbbInterfaceDesign.xml:

```
<dock_design>
    <TASKOPERATIONS>
        <ProteinInterfaceDesign name=pio repack_chain1=1 repack_chain2=1 design_chain1=0 design_chain2=0 interface_distance_cutoff=10/>
        <ReadResfile name=resfile filename="design.resfile"/>
    </TASKOPERATIONS>
    <FILTERS>
        <Ddg name=ddG scorefxn=score12 threshold=-20 repeats=2/>
        <Sasa name=sasa threshold=2000/>
        <CompoundStatement name=ddg_sasa>
            <AND filter_name=ddG/>
            <AND filter_name=sasa/>
    </CompoundStatement>
    </FILTERS>
    <MOVERS>
        <BackrubDD name=backrub partner1=0 partner2=1 interface_distance_cutoff=8.0 moves=1000 sc_move_probability=0.25 scorefxn=score12 small_move_probability=0.15 bbg_move_probability=0.25 task_operations=pio/>
        <RepackMinimize name=des1 scorefxn_repack=soft_rep scorefxn_minimize=soft_rep minimize_bb=0 minimize_rb=1 task_operations=resfile/>
        <RepackMinimize name=des2 scorefxn_repack=score12 scorefxn_minimize=score12 minimize_bb=0 minimize_rb=1 task_operations=resfile> Design & minimization at the interface
        <RepackMinimize name=des3 minimize_bb=1 minimize_rb=0 task_operations=resfile>
        <ParsedProtocol name=design>
            <Add mover_name=backrub/>
            <Add mover_name=des1/>
            <Add mover_name=des2/>
            <Add mover_name=des3 filter_name=ddg_sasa/>
        </ParsedProtocol>
        <GenericMonteCarlo name=iterate scorefxn_name=score12 mover_name=design trials=3/>
        <InterfaceAnalyzerMover name=IAM scorefxn=score12 packstat=1 interface_sc=1 pack_input=1 pack_separated=1 tracer=0 fixedchains=H,L/>
    </MOVERS>
    <PROTOCOLS>
        <Add mover=iterate>
        <Add mover=IAM/>
    </PROTOCOLS>
</dock_design >
```

The invention claimed is:

1. A computer-implemented method, comprising:
   (a) generating a residue-based triplet hash data set for each of the residue triplets from a cognate protein binder, the residues known to bind to a target epitope, each cognate protein binder residue comprising a cognate protein binder residue sub-structure comprising sub-structure characteristic atoms, the hash key set constructed using the data on the special position of by nine vertexes corresponding to the positions of nine characteristic atoms of the three residues and nine edges corresponding to the edges from the three triangles
      wherein the characteristic atoms of the cognate protein binder residue sub-structure comprise any three of the following: the alpha carbon, the backbone carbon atom derived from the carboxyl group, the backbone nitrogen, the backbone oxygen, and the beta carbon of the side chain;
   (b) generating a data set from a 3D database of antibody structures, the dataset comprising triplet hash data on any complementarity-determining region (CDR) residues triplet generated in the same way and the same types of atoms as in step (a);
   (c) using the data set obtained in step (b) to computationally select one or more candidate antibody structures from the 3D database of antibody structures by identifying antibody scaffold triplet structures which are able to accommodate the three cognate protein binder residues in the geometrically matched positions in CDRs, by comparing the respective triplet hash key values, each candidate antibody structure comprising 3D spatial data on a first matching residue, a second matching residue and a third matching residue each comprising a matching residue sub-structure comprising 3 matching residue sub-structure characteristic atoms; and
   (d) calculating a first set of distances representing separations between all possible pairings between characteristic atoms of the same type in different sub-structures of the cognate protein binder residues;
      calculating a second set of distances representing separations between all possible pairings between characteristic atoms of the same type in different sub-structures of the matching residues; and
      comparing the first set of distances to the second set of distances, and selecting one or more candidate antibody structures wherein the difference in the distances is within a predetermined separation threshold;
   (e) outputting the one or more selected candidate antibody structures in a format suitable for use in a process for manufacturing the one or more selected candidate antibodies; and
   (f) manufacturing the one or more selected candidate antibodies using, for each of the selected candidate antibodies, the 3 matching residue sub-structure characteristic atoms of each of the matching residue sub-structures for each of the first matching residue, the second matching residue, and the third matching residue.

2. The method of claim 1, wherein the predetermined threshold is 2.0 Angstroms.

3. The method of claim 1, further comprising replacing in 3D coordinates the matching residues backbone atoms 3D coordinates with the corresponding 3D coordinates of the corresponding cognate binder residue's backbone atoms.

4. The method of claim 1, wherein the three substructure characteristic atoms are the alpha carbon atom, the backbone carbon atom, and the backbone nitrogen atom.

5. The method of claim 1, further comprising iteratively swapping 3D coordinates of the atoms each of one or more of the CDR loops of the candidate antibody structure with 3D coordinates of the atoms of CDR loops from a database of CDR loops.

6. A non-transitory computer readable medium, comprising computer readable instructions which, when executed by a computer, cause the computer to carry out the method of claim 1.

7. The method of claim 1, further comprising detecting geometrical clashing by comparing 3D coordinates of the matching residues, where one or more atoms are calculated to occupy positions that are closer together than is physically possible, between one or more atoms in the candidate antibody structure when bound to the target epitope and one or more atoms in the target epitope.

8. The method of claim 7, further comprising determining whether a detected geometrical clash is with a side chain of a residue of the candidate antibody structure and, if so, replacing the 3D coordinates of the atoms of the side chain by 3D coordinates of atoms of a side chain of another type of amino acid.

9. The method of claim 8, wherein the 3D coordinates of the atoms of the side chain are replaced by 3D coordinates of atoms of an alanine side chain, a glycine side chain, a valine side chain, a serine side chain, a threonine side chain, or homo-alanine side chain.

10. The method of claim 7, further comprising calculating presence of geometrical clash is with a backbone or beta carbon atoms of any candidate antibody residue and, if so, discarding the selected candidate antibody structure and repeating the determination for a different candidate antibody structure selected from the database.

11. The method of claim 1, wherein the method comprises additional step of generation of an index key lookup table comprising residue triplet's information for the residues of a cognate protein binder and the CDR residues of antibodies, the lookup table comprising each vertex residue types and atomic coordinates data.

12. The method of claim 1, further comprising updating one of the candidate antibody 3D structure data for one or more of the matching residues that is an amino-acid residue of a different type compared to the cognate protein binder amino-acid residue type, the updating comprising replacing the 3D atomic coordinates the matching residue with 3D atomic coordinates of a different residue such that a calculated affinity between the resulting 3D antibody structure and the target epitope is higher than a calculated affinity between the candidate antibody structure and the target epitope.

13. The method of claim 1, wherein manufacturing the one or more selected candidate antibodies comprises chemically synthesizing genes encoding variable regions of the candidate antibodies.

14. A method, comprising:
identifying one or more candidate antibody structures that will bind to a target epitope by:
(a) generating a residue-based triplet hash data set for each of the residue triplets from a cognate protein binder, the residues known to bind to the target epitope, each cognate protein binder residue comprising a cognate protein binder residue sub-structure comprising sub-structure characteristic atoms, the hash key set constructed using the data on the special position of by nine vertexes corresponding to the positions of nine characteristic atoms of the three residues and nine edges corresponding to the edges from the three triangles;
wherein the characteristic atoms of the cognate protein binder residue sub-structure comprise any three of the following: the alpha carbon, the backbone carbon atom derived from the carboxyl group, the backbone nitrogen, the backbone oxygen, and the beta carbon of the side chain;
(b) generating a data set from a 3D database of antibody structures, the dataset comprising triplet hash data on any complementarity-determining region (CDR) residues triplet generated in the same way and the same types of atoms as in step (a);
(c) using the data set obtained in step (b) to computationally select one or more candidate antibody structures from the 3D database of antibody structures by identifying antibody scaffold triplet structures which are able to accommodate the three cognate protein binder residues in the geometrically matched positions in CDRs, by comparing the respective triplet hash key values, each candidate antibody structure comprising 3D spatial data on a first matching residue, a second matching residue and a third matching residue each comprising a matching residue sub-structure comprising 3 matching residue sub-structure characteristic atoms; and
(d) calculating a first set of distances representing separations between all possible pairings between characteristic atoms of the same type in different sub-structures of the cognate protein binder residues;
calculating a second set of distances representing separations between all possible pairings between characteristic atoms of the same type in different sub-structures of the matching residues; and
comparing the first set of distances to the second set of distances, and selecting one or more candidate antibody structures wherein the difference in the distances is within a predetermined separation threshold;
manufacturing an antibody according to the identified one or more candidate antibody structures; and
applying a therapy using the manufactured antibody, wherein applying the therapy comprises:
the manufactured antibody achieving a desired mechanism of action based on the target epitope;
the manufactured antibody binding with high affinity to the target epitope; and
the manufactured antibody blocking cognate protein-protein interactions or capturing predicted transition states.

15. The method of claim 14, wherein applying the therapy further comprises the manufactured antibody binding to a BTB-Kelch substrate adaptor protein.

16. The method of claim 15, wherein the BTB-Kelch substrate adaptor protein regulates steady-state levels of a bZIP transcription factor.

17. The method of claim 16, wherein the BTB-Kelch substrate adaptor protein regulates steady-state levels of a bZIP transcription factor in response to oxidative stress.

18. The method of claim 14, wherein the manufactured antibody binding with high affinity to the target epitope comprises the manufactured antibody binding with an affinity of at least the low-to-mid nanomolar range.

19. The method of claim 14, wherein applying the therapy further comprises the manufactured antibody targeting an intracellular protein.

20. The method of claim 14, wherein applying the therapy further comprises the manufactured antibody affecting immune homeostastis.

21. The method of claim 14, wherein applying the therapy further comprises the manufactured antibody affecting fibrosis regulation.

22. The method of claim 13, wherein manufacturing the one or more selected candidate antibodies further comprises transfecting the chemically synthesized genes into a host cell.

\* \* \* \* \*